United States Patent
Subramanian et al.

(10) Patent No.: US 11,142,739 B2
(45) Date of Patent: Oct. 12, 2021

(54) LOADING PLATFORM FOR THREE-DIMENSIONAL TISSUE ENGINEERED SCAFFOLDS

(71) Applicant: The University of Toledo, Toledo, OH (US)

(72) Inventors: Gayathri Subramanian, Toledo, OH (US); Mostafa Elsaadany, Toledo, OH (US); Eda Yildirim-Ayan, Toledo, OH (US)

(73) Assignee: The University of Toledo, Toledo, OH (US)

( * ) Notice: Subject to any disclaimer, the term of this patent is extended or adjusted under 35 U.S.C. 154(b) by 459 days.

(21) Appl. No.: 16/081,977

(22) PCT Filed: Mar. 3, 2017

(86) PCT No.: PCT/US2017/020706
§ 371 (c)(1),
(2) Date: Sep. 4, 2018

(87) PCT Pub. No.: WO2017/152080
PCT Pub. Date: Sep. 8, 2017

(65) Prior Publication Data
US 2019/0093063 A1     Mar. 28, 2019

Related U.S. Application Data

(60) Provisional application No. 62/303,674, filed on Mar. 4, 2016.

(51) Int. Cl.
*C12M 1/42*       (2006.01)
*C12M 3/00*       (2006.01)
*C12M 1/12*       (2006.01)
*A61L 27/60*      (2006.01)
(Continued)

(52) U.S. Cl.
CPC ............. *C12M 35/04* (2013.01); *A61L 27/24* (2013.01); *A61L 27/3804* (2013.01);
(Continued)

(58) Field of Classification Search
None
See application file for complete search history.

(56) References Cited

U.S. PATENT DOCUMENTS 5,512,480 A     4/1996   Sandstrom et al.
5,521,087 A  *  5/1996   Lee .................... A61L 27/3804
                                                    435/366

(Continued)

FOREIGN PATENT DOCUMENTS

WO     2008125883 A1    10/2008
WO     2015081226 A1     6/2015

OTHER PUBLICATIONS

PCT International Search Report and Written Opinion, Application No. PCT/US17/20706, dated Jun. 7, 2017.

*Primary Examiner* — William H. Beisner
(74) *Attorney, Agent, or Firm* — MacMillan, Sobanski & Todd, LLC

(57) ABSTRACT

A scaffold-stretching system includes at least one stretchable loading chamber configured to support a scaffold material and a supply of cells, such as human skin substitute cells, and is configured to allow for cultivation of a cellular three-dimensional scaffold; and a mechanical loading system is configured for application of cyclic and static uniaxial tensile mechanical loading on the cellular three-dimensional scaffold, and is configured to mimic the in vivo environment of musculoskeletal, cardiovascular, and other tissues that experience uniaxial strains.

17 Claims, 50 Drawing Sheets
(38 of 50 Drawing Sheet(s) Filed in Color)

(51) Int. Cl.
  *A61L 27/54* (2006.01)
  *A61L 27/24* (2006.01)
  *A61L 27/38* (2006.01)
  *C12N 5/00* (2006.01)
  *C12Q 1/6883* (2018.01)
  *G01N 33/50* (2006.01)
  *C12N 5/071* (2010.01)

(52) U.S. Cl.
  CPC ............... *A61L 27/54* (2013.01); *A61L 27/60* (2013.01); *C12M 3/00* (2013.01); *C12M 21/08* (2013.01); *C12M 25/14* (2013.01); *C12N 5/0012* (2013.01); *C12Q 1/6883* (2013.01); *G01N 33/5082* (2013.01); *C12N 5/0698* (2013.01); *C12N 2503/06* (2013.01); *C12N 2513/00* (2013.01); *C12N 2521/00* (2013.01); *C12N 2533/54* (2013.01); *C12Q 2600/148* (2013.01); *C12Q 2600/158* (2013.01)

(56) References Cited

U.S. PATENT DOCUMENTS

| | | |
|---|---|---|
| 6,107,081 A | 8/2000 | Feeback et al. |
| 6,586,235 B1 | 7/2003 | Banes |
| 2003/0167556 A1 | 9/2003 | Kelley |
| 2007/0178584 A1 | 8/2007 | Naruse et al. |
| 2008/0097607 A1 | 4/2008 | Bakkar et al. |
| 2012/0219981 A1* | 8/2012 | Muthiah ............... C12M 35/04 435/29 |
| 2013/0105348 A1 | 5/2013 | Koob |
| 2014/0038258 A1 | 2/2014 | Akra et al. |
| 2014/0113345 A1 | 4/2014 | Lee et al. |
| 2015/0168308 A1 | 6/2015 | Iwai et al. |
| 2015/0290105 A1 | 10/2015 | Shin et al. |
| 2016/0326477 A1* | 11/2016 | Fernandez-Alcon ........................ B01D 67/0023 |

* cited by examiner

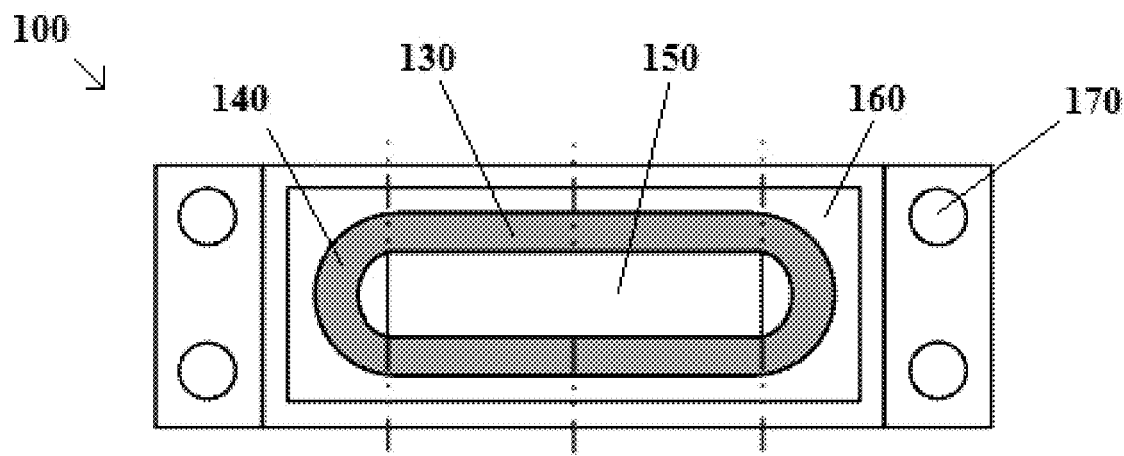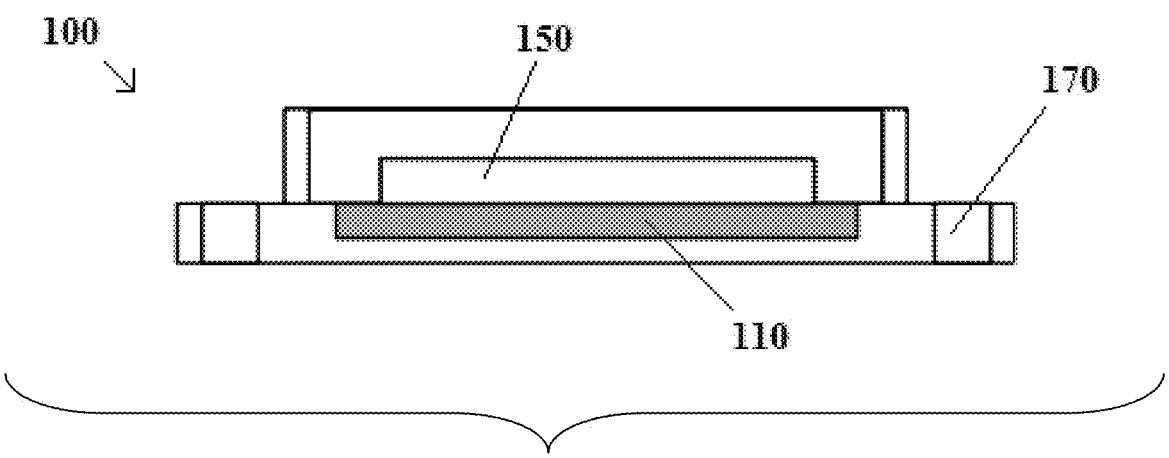
FIG. 1A

| Table 1. Ogden model parameter used for the silicone loading chambers |||
|---|---|---|
| i | $\alpha_i$ | $\mu_i$ (MPa) |
| 1 | 0.68 | 0.075 |
| 2 | 0.001 | 0.03 |
| 3 | 0.35 | 0.114 |

FIG. 16A – Table 1

| Table 2. Viscoelastic Prony series parameters used for collagen constructs |||
|---|---|---|
| i | $g_i$ | $\tau_i$ |
| 1 | 0.0009 | 0.08 |
| 2 | 0.4045 | 0.136 |
| 3 | 0.1289 | 84.49 |
| 4 | 0.0001 | 290.5 |
| 5 | 0.0151 | 350.1 |
| 6 | 0.1206 | 1145 |

FIG. 16B – Table 2

LOADING PLATFORM FOR THREE-DIMENSIONAL TISSUE ENGINEERED SCAFFOLDS

CROSS-REFERENCE TO RELATED APPLICATIONS

This application claims priority to U.S. Provisional Application No. 62/303,674, filed under 35 U.S.C. § 111(b) on Mar. 4, 2016, the entire disclosure of which is expressly incorporated herein by reference for all purposes.

STATEMENT REGARDING FEDERALLY SPONSORED RESEARCH

This invention was not made with government support and the government has no rights in the invention.

BACKGROUND

There are challenges when attempting to design uniaxial mechanical loading systems for loading three-dimensional cellular scaffolds. For example, three dimensional constructs, especially gel-based scaffolds, have low mechanical integrity, and clamping the scaffolds directly to a fixture in order to apply stretch is challenging and can disintegrate the scaffold. Clamping also causes stress concentration at the ends due to the gripping effect, and can lead to non-homogenous stress distribution within the scaffold. Thus, there is a need for improved uniaxial mechanical loading systems for loading three-dimensional cellular scaffolds.

Furthermore, there is a need for better methods of testing cosmetic skin care products. Currently, cosmetic companies can generate about 20 skin care cosmetic formulations in a week, but due to limitations of current skin cosmetic testing platforms, they can only test about 100 formulations in a year. Thus, there is also a great demand for creating an efficient, reliable, and custom surface area-sized human skin substitute cosmetic testing platform that is able to reduce the product development cycle time.

There is no admission that the background art disclosed in this section legally constitutes prior art.

SUMMARY

In a first broad aspect, there is provided herein a scaffold-stretching system (also referred to herein as a uniaxial tensile strain bioreactor or a loading platform) that includes: at least one stretchable loading chamber that is configured to support a scaffold material and a supply of cells. The stretchable loading chamber is also configured to allow for cultivation of a cellular three-dimensional scaffold. The scaffold-stretching system also includes a mechanical loading system that is configured for application of cyclic and static uniaxial tensile mechanical loading on the cellular three-dimensional scaffold. The scaffold-stretching system mimics the in vivo environment of musculoskeletal, cardiovascular, and other tissues that experience uniaxial strains.

In certain embodiments, the stretchable loading chamber includes at least one groove on a top surface of the stretchable loading chamber, the groove having opposing linear portions that are connected by opposing semi-circular portions, wherein the semicircular portions of the groove link the opposing linear portions of the scaffold, and provide mechanical support and stability during stretching.

In certain embodiments, the opposing linear portions and opposing semi-circular portions define a mound at a center of the stretchable loading chamber. The mound is configured to hold the scaffold in place during stretching, and is configured to prevent the opposing linear and semi-circular portions from touching during loading.

In certain embodiments, the stretchable loading chamber includes at least one well that is configured to hold a sufficient amount of a culture medium for cell survival, proliferation, and differentiation.

In certain embodiments, the stretchable loading chamber includes pin holes positioned at opposing ends of the stretchable loading chamber that are configured to accept holding pins of supporting base plates in order to apply loading.

In certain embodiments, the stretchable loading chamber comprises silicone.

The mechanical loading system includes at least one fixed plate and at least one movable plate, and at least one driving mechanism. Each of the fixed and movable plates has upper surfaces that are positioned in the same plane. Also, each of the fixed and movable plates has a plurality of pins extending from the upper surface that are configured for holding at least a portion of the stretchable loading chamber.

The driving mechanism is operatively connected to a first end of the movable plate. The driving mechanism is configured for moving the movable plate in a uniaxial direction toward and away from the fixed plate.

In certain embodiments, the fixed plate is configured to provide a base for slidably supporting the stretchable loading chamber, and to support the weight of the stretchable loading chamber when loaded with scaffold and media during mechanical loading.

In certain embodiments, the movable plate is configured to transmit uniaxial motion to the stretchable loading chamber. A gap exists between the fixed plate and a second end of the movable plate. The length of the gap is sufficient for preventing the fixed and movable plates from coming into contact during a cyclic motion.

In certain embodiments, the fixed plate and the movable plate are slidingly supported by opposing guiding sleeves. The opposing guiding sleeves allow translation motion of the movable plate, while the fixed plate is held in place by the guiding sleeves.

In certain embodiments, the length of the guiding sleeve is such that the movable plate can be pulled up to strain values that would cover the entire range of physiological loading regimes, determined in terms of the uniaxial elongation of the linear part of the groove of the silicone loading chamber.

In certain embodiments, the driving mechanism includes: a ball screw drive assembly having a ball nut and a ball screw; and one or more connecting rods. The ball screw drive assembly is configured to convert rotational motion to uniaxial translational motion. The one or more connecting rods each have first ends attached to the first end of the movable plate, and have second ends attached to the ball screw drive assembly. The connecting rods are configured to transfer linear motion of the ball nut due to rotation of the ball screw to the movable plate, thereby producing stretching of the stretchable loading chambers.

In certain embodiments, a two-phase high torque stepper motor is operatively connected to the ball screw assembly, wherein the two-phase high torque stepper motor is capable of producing controlled and precise strains at specified frequencies.

In certain embodiments, the scaffold material comprises a cellular gel-based scaffold. In certain embodiments, the scaffold-stretching system includes a human skin substitute (HSS) in the stretchable loading chamber. In particular embodiments, the HSS comprises collagen and human keratinocytes.

Also provided herein is a method for stretching a cellular three-dimensional scaffold. The method can generally include: loading at least one cellular three-dimensional scaffold material into a stretchable loading chamber that is configured to support the three-dimensional scaffold material; loading a supply of cells into the stretchable loading chamber; and applying a mechanical loading to the stretchable loading chamber, wherein the mechanical loading provides cyclic and static uniaxial tensile mechanical loading on the cellular three-dimensional scaffold to stretch the cellular three-dimensional scaffold.

In certain embodiments, the method can further include cultivating the cells in the loading chamber for a predetermined period of time.

Also provided herein is a method for testing a cosmetic skin care product, the method comprising culturing a human skin substitute (HSS) in a stretchable loading chamber, applying a mechanical loading to the stretchable loading chamber, where the mechanical loading provides cyclic and static uniaxial tensile mechanical loading on the HSS so as to simulate wrinkled or stretched skin with wrinkled or stretched HSS, topically applying a cosmetic skin care product to the wrinkled or stretched HSS, and analyzing the HSS after a period of time to test the cosmetic skin care product. In certain embodiments, the period of time is about 3 hours, about 12 hours, or about 24 hours following the topical application. In certain embodiments, the analyzing comprises characterizing gene expression in the HSS. In particular embodiments, the gene expression is analyzed using real-time polymerase chain reaction (RT-PCR). In particular embodiments, the expression of Hydroxymethylbilane synthase (HMBS) is analyzed. In certain embodiments, the analyzing comprises characterizing expression of one or more of collagen synthesis, elastin, matrix metalloproteinases (MMPs), fibronectin, and laminin in the HSS. In certain embodiments, the cosmetic skin care product comprises a moisturizer, a foot powder or spray, a face or neck cream or lotion, a face wash or cleanser, a body or hand cream or lotions, a face mask, an anti-aging cream, an eye care cream, a face serum, a lip balm, or an exfoliant.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIGS. 1A-1D: Schematic illustrations of a stretchable loading chamber. FIG. 1A top is a top view of a stretchable loading chamber. FIG. 1A bottom is a side elevation view of the stretchable loading chamber. Light grey represents the stretchable loading chamber, and the dark grey represents a cellular gel-based scaffold that has been poured into a groove within the stretchable loading chamber. The groove is composed of opposing linear portions that are connected by opposing semi-circular portions. Linear portions of the groove-region are for scaffold characterization. Semicircular portion of the groove operate to link two linear portions of the scaffold, and provide mechanical support and stability during stretch. An island, which is a mound at the center, holds the scaffold in place so that the scaffolds within the opposing portions do not come together during loading. A well is configured to hold a sufficient amount of a culture medium for cell survival, proliferation, and differentiation. Pin holes are configured to accept holding pins of the supporting base plates in order to apply loading.

FIG. 1B: Side elevation view of stretchable loading chamber, partially in phantom, displaying non-limiting example dimensions. In one non-limiting example, the stretchable loading chamber measures 25×4×2 mm (L×W×H).

FIG. 1C: End elevation view of a stretchable loading chamber, partially in phantom, displaying non-limiting example dimensions.

FIG. 1D: Perspective view of a stretchable loading chamber.

FIG. 4A is a perspective view of the scaffold-stretching system.

FIG. 4B: Perspective view of a guiding sleeve of the scaffold-stretching system shown in FIG. 4A, partially in phantom.

FIG. 4C: Perspective view of the fixed plate of the scaffold-stretching system shown in FIG. 4A.

FIG. 4D: Perspective view of the movable plate of the scaffold-stretching system shown in FIG. 4A.

FIG. 4E: Perspective view of the coupling connecting the screw and the motor shaft of the scaffold-stretching system shown in FIG. 4A, partially in phantom.

FIG. 4F: Perspective view of a first ball nut holder of the scaffold-stretching system shown in FIG. 4A.

FIG. 4G: Perspective view of a ball screw shaft of the scaffold-stretching system shown in FIG. 4A.

FIG. 4H: Perspective view of a first bearing support of the scaffold-stretching system shown in FIG. 4A.

FIG. 4I: Perspective view of a second bearing support of the scaffold-stretching system shown in FIG. 4A.

FIG. 5A: Schematic of a scaffold-stretching system that includes a computer and a programmable controller.

FIG. 5B: Top view of the loading chambers of the scaffold-stretching system at rest (left) and during cyclic stretch (right).

FIG. 5C: Side elevation view showing the driving mechanism of the scaffold-stretching system at rest (top) and during cyclic stretch (bottom).

FIG. 6A: Cell viability—live cells are tagged green and dead cells are stained red. FIG. 6B: DNA quantification—the red dotted line represents the amount of DNA obtained from the initial cell seeding density. Results indicate that cells are viable and are proliferating within the scaffold. n=4.

FIG. 16A: Table 1, showing Ogden model parameter used for a silicone loading chamber.

FIG. 16B: Table 2, showing viscoelastic Prony series parameters used for collagen constructs.

FIG. 19A shows a schematic of the placement of embedded markers and deformation measurement through image-based analysis using ImageJ for experimental validation of the uniaxial tensile strain bioreactor. FIG. 19B shows a schematic of the boundary conditions applied in order to generate the Finite Element Model for characterizing the strain and stress profiles experienced by the 3D collagen constructs when subjected to mechanical loading using the uniaxial tensile strain bioreactor.

FIG. 20A shows a schematic of the major components involved during the operation of the bioreactor used in Example 2. A versatile and easy-to-use driver-controller system programmed through GUI-based software produces specified rotation of the high torque 2-phase stepper motor which in turn rotates the miniature ball-screw actuation system that translates into the reciprocal movement of the moving plate, resulting in the stretching of cellular collagen constructs within the silicone loading chamber. FIG. 20B shows experimentally-determined deformation undergone by the linear region of the silicone loading chamber groove and collagen construct at the ends (0 mm and 25 mm) and center (12.5 mm) at applied loads of 1N, 2N, and 3N. No significant difference seen between the deformation values obtained for silicone and collagen indicates that the applied load is being transferred effectively to the 3D collagen construct.

FIG. 21A shows FEM-predicted longitudinal tensile strain profiles along the length of the collagen construct. FIG. 21B shows a schematic of the direction of measurements of length (a to b), width (e to f), and thickness (g to h) across the collagen construct. The distance of (c) to (d) defines the homogenous tensile strain region. FIG. 21C shows longitudinal tensile strain profiles across the width, and FIG. 21D shows the thickness of the collagen construct at applied loads of 1N, 2N, and 3N. Strain experienced by the collagen construct is homogenous over the region of 15×4×2 mm of the construct that is around 60% of the effective region of characterization. The applied loads of 1N, 2N, and 3N correspond to 2%, 4%, and 6% linear strains.

FIG. 23A shows strain distribution profiles generated by the bioreactor at loading frequencies of 0.1 Hz, 0.2 Hz, 0.6 Hz, 0.8 Hz, and 1 Hz across the length of the construct for an applied load of 2N. No significant difference seen in the strain magnitudes with change in loading frequencies. FIG. 23B shows a comparison of profiles at Cycle 1 vs Cycle 40 during cyclic loading of collagen constructs at 0.5 Hz loading frequency in terms of longitudinal tensile strain, and FIG. 23C shows von Mises stress, across its length at applied loads of 1N, 2N, and 3N. The strain and stress profiles smoothen out at the ends with progression in cycle numbers, and the magnitude of both stresses and strains in the region of homogenous strain remain fairly constant.

FIG. 24A shows loaded (2% strain, 0.1 Hz, 1 hour/day) and unloaded 3D collagen constructs encapsulated with OB6, C2C12, or AC10 cells that were visualized under confocal microscope at day 3. Green color represents live cells while red indicates dead cells. Scale bar is 100 µm. FIG. 24A also shows Table 3, displaying a quantification of viable cell numbers from the live-dead assay images. FIG. 24B shows DNA quantification of loaded and unloaded cells-seeded inside collagen constructs at day 3 using a PicoGreen assay. The red dotted line represents the initial cell density within the scaffolds. The results show no significant differences in either the cytotoxicity or the cell proliferation of loaded constructs compared to the control.

DETAILED DESCRIPTION

Figure 1B:
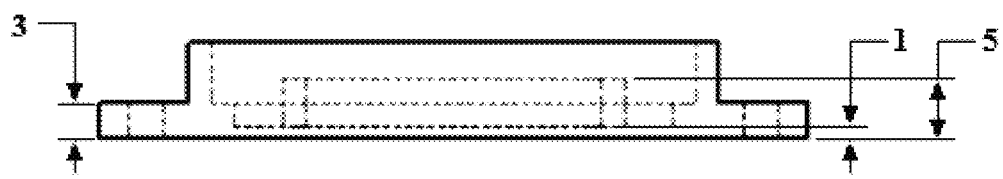
Figure 1C:
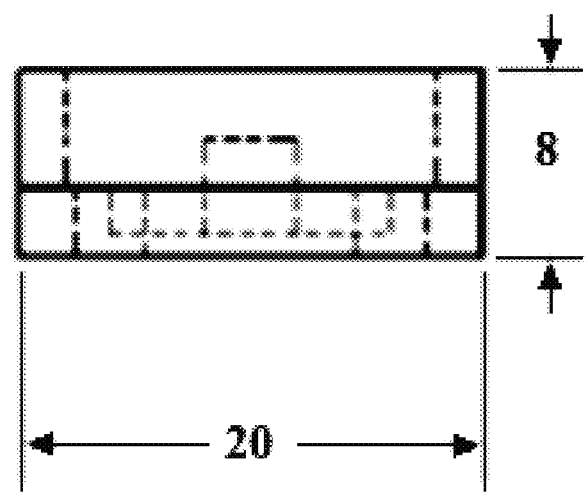

Throughout this disclosure, various publications, patents and published patent specifications are referenced by an identifying citation. The disclosures of these publications, patents, and published patent specifications are hereby incorporated by reference into the present disclosure to more fully describe the state of the art to which this invention pertains.

Described herein is a scaffold-stretching system (also referred to herein as a uniaxial tensile strain bioreactor or a loading platform) for applications of cyclic and static uniaxial tensile mechanical loading on cellular three-dimensional scaffolds, such as human skin substitutes, to mimic the in vivo environment of musculoskeletal, cardiovascular, and other tissues that experience uniaxial strains on a daily basis. Operating the scaffold-stretching system at a wide range of frequencies and strains allows the scaffold-stretching system to mimic any tissue of interest and elucidate the signaling mechanisms undergone at physiological state, acute and chronic injuries, as well as healing and rehabilitation phases. The scaffold-stretching system can also help align the scaffold matrixes and create engineered substitutes for tissue regeneration.

In general, the scaffold-stretching system includes one or more stretchable loading chambers that define one or more grooves for securely holding the scaffold in place. The groove is configured to hold (e.g., for depositing) one or more scaffolds. The stretchable loading chamber has a design such that the strain transfer from the substrate to the scaffold is maximized. In some embodiments, the stretchable loading chamber ensures 85-90% strain transfer from the stretchable loading chamber to the scaffold when subjected to physiological strain values.

The scaffold can include any cell-embedded matrix system, such as human skin substitute. The scaffold retains its integrity even over extended periods of loading at various physiological strains and frequency values with the groove of the stretchable loading chamber securely holding the scaffold in place. The stretchable loading chamber can also act as a culture chamber, which eliminates any handling required of the scaffold itself. That is, when the stretchable loading chamber is used as a culture chamber, there is no need to transfer the scaffold from a culture medium into the mechanical loading apparatus. In such embodiments, a well in the stretchable loading chamber houses sufficient culturing media for cell survival, proliferation, and differentiation.

In some embodiments, a stretchable loading chamber is composed of silicone. Silicone polymer is a useful choice as the material for the stretchable loading chamber due to its various favorable characteristics: robustness; bio-inert; biocompatible; easy to sterilize (autoclave); cost effective; easy to use; provides flexibility in the shape and size of chamber required; highly elastic; high tensile strength; solidifies on polymerization; and can be poured into a mold of desired shape and size, thus providing flexibility in chamber design. However, it is understood that other materials may be used for making the stretchable loading chamber.

The stretchable loading chambers can be made in a convenient and cost effective manner. In one non-limiting example of making a stretchable loading chamber, a silicone solution is poured into a mold, and allowed to cure. Thus, the design of the stretchable loading chamber and/or grooves in the chamber can be modified if necessary by just changing the mold pattern. Further, the stretchable loading chambers are easy to sterilize by autoclaving.

In the scaffold-stretching system, or uniaxial tensile strain bioreactor, the stretchable loading chambers are supported by a driving mechanism (mechanical and/or electrical system) which provides a uniaxial stretching to the stretchable loading chambers. In one embodiment, the driving mechanism includes a ball-screw that can be driven by a 2-phase high torque stepper motor which, in turn, is connected to a programmable controller. The driving mechanism produces a precise and controlled linear uniaxial motion, and the driving mechanism can be operated at a wide range of loading strains and frequencies. One or more of the components of the driving mechanism and/or the high tensile strength of the material comprising the stretchable loading chamber can be altered in order to achieve a desired stretching of the scaffold. For example, as further explained herein, the length of the guiding sleeve can be altered, and the capabilities of the ball screw mechanism and/or the high torque stepper motor driven can be altered by varying the GUI (graphic user interface)-based programmable controller. The broad range of the strain and frequency values makes the scaffold-stretching system capable of mimicking any phase of a human tissue, including physiological, acute, and chronic injuries, and healing and rehabilitation.

Different types of loading regimes can be applied, such as static and symmetric/asymmetric cyclic, with the capability of inserting rest periods and ramping up strain and frequency with duration of loading.

The scaffolds do not need to be clamped for mechanical loading, thus eliminating stress concentration at the ends due to gripping effect. Since no gripping is required, there is no risk of disintegration of mechanically fragile scaffolds during the fixation process. However, it is possible to clamp the scaffolds if desired, though such clamping may result in sub-optimal results.

The loading platform is capable of applying uniaxial strains to any material that can withstand tensile loads and that can be polymerized into the stretchable loading chamber. In certain non-limiting embodiments, the scaffold can comprise one or more of: hydrogels, including natural polymer-based hydrogels such as collagen, alginate, chitosan, hyaluronic acid, fibrin, gelatin, and Matrigel; synthetic hydrogels such as polyethylene glycol and polylactic acid, as well as blends of two or more hydrogels (hybrid material). The choice of scaffold material can depend on the tissue being cultured. Further, the hydrogels can be tuned to have the desired amount of mechanical strength, porosity, and tensile properties that suits a specific tissue. For ease of explanation, reference to the "scaffold" herein may be referring to the scaffold material together with the cells/tissue being cultured in the stretchable loading chamber.

In one embodiment, the scaffold-stretching system is composed of a culture chamber loaded with human skin substitutes (HSS). The scaffold-stretching system includes a stretchable loading chamber that also acts as a culture chamber, and a computer-controlled mechanical loading apparatus, onto which human skin substitutes (HSS) can be cultured and tested for cosmetic skin care products. The HSS can be created using collagen and human keratinocytes within the culture chamber, and can mimic wrinkled or stretched skin conditions by virtue of the mechanical loading apparatus. Alternatively, embodiments of the scaffold-stretching system for use with HSS can utilize commercially available HSS, such as EpiSkin.

Advantageously, the scaffold-stretching system can mimic wrinkled or stretched skin conditions on HSS using the mechanical loading apparatus. Mimicking real skin conditions (wrinkle or stretched) enables the scaffold-stretching system to be used in skin care cosmetic testing. The stretchable loading chamber accommodates HSS with a larger surface area of substrates for conducting testing, and mimics wrinkled or stretched skin configuration. This offers a solution for the limitations in skin care cosmetic testing platforms, and offers unique testing features which are not currently available. This addresses the limitations of currently existing skin care cosmetic testing methods by offering an in vitro HSS testing platform with customized size and physiologically relevant testing modalities. The scaffold-stretching system can use in vitro HSS so as to eliminate the efficacy and toxicity results, inconsistencies, and ethical concerns associated with ex vivo (dead) animal skin tissue and human tissue. The scaffold-stretching system also offers great flexibility in size of the HSS, unlike commercially available reconstructed human epidermis (RHE). Commercially available HSS only offer 0.63 $cm^2$ effective surface area for testing, which is very limited for skin and body care cosmetic products. One non-limiting example scaffold-stretching system described herein, however, can offer 10 $cm^2$ of effective surface area HSS for testing, which is almost 15 times more than commercially available HSS. In addition, this testing platform can mimic native skin conditions through stretching HSS with pre-defined strain values using a computer-controlled mechanical loading apparatus. Mimicking stretched native skin using HSS is a unique approach in skin care cosmetic testing platforms. This feature provides relevant efficacy and toxicity results, and accelerates the product development cycle time.

To create HSS, primary human epidermal keratinocytes can be purchased from a suitable source, such as ATCC (ATCC® PCS-200-011), and cultured in DMEM medium supplemented with 10% Fetal Bovine Serum and 1% Penicillin-Streptomycin. Upon confluency, the HSS are trypsonized and split into 1:5 ratio to populate them until further usage. The populating process continues until reaching a total number of 250 million cells. In one non-limiting example, collagen type-I solution at 4.41 mg/ml concentration and pH ~3-4 is diluted to 3 mg/ml concentration and neutralized with chilled 1 N NaOH along with phosphate buffer saline (PBS). The neutralized collagen is poured into the culture chamber and incubated overnight for next-day keratinocyte incorporation.

Keratinocytes are incorporated on the collagen-coated culture chamber for HSS creation. Populated primary human epithelial keratinocytes are seeded on the collagen-coated silicon chamber with 5×10$^6$ cells/$cm^2$ cell seeding density and incubated at 37° C. and 5% $CO_2$ conditions for 30 days by air-liquid (DMEM medium) interface culture to obtain fully epithelial differentiation. Epithelial differentiation can be further confirmed by checking the expression of three epithelial associated genes using real-time polymerase chain reaction (RT-PCR). For gene expression analysis, total RNA from cells can be extracted using an RNeasy mini kit. 1 µg of RNA can be reverse transcribed to cDNA, for example, using a QuantiTect Reverse Transcription Kit. PCR amplification can be performed, for example, in an iCycleriQ detection system (Biorad) with thermocycling performed for 10 minutes at 95° C. followed by 40 cycles at 95° C. for 15 seconds and 56° C. for 60 seconds. For epithelial differentiation gene expression of cytokeratin 18, occludin, and tight-junction protein can be measured. The primer sequences can be designed by verified using OligoAnalyzer. Hydroxymethylbilane synthase (HMBS) can be used as a house-keeping gene to normalize the expression of cytokeratin 18, occludin, and tight-junction protein. The gene expression of cytokeratin 18 should be around 50-fold higher, while occludin and tight-junction protein's expressions should be 10-fold higher than the house-keeping gene to confirm the epithelial differentiation. The epithelial differentiation confirms that human skin substitute (HSS) is ready for further analysis.

The quality of the produced HSS can be validated through various methods, such as through cell viability and a barrier function analysis (BFA). Cell viability can be measured using a MTT assay. In one non-limiting example, HSS is incubated with 300 µl of MTT solution for 3 hours and an additional 2 hours after 2 mL isopropanol. Then, 250 µl extraction solution is transferred to a well plate to measure absorbance (OD values) at 570 nm wavelength using a microplate reader (SOFTmax Pro). Based on OECD and EVCAM guidelines for cell viability in HSS, quality acceptance criterion in MTT reduction assay is OD greater than or equal to 0.8. If MTT reduction OD value is below OD 0.8, then the initial cell seeding density number is increased and the HSS can be supplemented with media having an additional 10% FBS.

The barrier function of the HSS can be tested according to the property of the very top layer of HSS to resist the rapid penetration of cytotoxic chemicals. The barrier function is quantified by measuring the time required to reduce the cell viability by 50%, which is also called ET-50. In one non-limiting example of barrier function analysis, HSS is exposed with cytotoxic 1% Triton X-100 for 0, 1, 3, 5, 7, and 10 hours, and the cell viability is counted with an MTT assay after each incubation time. The incubation time killing 50% of the cells is considered as ET-50. Based on OECD and ECVAM guidelines for acceptable barrier function, the ET-50 value should be between 4 hours to 10 hours. If the measured ET-50 value is below the 4 hour threshold, then the cell seeding density is increased to increase the thickness of the very top layer of HSS. If ET-50 is above 10 hours, then the cell density is decreased until ET-50 is in the range of 4 hours to 10 hours.

Cell viability and barrier function are important properties for HSS to be used in skin care cosmetic testing, and they are commonly used in the cosmetic industry. Once HSS is created and validated, the culture chamber with HSS is mounted on the computer-controlled mechanical loading apparatus to apply pre-defined stretch and compression to mimic stretched and wrinkled skin. As one non-limiting example, to mimic stretched and wrinkled skin, a 2% stretch and compression is applied to the culture (i.e., stretchable loading) chamber. A firming testing protocol, which is used in the cosmetic industry to test cosmetic product efficacy, can be employed. However, other methods of testing skin can products can be utilized.

In firming testing, the skin care product is applied to the substrate, and the substrate is collected for molecular analysis. In one non-limiting example, the skin care product is applied on wrinkled and stretched HHS topically. The HSS is collected at 3 hours, 12 hours, and 24 hours following the topical application for measuring gene expression of collagen synthesis, elastin, matrix metalloproteinases (MMPs), fibronectin, laminin. At each time point, four HSS (n=4) are ideally used for gene expression analysis, however other numbers of samples can be used. At the characterizations stage, the HSS is washed using PBS and total RNA from cells are extracted using the RNeasy mini kit. 1 μg of RNA are reverse transcribed to cDNA using the QuantiTect Reverse Transcription Kit. PCR amplification can be performed in iCycleriQ detection with thermocycling performed for 10 minutes at 95° C. for 15 seconds and 56° C. for 60 seconds. The primer sequences can be designed and verified using OligoAnalyzer. Hydroxymethylbilane synthase (HMBS) can be used as a house-keeping gene to normalize the expression of collagen synthesis, elastin, matrix metalloproteinases (MMPs), fibronectin, and laminin.

Alternatively, other kinds of tests may be conducted, such as where a product is applied to HSS before the HSS is wrinkled and stretched.

Any type of skin care cosmetic product can be tested in the scaffold-stretching system described herein. Non-limiting examples of types of skin care cosmetics for testing in the scaffold-stretching system include face moisturizers, foot powders and sprays, face and neck creams or lotions, face washes and cleansers, body and hand creams and lotions, face masks, anti-aging creams, eye care creams, face serums, lip balms, exfoliants, and the like.

Figure 1D:
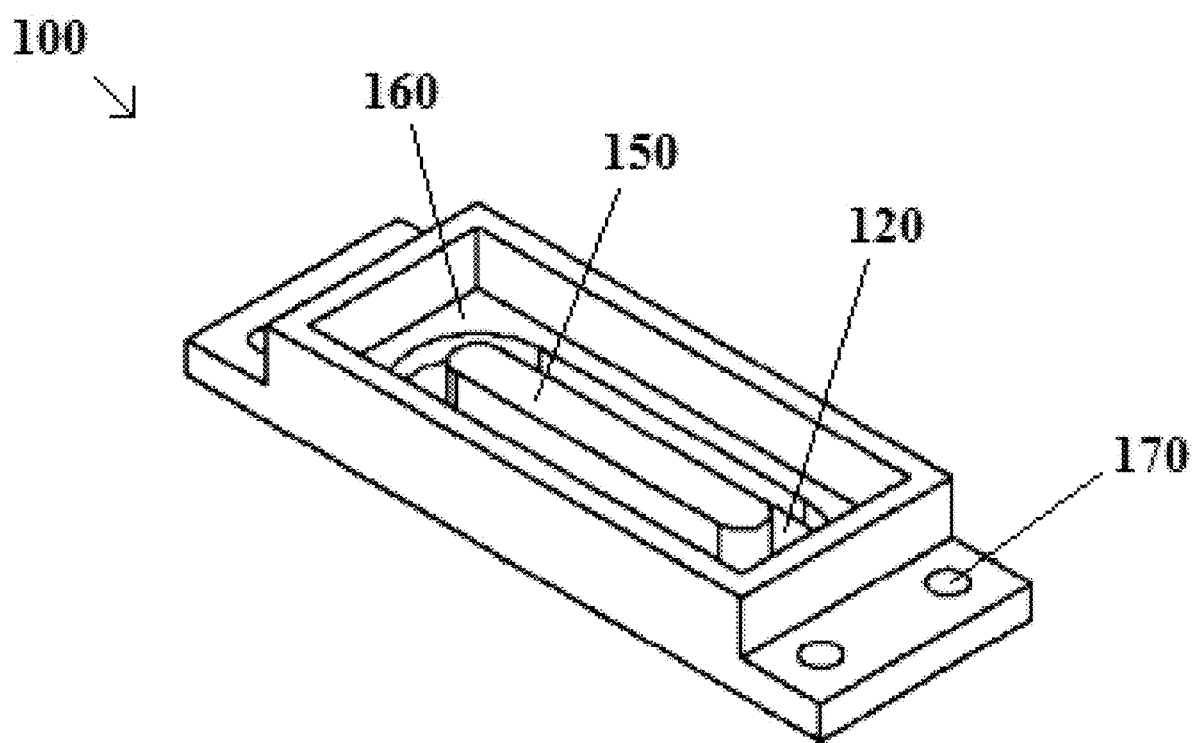

Referring now to the figures, where like reference numbers in different embodiments indicate similar structure, FIGS. 1A-1D show an embodiment of a stretchable loading chamber 100. The cellular gel-based scaffold 110, illustrated in dark grey in FIGS. 1A-1B, is added into the groove 120 within the stretchable loading chamber 100. In the embodiment shown in FIGS. 1A-1D, the groove 120 is composed of two opposing linear portions 130 that are connected at opposing ends by two semicircular portions 140. In this embodiment, the geometry of the stretchable loading chamber 100 is designed to increase the strain transfer from the stretchable loading chamber's material (e.g., silicone) to the scaffold 110 by minimizing the sliding of the scaffold 110 with respect to the silicone material during the mechanical loading being applied to the stretchable loading chamber 100 and to the scaffold 110 within the groove 120 in the stretchable loading chamber 100. It is to be understood that single linear portions 130 of the scaffold 110 placed on the base of the chamber 100 alone risk not being stretched along with the silicone, which would then translate into low strain values within the construct. However, as shown in this embodiment, the groove 120, which is best seen in FIG. 1D, allows the scaffold 110 to be securely held from both sides. The semi-circular portions 140 connect the linear portions 130 so that the scaffold 110 stretches in the direction of load when subjected to loading by providing mechanical support and stability. In this embodiment, an island or inner portion 150 (also best seen in FIG. 1D) in the middle of the stretchable loading chamber 100 provides for opposing linear portions 130 not coming close together while in motion; rather, the opposing linear portions 130 of the scaffold 110 are stretched along with the stretchable loading chamber 100. The groove 120 and island 150 are enclosed in a well 160 (also best seen in FIG. 1D) to hold a desired culture medium required for the cells to survive, proliferate, and differentiate. The well 160 is flanked by flaps having two holes 170 on each side through which one or more holding pins from a supporting base connected to the driving mechanism is inserted in order to produce stretching of the silicone loading chamber 100, as described in more detail below.

In the embodiment shown, the thickness and width of the scaffold 110 are kept sufficiently small so that there is not a significant difference in strain contours along those axes, rendering the strain applied predominantly uniaxial along the axis of application of load. In one non-limiting example, the thickness is about 2 mm, and the width is about 4 mm.

With this configuration, there can be an increased strain transfer from the stretchable loading chamber 100 to the scaffold 110. At the same time, this configuration eliminates the necessity of grips to hold the scaffold 110, thus negating stress concentration on either side. Also, since the scaffolds 110 are generally cultured in the chamber 100 itself, there are no procedures required for transferring the scaffolds 110 from a culture chamber to the stretchable loading chambers 100, thus minimizing the handling labor, time, possible scaffold damage, and risk of contamination.

It is to be understood that various methods may be used to make the stretchable loading chamber 100. In the embodiment shown in FIGS. 1A-1D, a corresponding mold in aluminum (or other suitable mold material) can be made to fabricate the silicone loading chambers. As a non-limiting example, Dragon Skin® 10 High Performance Silicone rubber components A and B can be mixed in a 1:1 ratio, poured into the mold, and allowed to cure overnight to obtain a stretchable loading chamber 100.

Figure 2A:
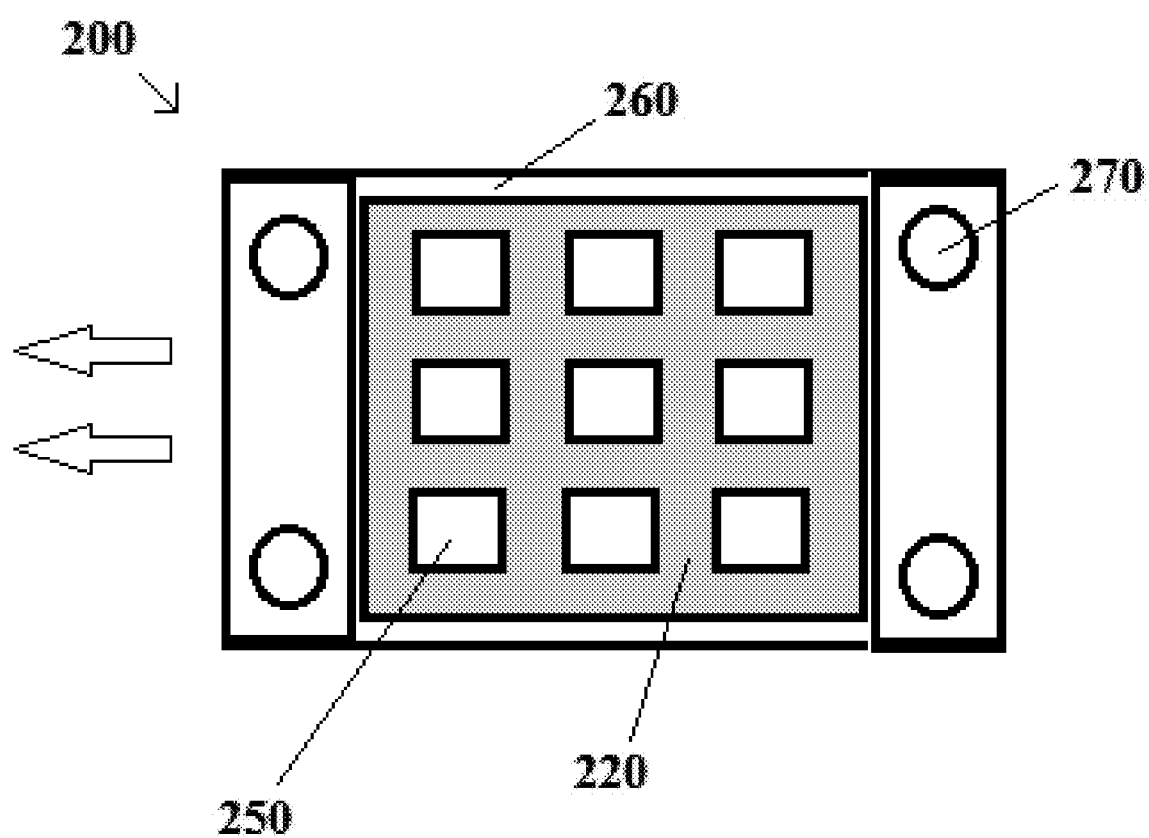
FIG. 2A: Top view of another embodiment of a stretchable loading chamber, with a groove for holding the scaffold shown in grey.

FIG. 2A shows another embodiment of a stretchable loading chamber 200, configured to stretch in the direction indicated by the arrows. A cellular gel-based scaffold 210 is added into the groove 220 within the stretchable loading chamber 200, represented as dark grey. In the embodiment shown in FIG. 2A, the groove 220 is composed of interconnected portions in a grid-like pattern that are connected at opposing ends. In this embodiment, the geometry of the stretchable loading chamber 200 is designed to allow the scaffold 210 within the grooves 220 to have a mesh-like configuration that can be used, for example, for skin and/or cardiac patches. Islands 250 and the groove 220 are enclosed in a well 260 to hold a desired culture medium required for the cells to survive, proliferate, and differentiate. The stretchable loading chamber 200 includes pin holes 270 for connection to a supporting base or other components of a scaffold-stretching system, such as fixed or moving plates, as described in more detail below.

Figure 2B:
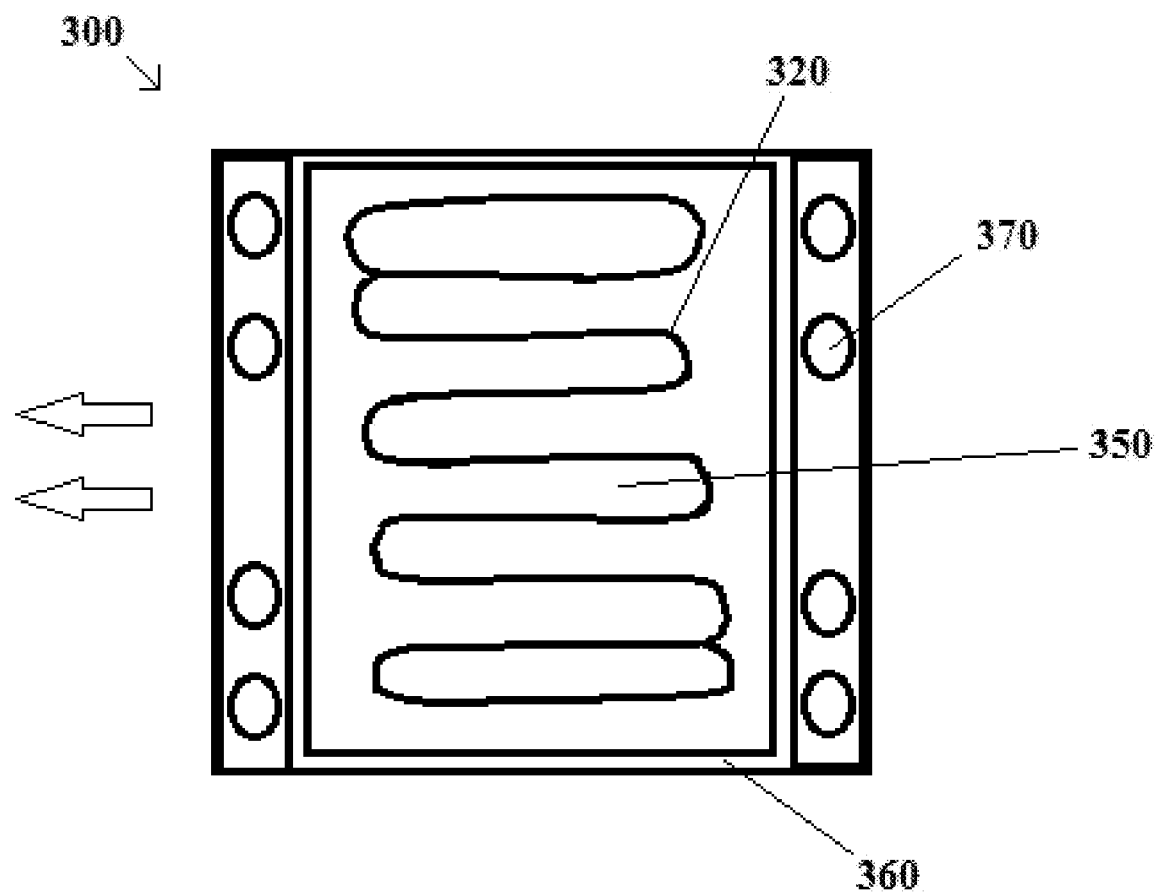
FIG. 2B: Top view of another embodiment of a stretchable loading chamber, with an alternatively shaped groove, having a sinusoidal pattern, for holding the scaffold.

FIG. 2B shows another embodiment of a stretchable loading chamber 300, configured to stretch in the direction indicated by the arrows. A cellular gel-based scaffold 310 is added into the groove 320 within the stretchable loading chamber 300. In the embodiment shown in FIG. 2A, the groove 320 is composed of interconnected portions in a sinusoidal pattern. In this embodiment, the geometry of the stretchable loading chamber 300 is designed to allow the scaffold 310 within the grooves 320 to mimic blood vessels, such as, for example, a hepatic portal system. Islands 350 and the groove 320 are enclosed in a well 360 to hold a desired culture medium required for the cells to survive, proliferate, and differentiate. The stretchable loading chamber 300 includes pin holes 370 for connection to a supporting base or other components of a scaffold-stretching system, such as fixed or moving plates, as described in more detail below.

Thus, by changing the shape, configuration and/or number of grooves and/or islands, it is possible to have different stretchable loading chamber designs that can be used to suit the desired tissue engineering application.

Figure 3:
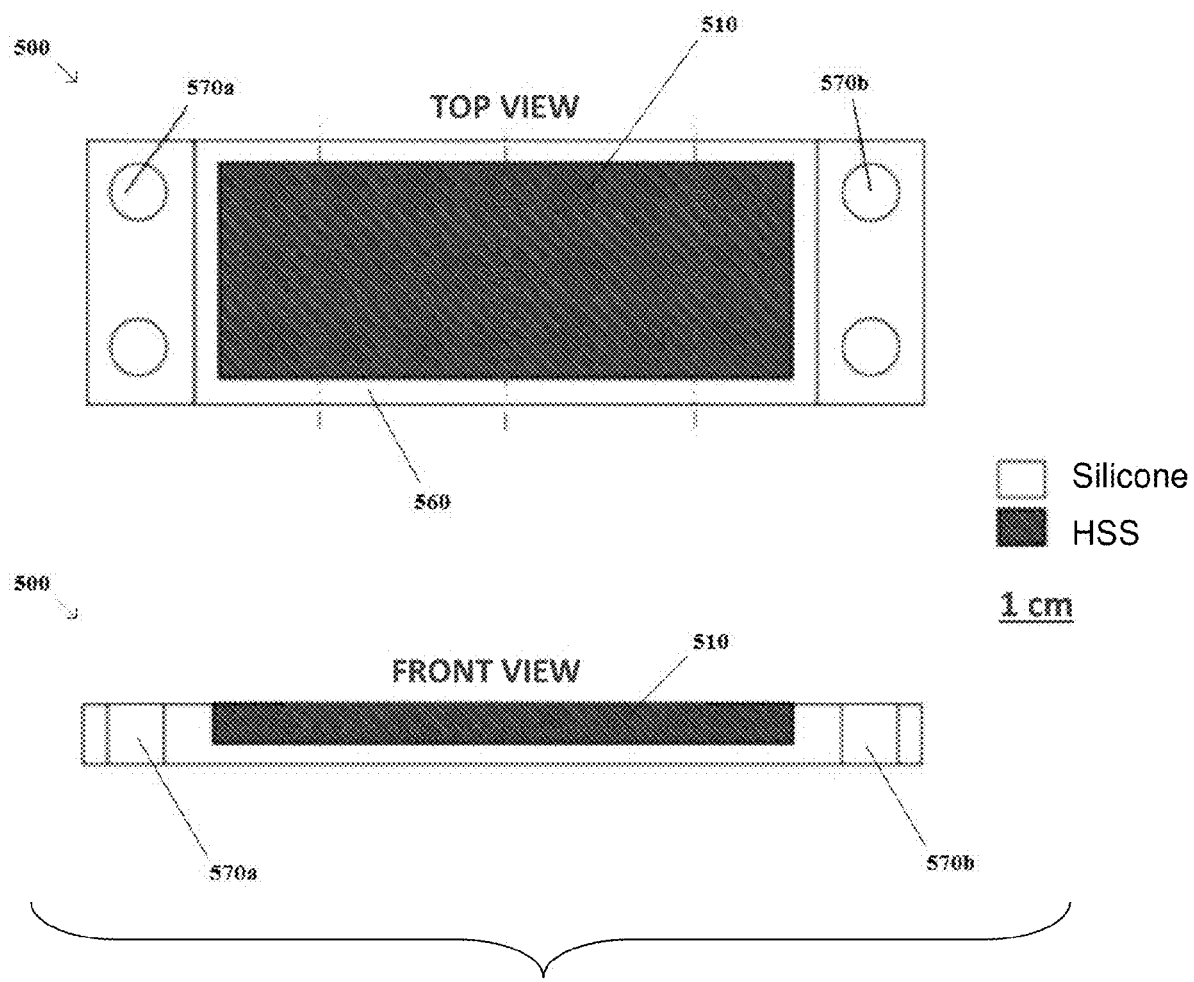
FIG. 3: Schematic illustrations of a top and side (or front) view of an embodiment of a stretchable loading chamber.

FIG. 3 shows another embodiment of a stretchable loading chamber 500. In this embodiment, the scaffold 510 includes human skin substitute (HSS), illustrated as dark grey. The stretchable loading chamber 500 may include cell culture media and may be used as a culture chamber. The chamber 500 includes pin holes 570a configured to attach the stretchable loading chamber 500 to a fixed plate, and pin holes 570b configured to attach the stretchable loading chamber 500 to a moving plate, as described in more detail below. The scaffold 510 is enclosed in a well 560 to hold a desired culture medium required for the HSS cells to survive, proliferate, and differentiate. In this non-limiting example embodiment, the stretchable loading chamber 500 is made from silicone.

FIGS. 4A-4I are schematic illustrations of a scaffold-stretching system 402 where a mechanical loading system is configured to apply uniaxial tensile strains on the three-dimensional gel-based scaffolds 410 seeded within silicone loading chambers 400. In the embodiment shown, four silicone loading chambers 400 are placed on a base composed of two polycarbonates plates, a fixed plate 408 and a movable plate 412. The fixed plate 408 has eight aluminum pins 409 fitted at one end. Similarly, the movable plate 412 has eight aluminum pins 413 fitted at one end. Though aluminum is described for exemplary purposes, it is understood that the pins 409, 413 can be made from other materials. Regardless of the pin material, the stretchable loading chambers 400 each have corresponding pin holes 470 which allow the ends of the stretchable loading chambers 400 to be slid over the corresponding pins 409, 413, and to secure the chamber 400 to the fixed and movable plates 408, 412.

Figure 4A:
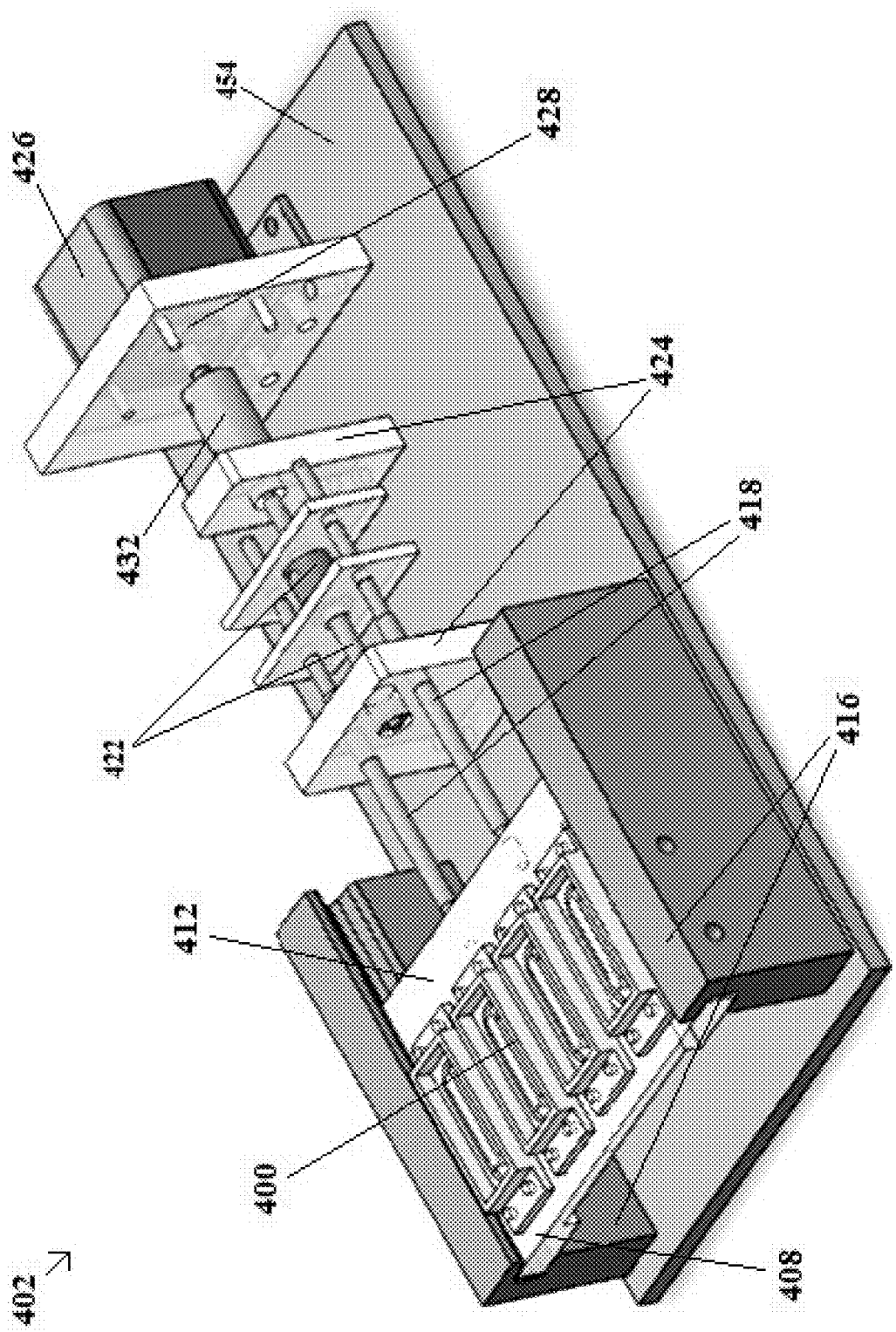
FIGS. 4A-4I: Schematics of an embodiment of a scaffold-stretching system for applying uniaxial tensile strains on a three-dimensional gel-based cellular scaffold seeded within specially designed silicone loading chambers.
Figure 4B:
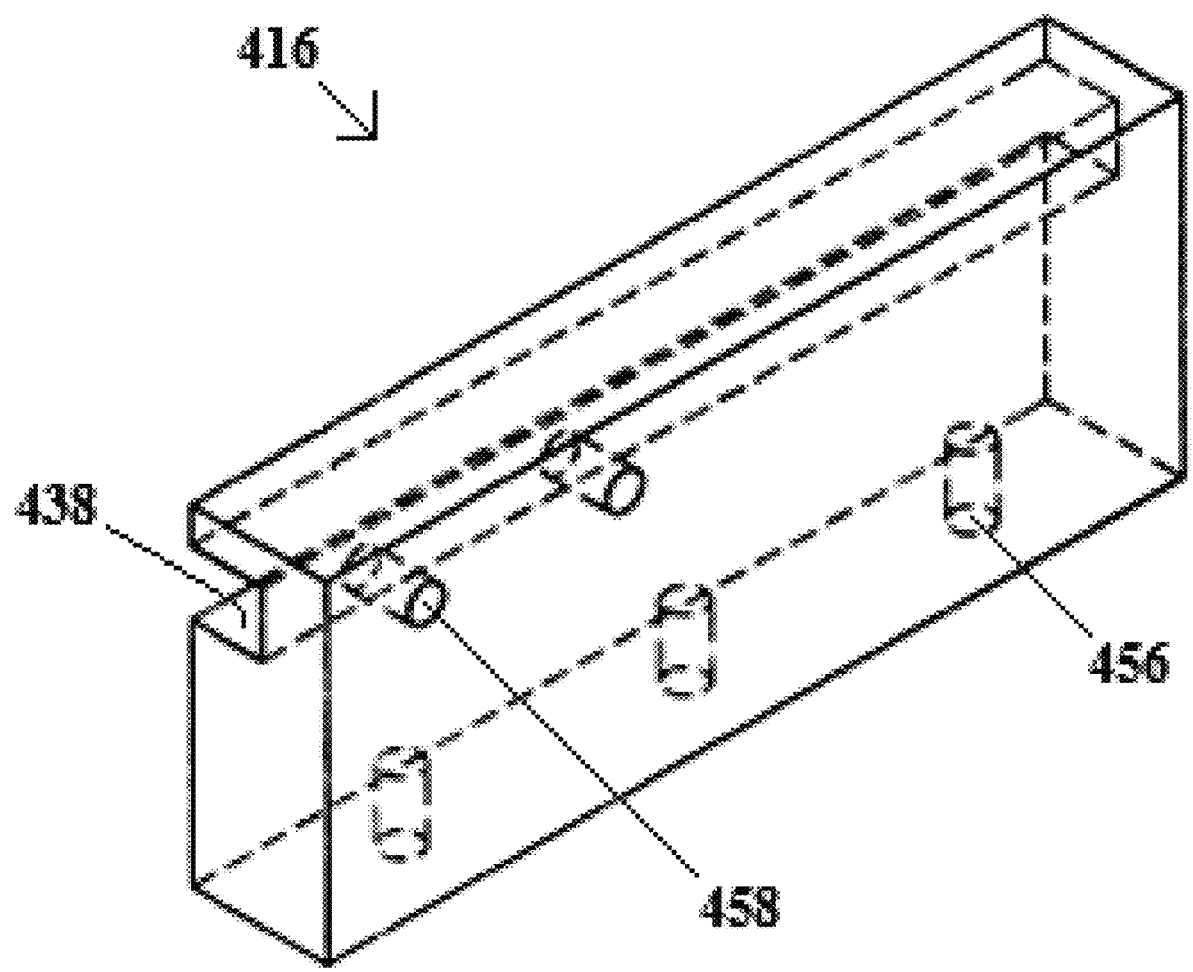
Figure 4C:
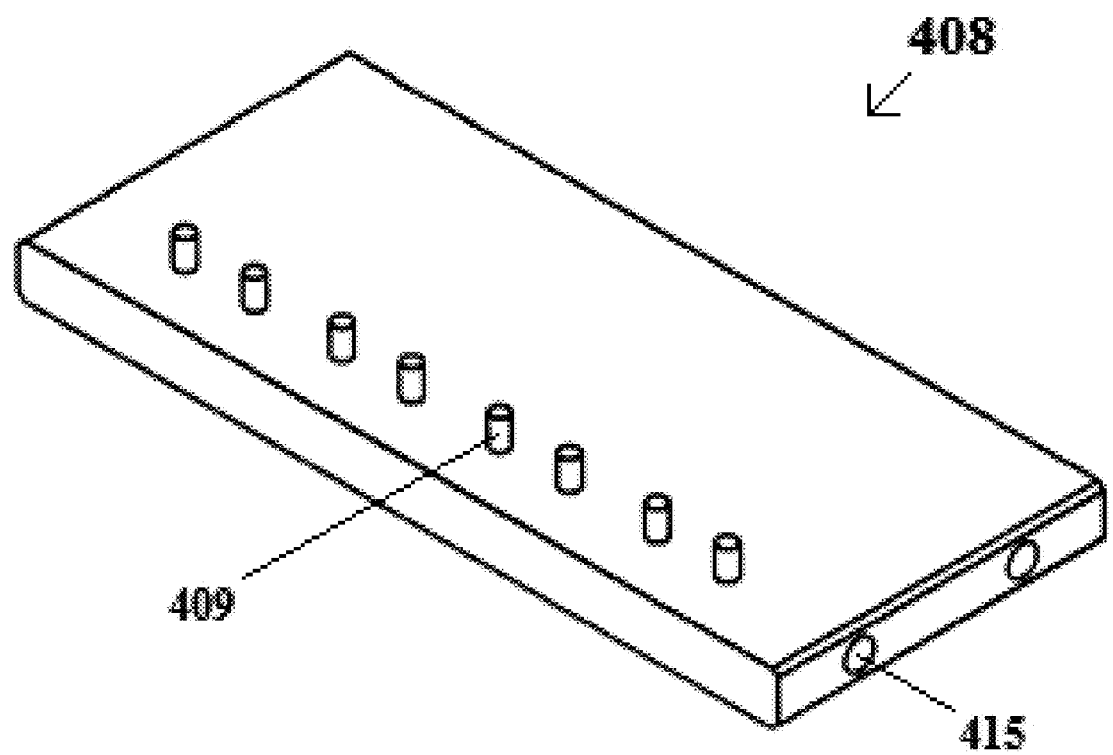

The fixed plate 408, depicted in FIG. 4C, provides a base for the stretchable loading chambers 400, and helps to support the weight of the stretchable loading chambers 400 loaded with scaffold 410 and media during mechanical loading. The movable plate 412, on the other hand, is primarily responsible for transmitting motion provided by the driving mechanism to the stretchable loading chambers 400. In the embodiment shown, there is a 2 mm gap between the fixed plate 408 and the movable plate 412. The gap prevents the fixed and movable plates 408, 412 from knocking against each other during cyclic motion. The fixed and movable plates 408, 412 are slidingly supported by opposing polycarbonate guiding sleeves 416 on either side to allow the translational motion of the movable plate 412, while the fixed plate 408 is held in place by inserting pins 458 from the guiding sleeves 416 into the screw holes 415 of the fixed plate 408.

The inner surfaces 438 of each guiding sleeve 416 are given a smooth finish that causes minimal friction and abrasion while the movable plate 412 is in motion. The length of the guiding sleeves 416 can be determined such that the movable plate 412 can be pulled up to strain values that would cover the entire range of physiological loading regimes, determined in terms of the uniaxial elongation of the linear part of the groove of the stretchable loading chamber 400.

Figure 4D:
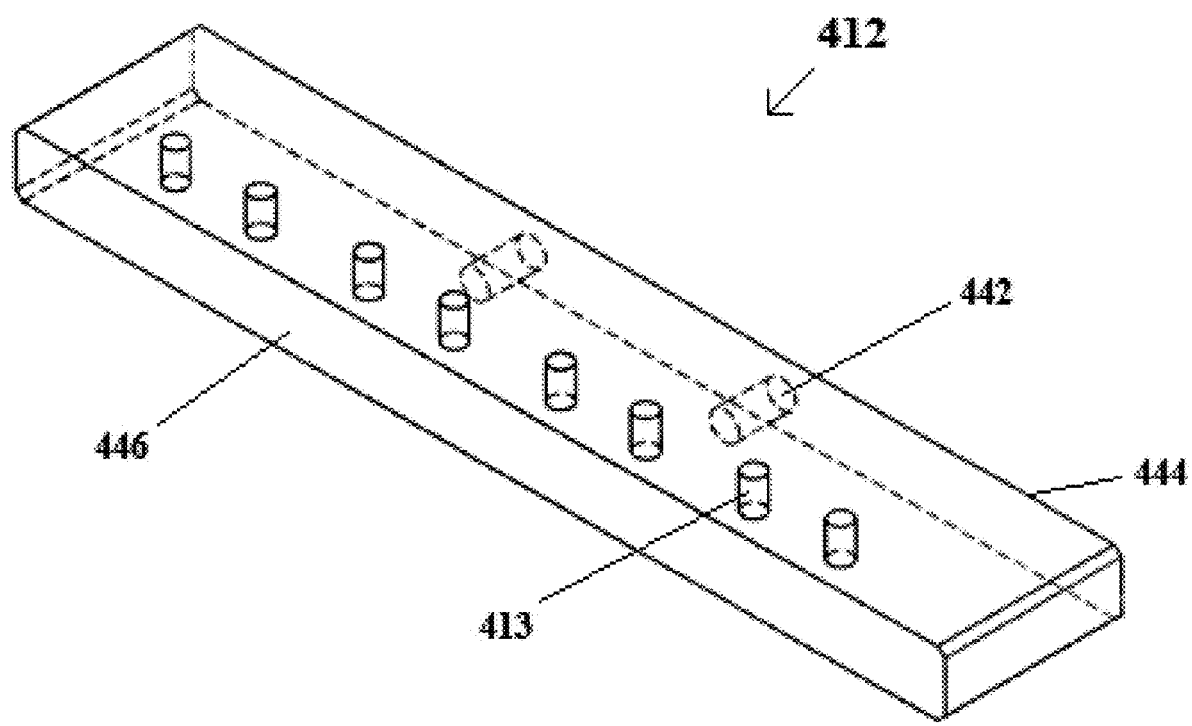
Figure 4E:
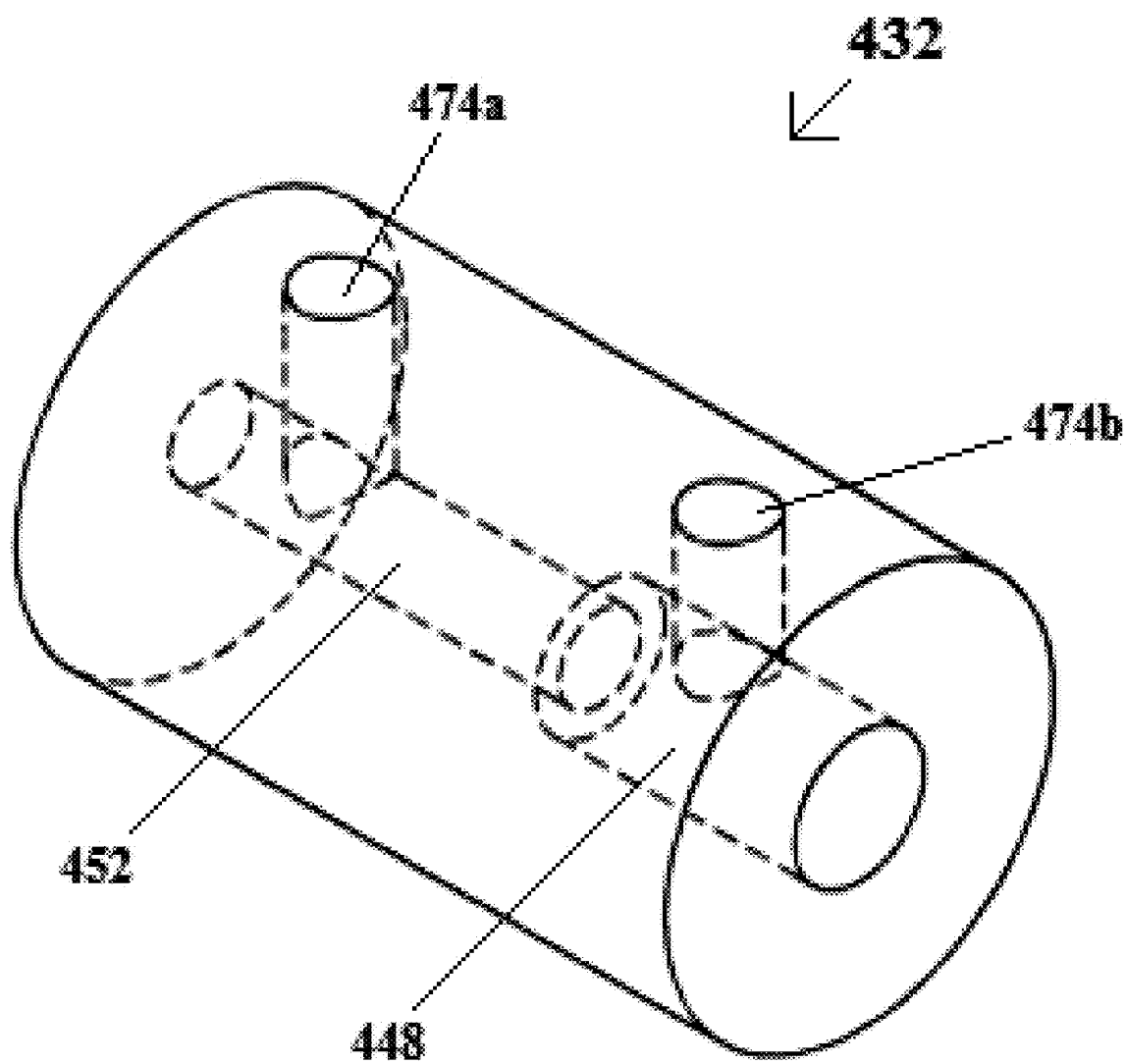

The movable plate 412, depicted in FIG. 4D, has a free end 444 and a chamber-abutting end 446, with the free end 444 being the side of the movable plate 412 opposite the side which abuts the stretchable loading chambers 400. Two connecting rods 418 are screwed into screw holes 442 in the free end 444 of the movable plate 412 and are used to transfer the motion from the driving mechanism to the stretchable loading chambers 400 via the movable plate 412. The connecting rods 418 transfer motion to the movable plate 412 which, in turn, transfers the motion to the stretchable loading chambers 400 mounted on the movable plate 412 via pins 409.

Figure 4F:
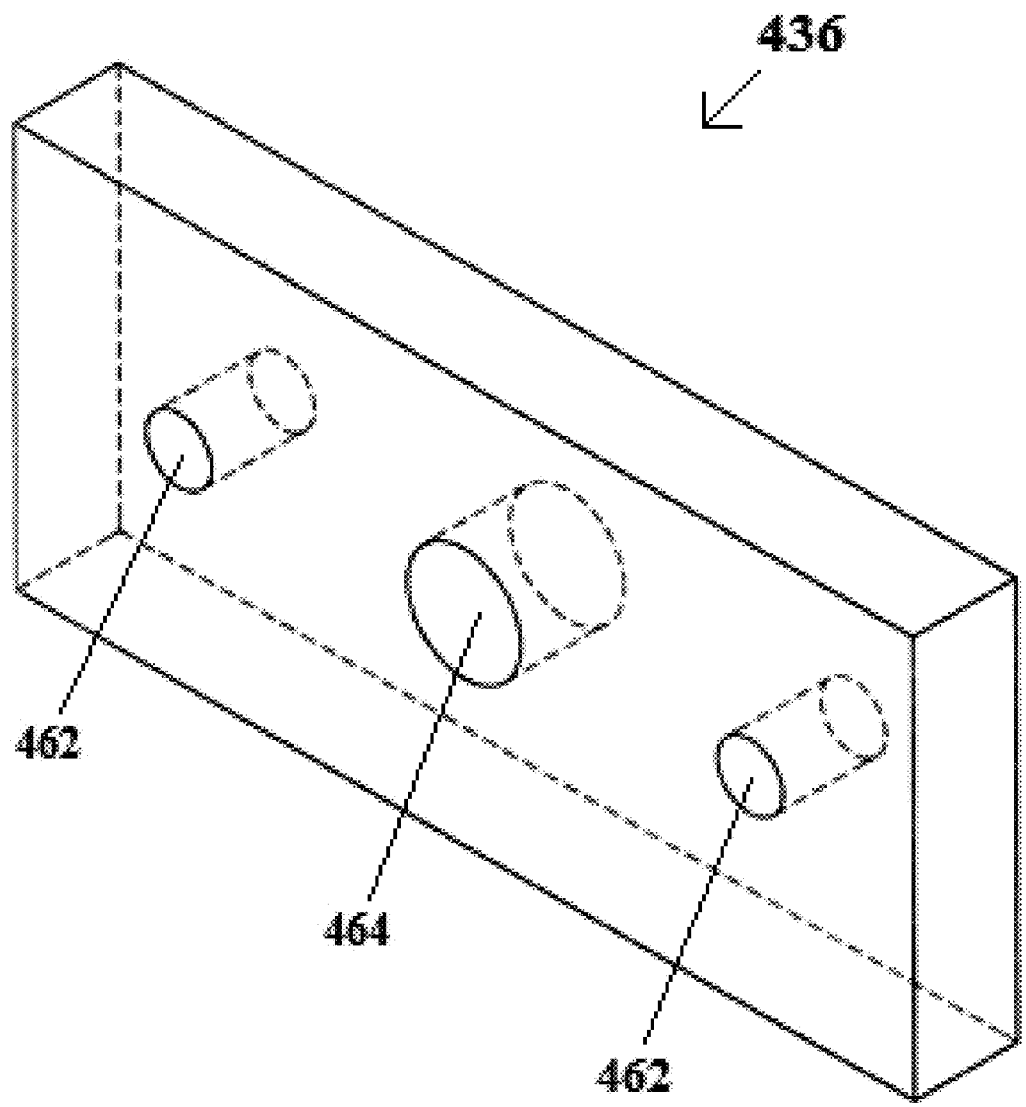
Figure 4G:
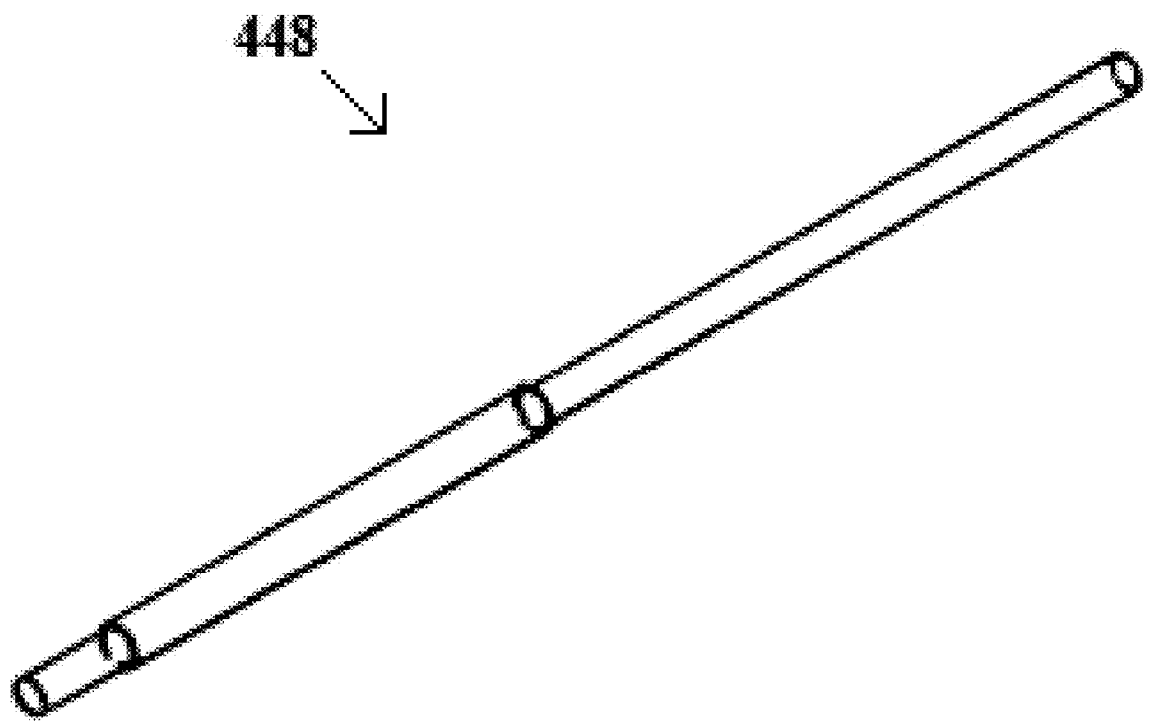
Figure 4H:
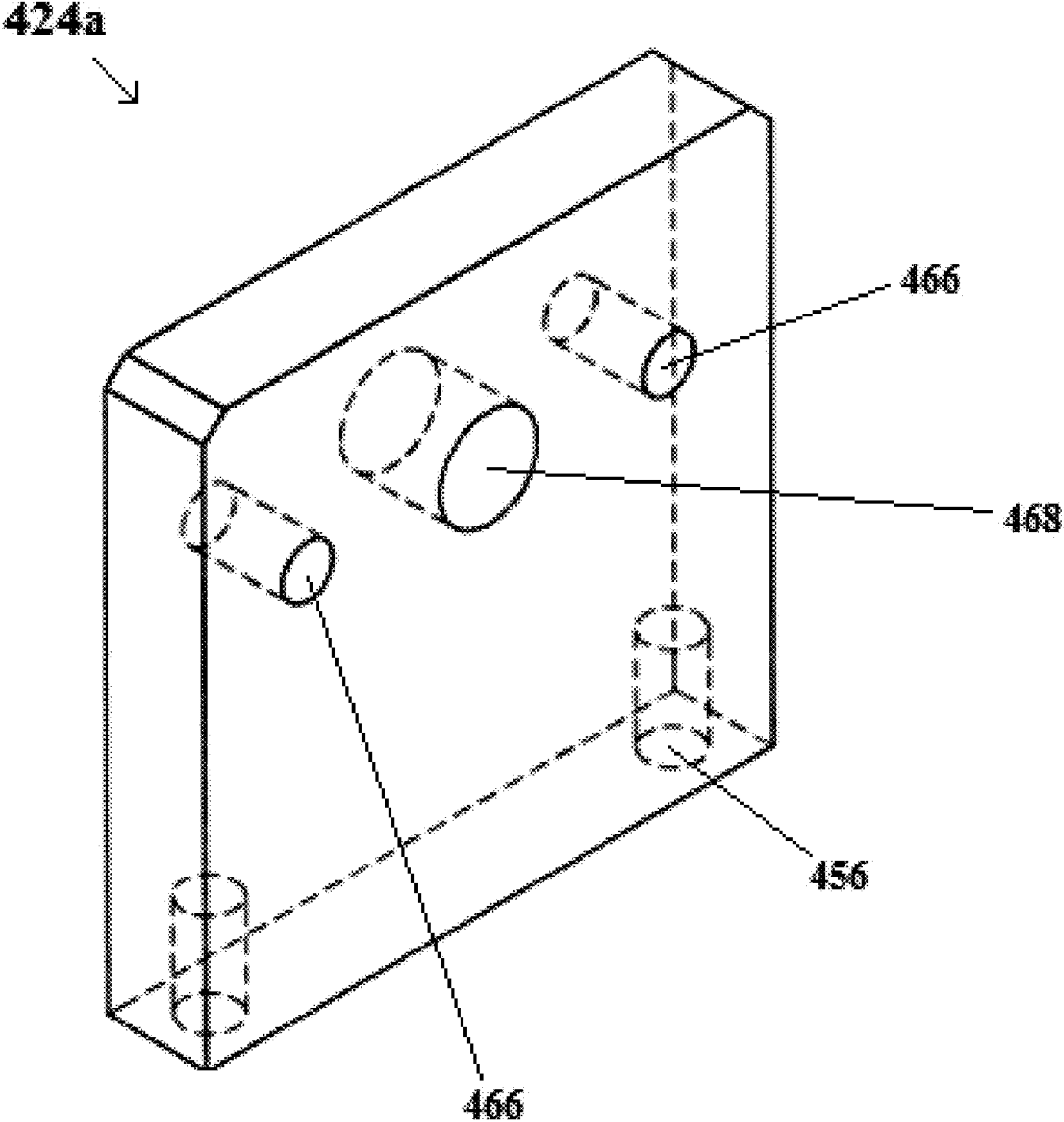
Figure 4I:
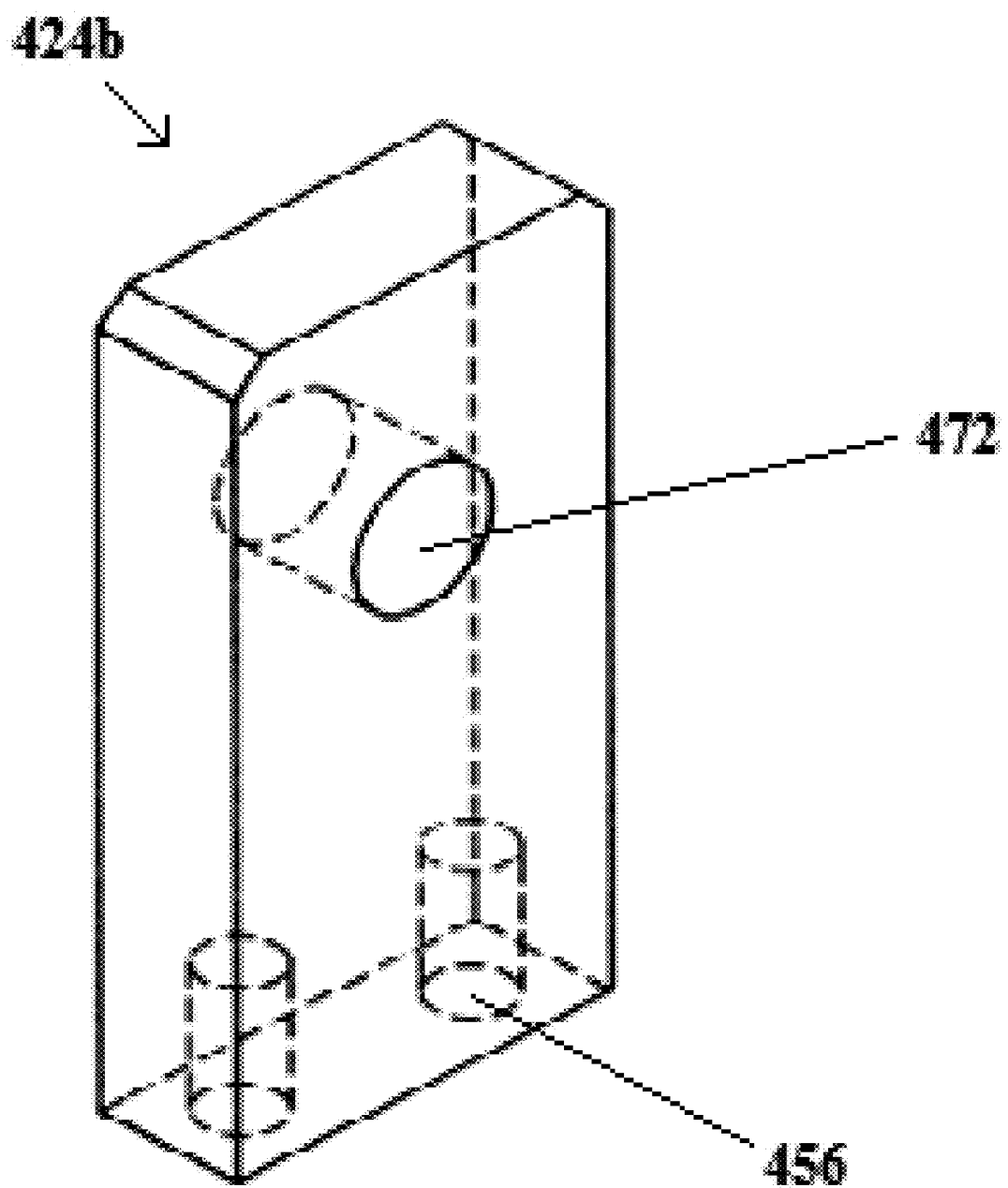

A ball screw drive assembly 422 is used to produce precise linear motion. The ball screw drive assembly 422 can be a mechanical linear actuator that can convert rotational motion to translational motion, and can be the driving mechanism of the scaffold-stretching system 402. The ball screw drive assembly 422 includes a stainless steel ball screw 448 and ball nut assembled together with ball bearings as rolling elements, supported by ball nut holders 436. The ball nut holders 436, as depicted in FIG. 4F, are supports with two smaller apertures 462 configured to receive the connecting rods 418 and one larger aperture 464 configured to receive the ball nut drive assembly 422. A stainless steel assembly ensures a very low coefficient of friction and high efficiency along with precise movement, however, other materials are possible. The ball screw assembly 422 can be supported by one or more bearing supports 424 (depicted as 424a, 424b in FIGS. 4H-4I) at either ends, with ball bearings placed at the interface to facilitate frictionless movement of the threaded screw during operation. A first bearing support 424a can include two apertures 466 configured to receive the connecting rods 418 and one larger aperture 468 configured to receive the ball screw 448. A second bearing support 424b can include only one aperture 472 configured to receive the ball screw 448 from one side and the coupling 432 from the other side. The connecting rods 418 transfer the linear motion of the ball nut due to rotation of the ball screw to the movable plate 412, which in turn produces stretching of the stretchable loading chambers 400.

In the embodiment shown, a two-phase high torque stepper motor 426 is used to drive the motion of the ball screw assembly 422. Coupling 432 connects the ball screw 448 and the motor shaft 452. The motor 426 is capable of producing controlled and precise strains at specified frequencies by the use of an appropriate driver and programmable controller. The motor 426 is fixed onto a polycarbonate base 454 via an aluminum L-shaped support at the base to align the motor shaft 452 with the ball screw 448, and support its weight. The motor shaft 452 and the ball screw 448 are connected together with a stainless steel coupling 432 that has keys 474a, 474b to hold the motor shaft 452 and the ball screw 448 in place and ensure continuous contact. A motor support 428 is interposed between the motor 426 and the coupling 432, and is secured to the polycarbonate base 454 via the L-shaped support, for added stability.

The scaffold-stretching system 402 is set on the polycarbonate base 454, onto which the guiding sleeves 416, bearing supports 424, and the motor support 428 are secured. Each of the guiding sleeves 416, bearing supports 424a, 424b, and motor support 428 include connection holes 456 configured for attachment to the polycarbonate base 454.

In the embodiment shown, the parts of the scaffold-stretching system are generally made up of polycarbonate, aluminum, or stainless steel. These materials are typically chosen putting into consideration the environment in which the system is under operation. For example, the polycarbonate material makes up the main framework of the system and the supports. The polycarbonate material is light, sturdy, capable of bearing weight, biocompatible, and resistant to corrosion at high humidity and temperatures (e.g., 37° C., which is the culture temperature for many cell-based growth environments). Aluminum is useful for the pins 409, 413 and connecting rods 418 due to its ease of machining and anti-corrosion properties, while stainless steel is useful for its robustness, durability, and anti-corrosion properties for parts under wear and tear that include the ball screw assembly 422 and the coupling 432.

Figure 5A:
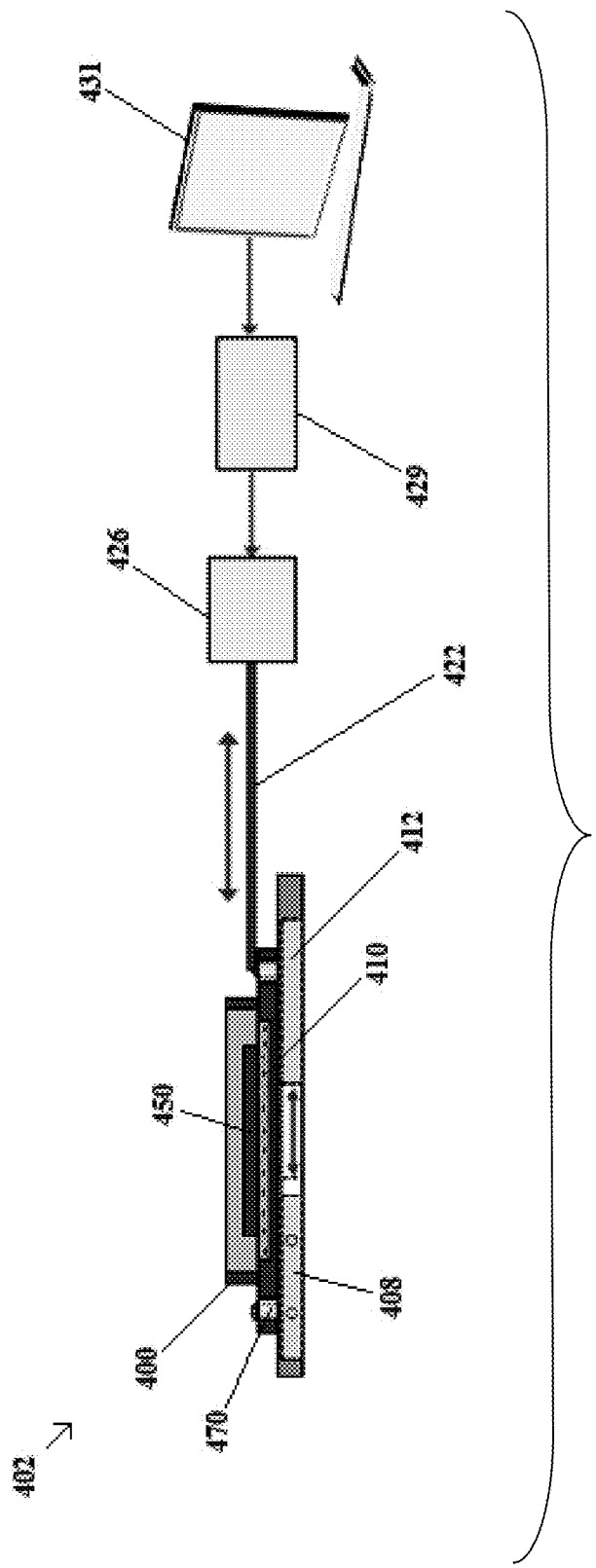
FIGS. 5A-5C: Schematic illustrations of several components useful in the operation of a scaffold-stretching system.
Figure 5B:
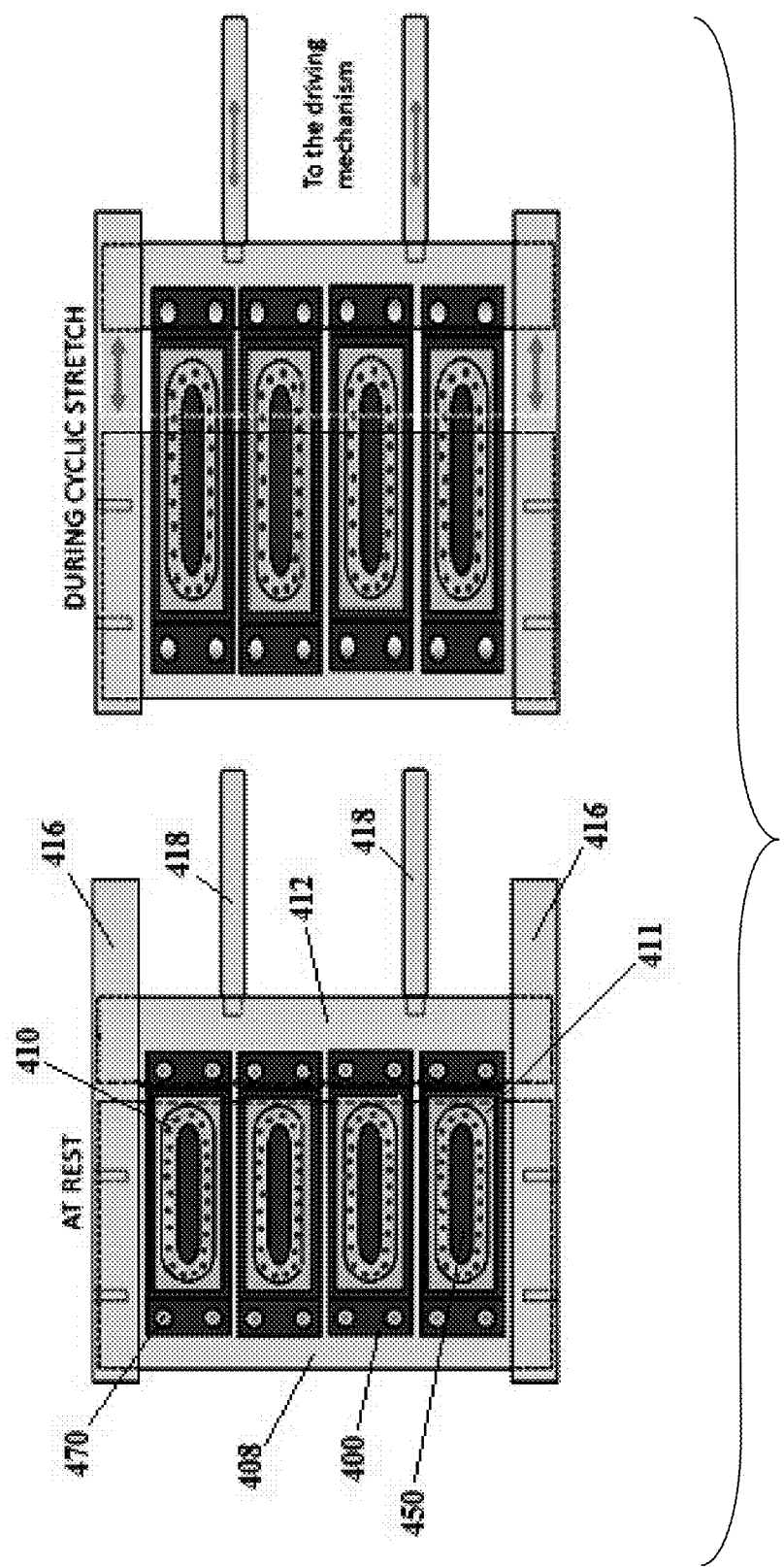
Figure 5C:
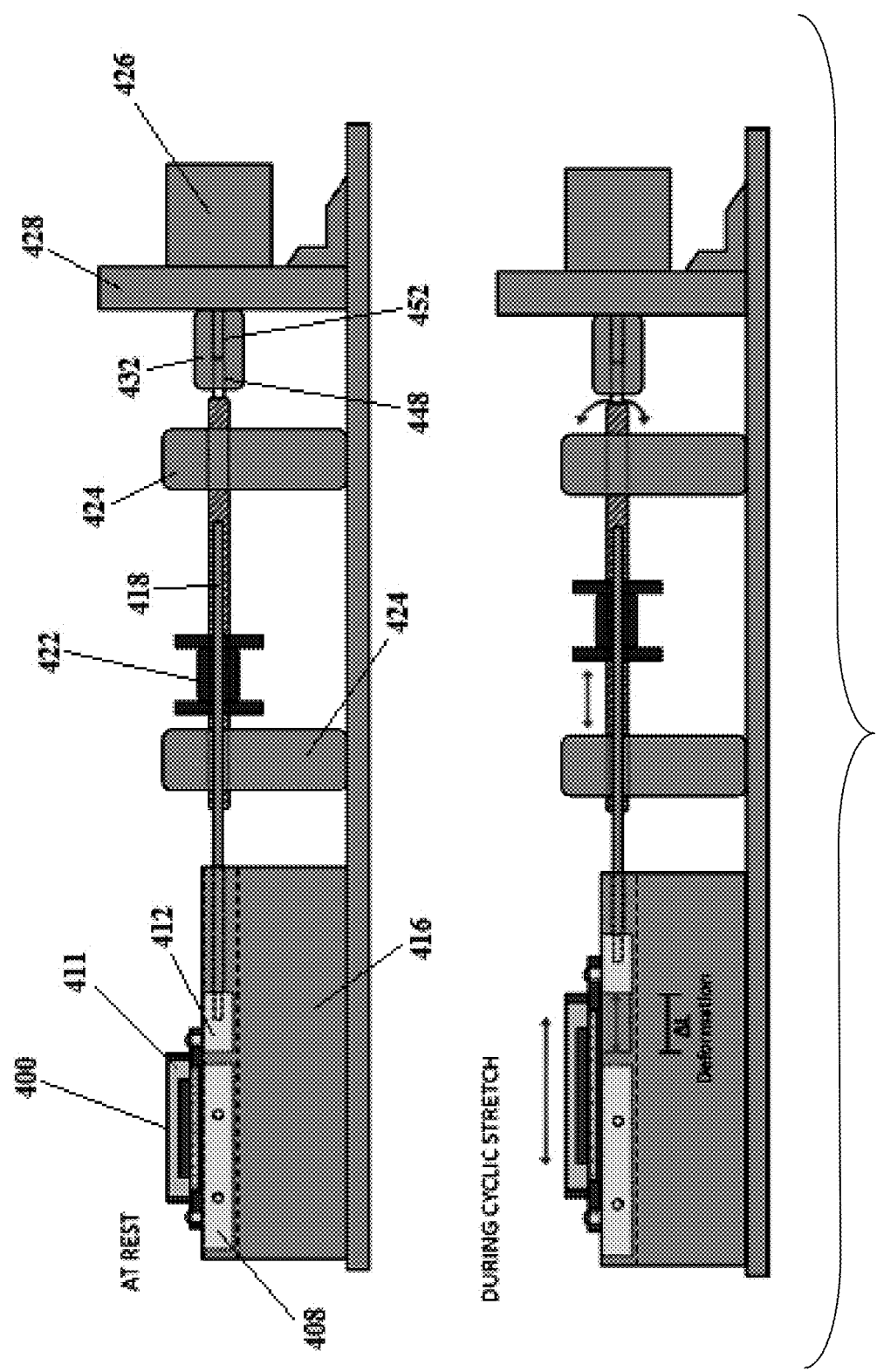

FIGS. 5A-5C shows a schematic illustration of the overall operation of the scaffold-stretching system 402 for cyclic stretching. The high torque stepper motor 426 and its corresponding driver and controller 429 give a wide range of operation in terms of strain and frequency values, controllable through a computer 431. The stepper motor 426 with 200 steps per revolution (1.80 per step) ensures smooth operation and high precision. LabVIEW-based programming software can be used to provide commands inputs to the controller 429 which, in turn, drives the stepper motor 426 to rotate at desired number of revolutions and frequency, along with reversing the direction of motion to make it cyclic. The motor shaft 452, in turn, transmits its rotation to the ball screw 448, which causes the ball nut to move back and forth in linear motion. The ball screw drive assembly 422 has a linear movement of 1.27 mm with one complete revolution of the ball screw 448, based on which the number of revolutions of the ball screw 448 required to produce the desired elongation of the scaffold 410 can be determined. The linear motion from the ball nut is transmitted to the movable plate 412 through the connecting rods 418 attached to the ball nut drive assembly 422. The ends of the stretchable loading chambers 400 are securely inserted onto the pins 409, 413 on the fixed and movable plates 408, 412, such that the stretchable loading chambers 400 are stretched due to the uniaxial reciprocal movement of the movable plate 412. In certain embodiments, any friction between the loading chambers 400 and the plates 408, 412 underneath can be minimized by adding a lubricant (e.g., a few drops of water).

FIG. 5B and FIG. 5C are schematic illustrations of the mechanical loading platform with stretchable loading chambers 400, containing cell culture media 411 and scaffold 410, from two different views, showing the working mechanism under cyclic stretch compared to when at rest. The scaffold 410 can be a collagen construct encapsulated with cells. The stretchable loading chambers 400 can be used as culture chambers for the cells.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1: A Uniaxial Mechanical Loading Platform for Three-Dimensional Tissue Engineered Scaffolds Biological Characterization Cellular three-dimensional scaffolds were prepared by encapsulating the desired cell line within neutralized 3 mg/ml collagen type-I solution (Corning Life Sciences) at $1 \times 10^6$ cells/ml seeding density, and 0.75 ml was added into the grooves of the each of stretchable loading chamber. 1 ml of cell growth media was added into each well of each loading chamber, and stored in a cell culture incubator at 37° C. for 48 hours. The scaffolds were then subjected to cyclic stretching using the uniaxial mechanical loading platform at a desired strain, frequency, and duration of loading by inserting the stretchable loading chambers into the pins of the fixed and movable plates and executing the appropriate command from the motor controller. The loading apparatus was placed in the incubator during its operation, thus ensuring that the cells within the scaffold continue to remain in their preferred environment. After each loading, the stretchable loading chambers were removed from the plates and placed back in the incubator. Media in the well was replenished every 3-4 days. Scaffolds subjected to no loading (unstrained) were used as control samples. The scaffolds were harvested at the end of the experiment with a spatula, and the linear region of the resulting construct was excised from the scaffold using a scalpel blade and used for desired characterization studies. Cell viability, matrix alignment, and changes in gene expression of extracellular matrix were assayed.

For all data herein, percentage strain is defined as the maximum strain experienced by the construct which would be the region nearest to the point of load application. It is calculated by estimating the elongation produced at that particular zone and dividing it by the original length of the construct (25 mm). Frequency is the number of times the construct goes through a stretch and release cycle in one second during uniaxial mechanical loading.

Viability and Proliferation of Cells within Collagen Constructs Subjected to Cyclic Mechanical Loading The cell lines used were Musculoskeletal lineage OB6 (bone), C2C12 (muscle), and AC10 (cardiac). The loading conditions were 5% strain, 0.1 Hz frequency (cyclic), and 1 hour duration for 3 days.

The scaffolds were stretched at the above-described loading conditions for 3 days, and harvested to assess the viability and quantify the amount of DNA obtained from each scaffold.

Figure 6A:
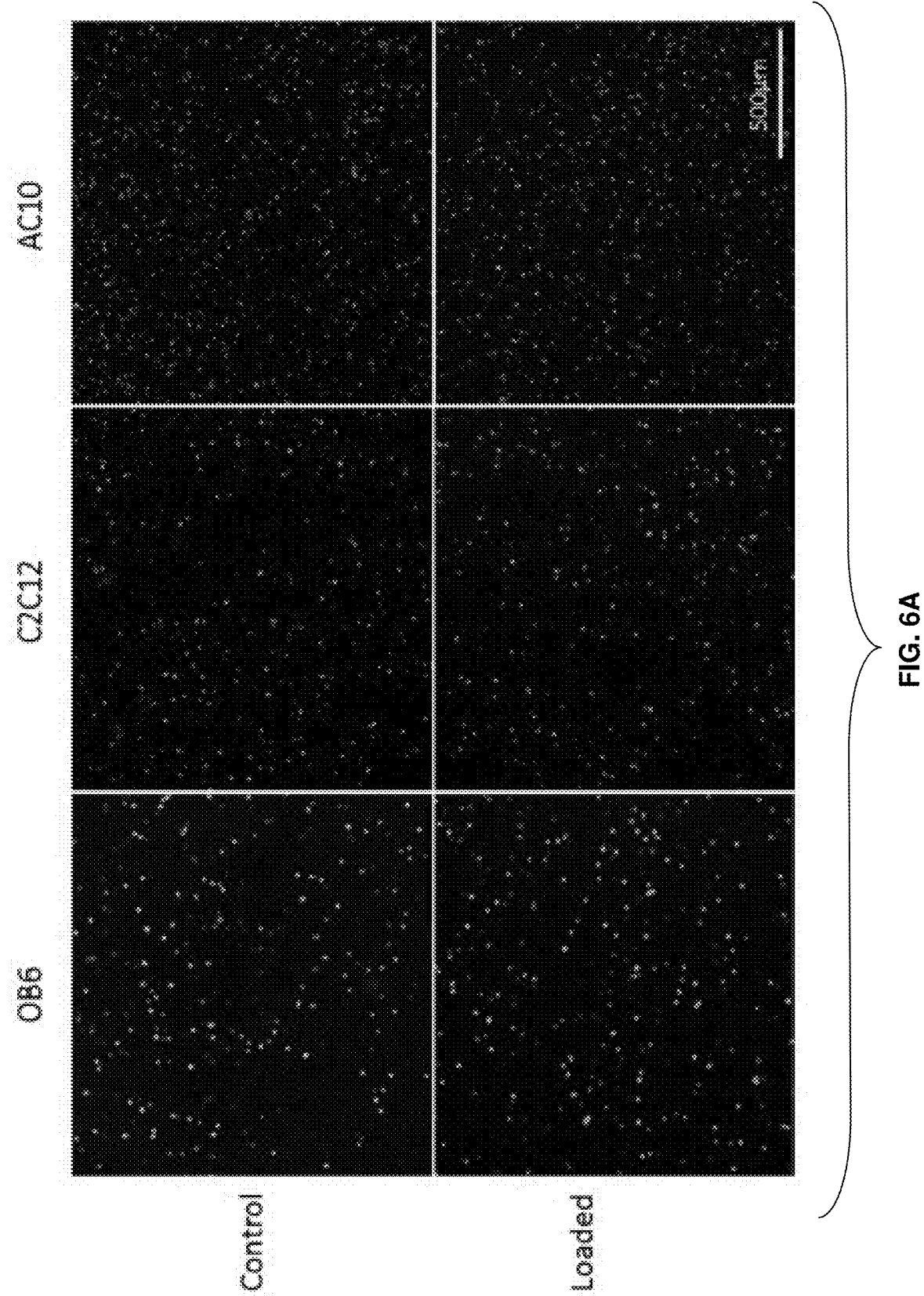
FIGS. 6A-6B: Cell viability and proliferation of three musculoskeletal cell lines after being subjected to three days of loading at 5% strain, 0.1 Hz frequency for 1 hour/day.

The viability of the cells was assessed using Live-Dead Assay kit (Life Technologies) using green (live) and dead (red) dyes, and viewed under confocal microscope. As seen in FIG. 6A, there is no significant difference observed in the ratio of live to dead cells in the control versus the loaded samples for all three cell lines, indicating that applying stretch with the mechanical loading platform does not result in cytotoxicity.

Figure 6B:
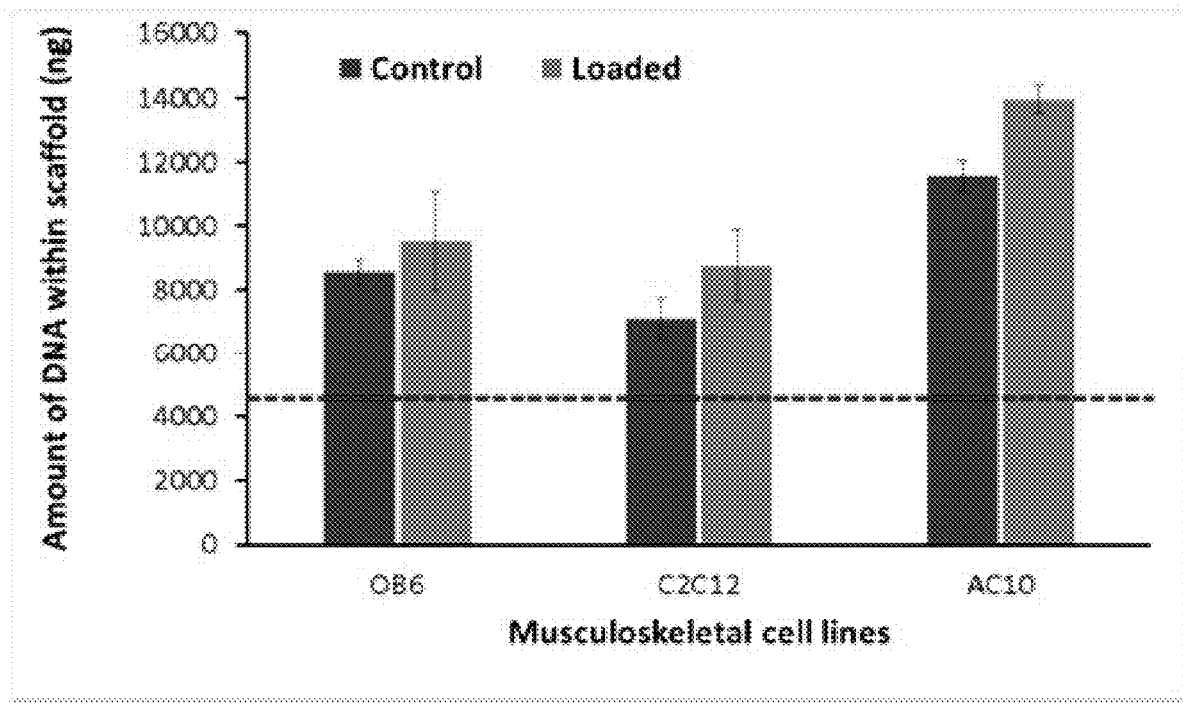

The amount of DNA quantified using Picogreen® dsDNA assay kit (ThermoFisher) confirms that the number of cells within the control and loaded samples for each cell line are in a similar range after 3 days of loading (FIG. 6B). The red dotted line represents the amount of DNA obtained from the initial seeding density of the cells, and there is at least a doubling of the cell number within three days of the experiment. This demonstrates not only that the cells are viable, but that the cells are also able to proliferate similar to the control samples while subjected uniaxial tensile loading regime using the scaffold-stretching system described herein.

Alignment of Scaffold Matrix Due to Cyclic Mechanical Loading

The cell lines used were adipose-derived stem cells (ASC). The loading conditions were 4%/8%/12% strains, 0.1 Hz frequency, and a 2 hour duration for 7 days.

Cellular scaffolds seeded within the silicone loading chambers were subjected to uniaxial loading at above mentioned conditions for 7 days. The scaffolds were fixed and dehydrated and the matrix alignment was visualized through the Scanning Electron Microscope (SEM).

Figures 7A, 7B, 7C:
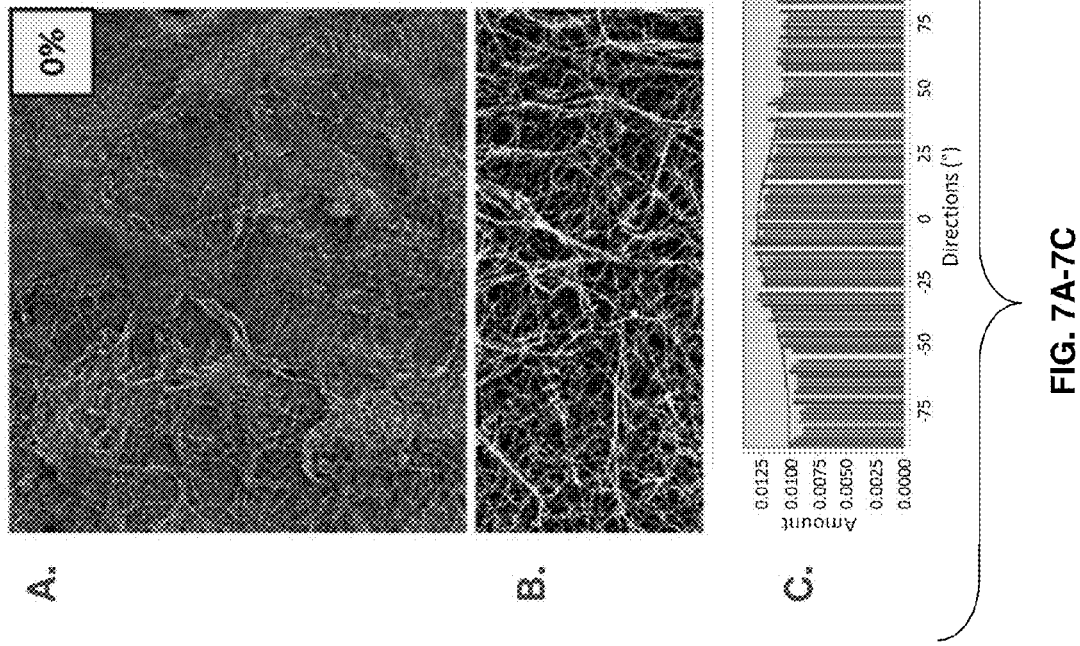
FIG. 7A: Lower magnification SEM images of ASC-seeded collagen constructs subjected to 7 days of uniaxial loading at 0%, 4%, 8%, and 12% strains. Scale bar represents 100 μm.
FIG. 7B: Higher magnification SEM micrographs of the corresponding samples. The inset image depicts the cell morphology within each respective construct. The scale bars indicate 20 μm.
FIG. 7C: Directionality histograms of collagen fibers within scaffolds obtained using ImageJ. Sharper and higher peak demonstrates higher degree of orientation of the fibers.
Figures 7A, 7B, 7C:
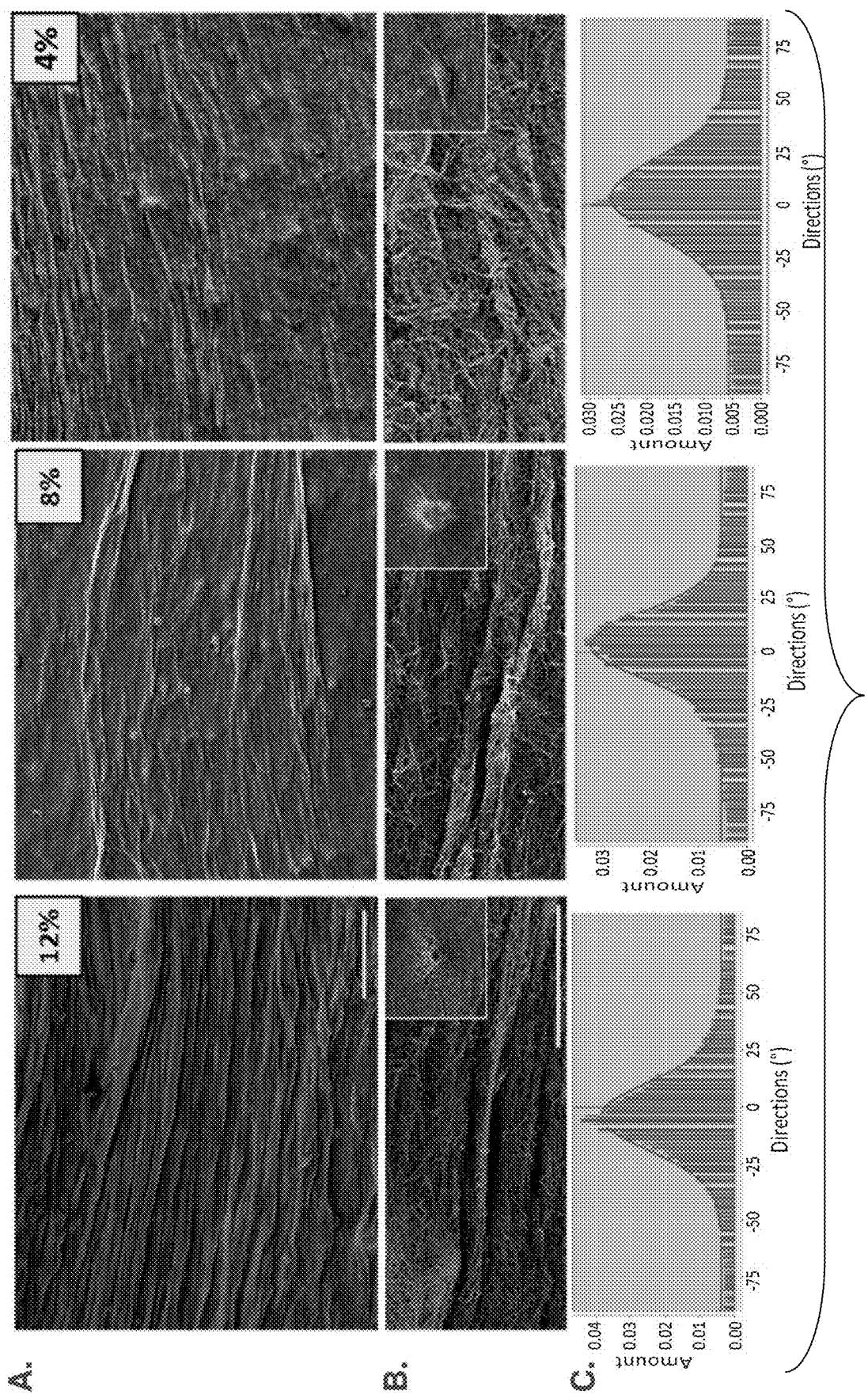
Figure 7D:
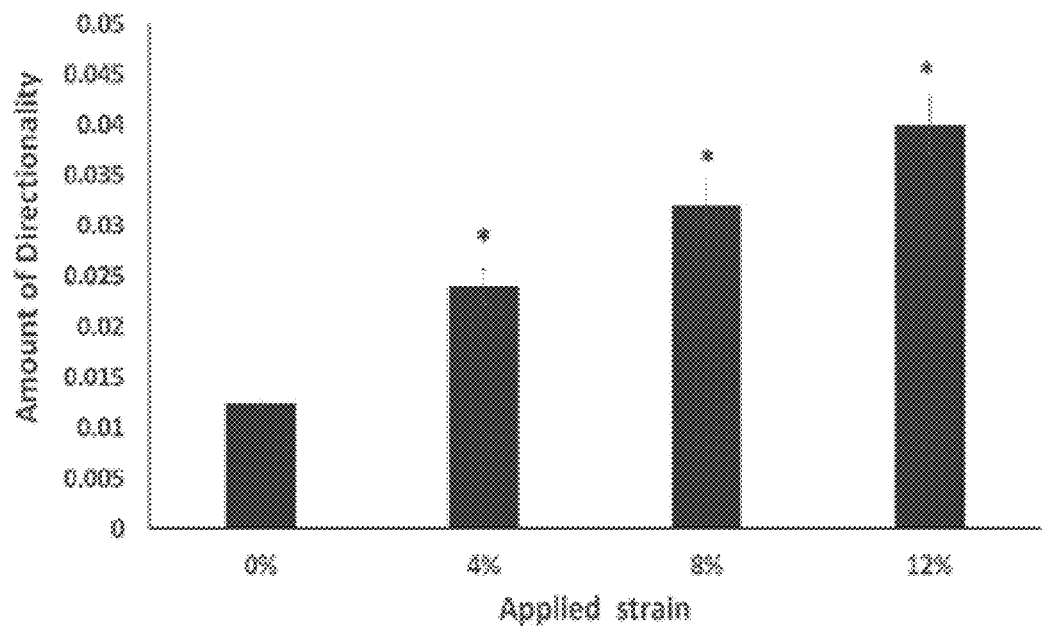
FIG. 7D: Quantified directionality of collagen fibers obtained using ImageJ analysis. * represents statistical difference from the other groups. n=4.

FIG. 7A and FIG. 7B show the matrix alignment at two different magnifications obtained with 4%, 8%, and 12% strain loading regimes compared to the control samples labeled as 0% strain. It is observed that the alignment of the collagen fibers within the scaffold increases with an increase in the magnitude of strain, and the orientation of the fibers is parallel to the axis of load application. Further, the quantification of the directionality of the fibers through ImageJ Directionality plug-in, as shown in FIG. 7C and FIG. 7D, indicates that the degree of orientation of fibers is statistically higher with increase in strain values. These results demonstrate that the uniaxial scaffold-stretching system is capable of aligning the scaffold matrix, and the amount of directionality required can be modulated by varying the strain magnitude.

Extracellular Matrix Gene Expression within Cells Due to Cyclic Mechanical Loading The cell lines used were adipose-derived stem cells (ASC). The loading conditions were 4%/8%/12% strains, 0.1 Hz frequency, and a 2 hour duration for 7 days.

The gene expression profile of extra cellular matrix markers of the cells encapsulated within the loaded and control collagen samples was studied by performing Polymerase Chain Reaction (PCR). Extracellular matrix genes commonly show increased gene expression when cells are subjected to mechanical stimulation. RNA from samples was isolated using TRIzol® reagent (Life Technologies) after complete homogenization of the scaffolds. cDNA synthesis was performed with the obtained RNA using Omniscript RT® cDNA synthesis kit (QIAGEN®). Primer sequences for extracellular matrix genes including Collagen I, Collagen III, Decorin, and Aggrecan were used in the reaction and analyzed using the $\Delta\Delta Ct$ method. The data was graphed as fold difference in gene expression with respect to the control samples.

Figure 8:
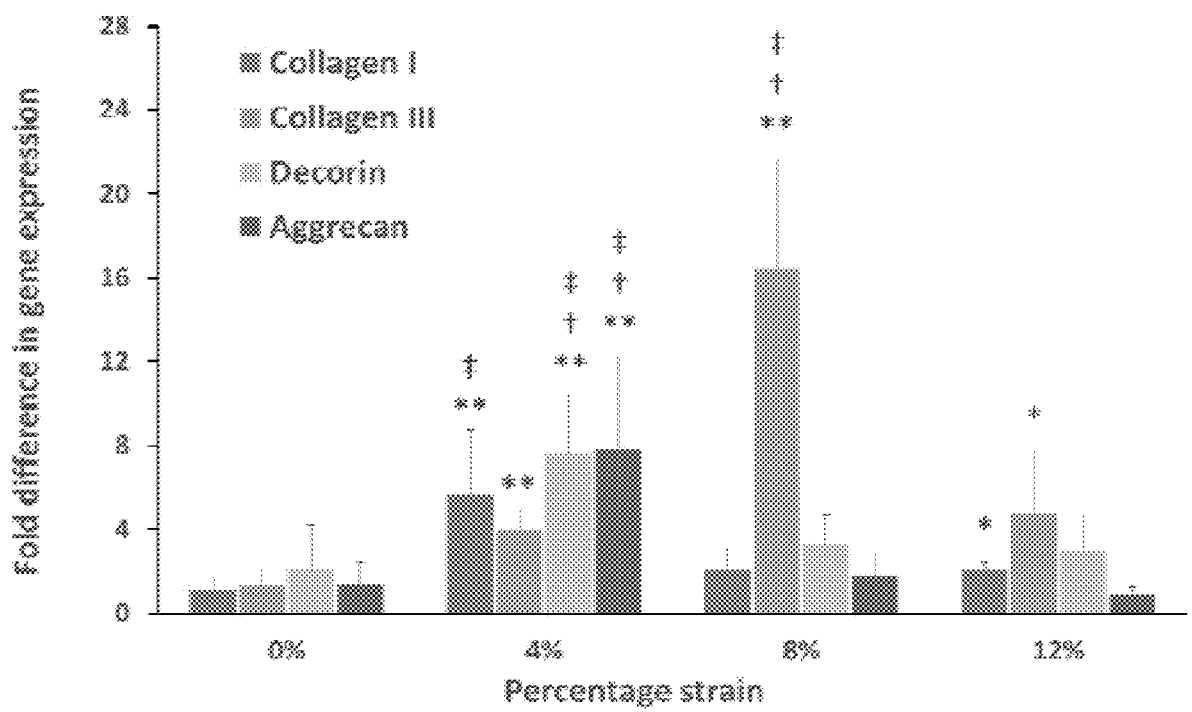
FIG. 8: Gene expression profiles of ASCs encapsulated within collagen scaffolds subjected to uniaxial loading at 0%, 4%, 8%, and 12% strains. The graphs depict fold changes in various musculoskeletal lineage differentiation markers including extracellular matrix genes Collagen I, Collagen III, Decorin®, and Aggrecan®. * indicates significant fold increase with respect to the 0% samples. * indicates $p<0.05$,  denotes $p<0.01$, * corresponds to $p<0.001$. † represents significant difference between 4% and 8% groups while ‡ is the statistical difference with respect to 12% group, both with a 95% confidence interval. n=7.

FIG. 8 demonstrates that there are varying fold increases in the expression level of extracellular matrix genes in every loaded condition, with 4% strain showing statistically higher expression of all four genes, while 8% strain shows huge increase in Collagen III level and 12% strain exhibits increased collagen I and III expression. These results show that along with cell viability and proliferation, application of uniaxial stretch using the scaffold-stretching system also triggers cell differentiation responses.

Mechanical Characterization of the Loading Platform

Mechanical characterization of the stretchable loading chambers seeded with collagen type-I scaffolds was conducted by determining the strain values experienced by the stretchable loading chamber and the collagen scaffold through experimentally validated Finite Element Analysis. The method of scaffold synthesis was similar to the previously described example, with the only change being that the final collagen concentration was 2.5 mg/ml instead of 3 mg/ml. All results were generated for the linear part of the scaffold.

Geometry and Meshing

The dimensions of the stretchable loading chamber were as described above. The model assembly was meshed with C3D10I, which is a 10-node general purpose tetrahedron with improved surface stress formulation elements. Mesh sensitivity studies were conducted to obtain the most computationally efficient mesh without affecting the obtained results.

Material Properties

Figure 9:
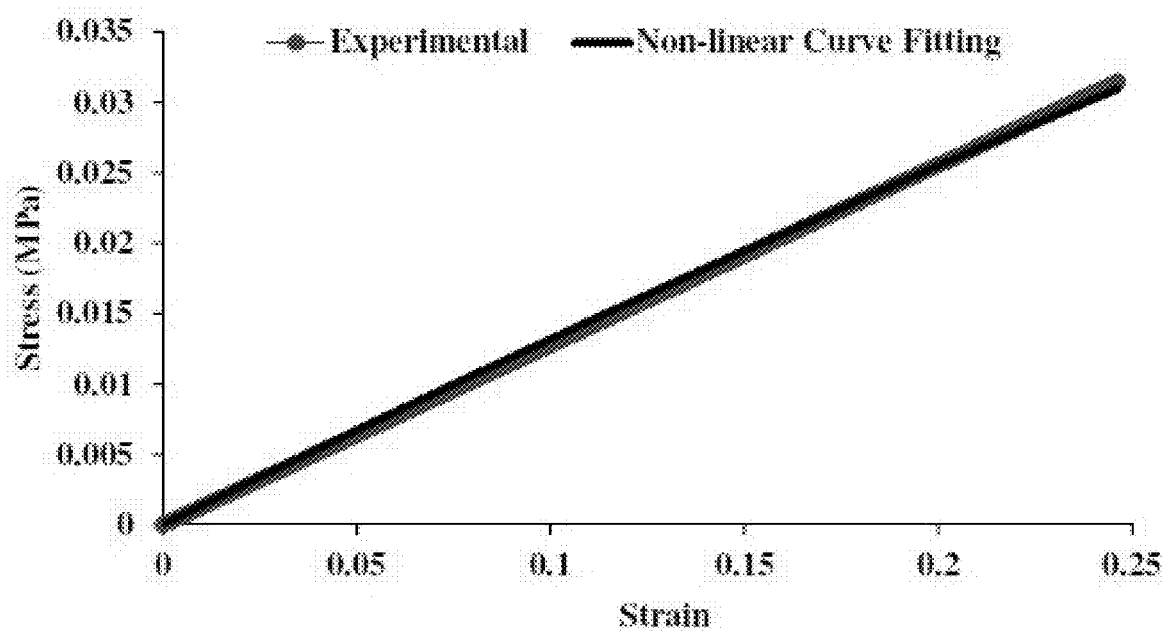
FIG. 9: Stress strain curves obtained from both tensile mechanical testing of the silicone loading chambers (n=6) and FEM model.
Figure 10:
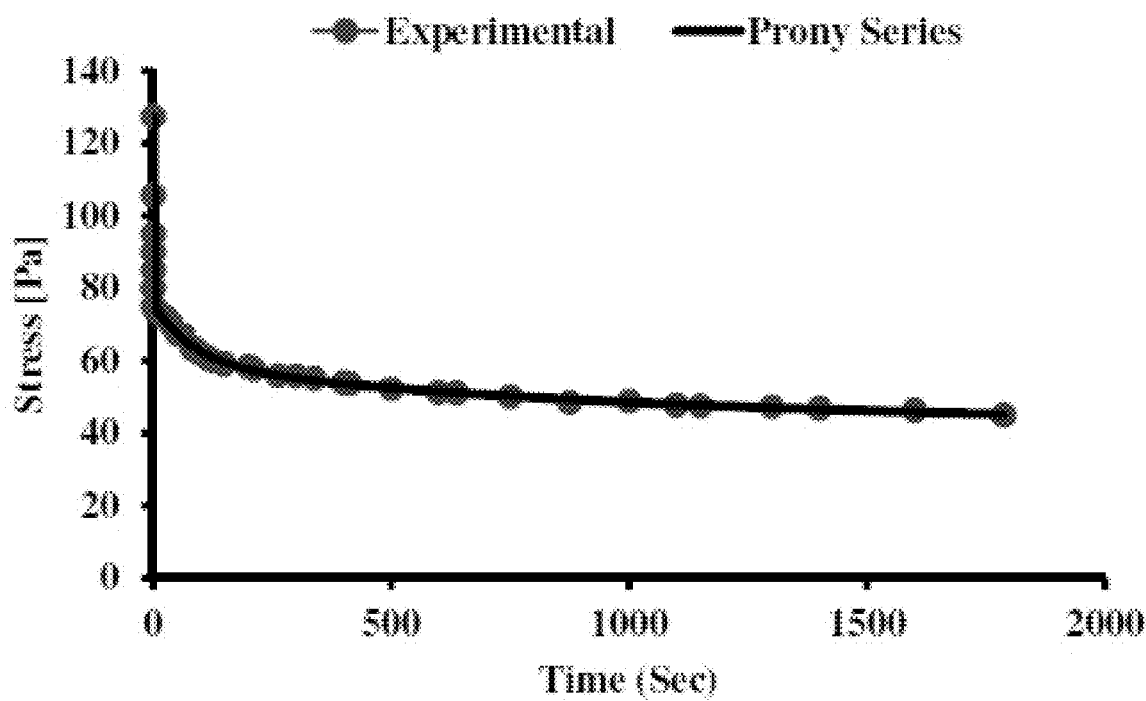
FIG. 10: Stress relaxation curves for 2.5 mg/ml collagen from experiments and nonlinear curve fitting.

The stretchable loading chamber that was composed of silicone was modeled as a hyperelastic material according to Ogden model. Ogden material parameters were obtained via nonlinear curve fitting of the experimental uniaxial tensile testing data. The stress-strain curve used to obtain Ogden material model parameters is given in FIG. 9. A summary of Ogden material parameters obtained via nonlinear curve fitting and used in the Finite Element Models is given in FIG. 16—Table 1. The polycarbonate fixed and movable plates were modeled as an elastic material. Young's modulus and Poisson's ratio were obtained from the supplier (McMaster-Carr, USA) and were 2.4 GPa and 0.35, respectively. Collagen constructs were modeled as a viscoelastic time-dependent material according to Prony series model. Prony series material parameters were obtained by the nonlinear curve fitting of a stress relaxation curve. The experimental stress relaxation and the fitted curve are and a summary of the material parameters used in the FE models is given in FIG. 16B—Table 2.

Loading and Boundary Conditions

Figure 11:
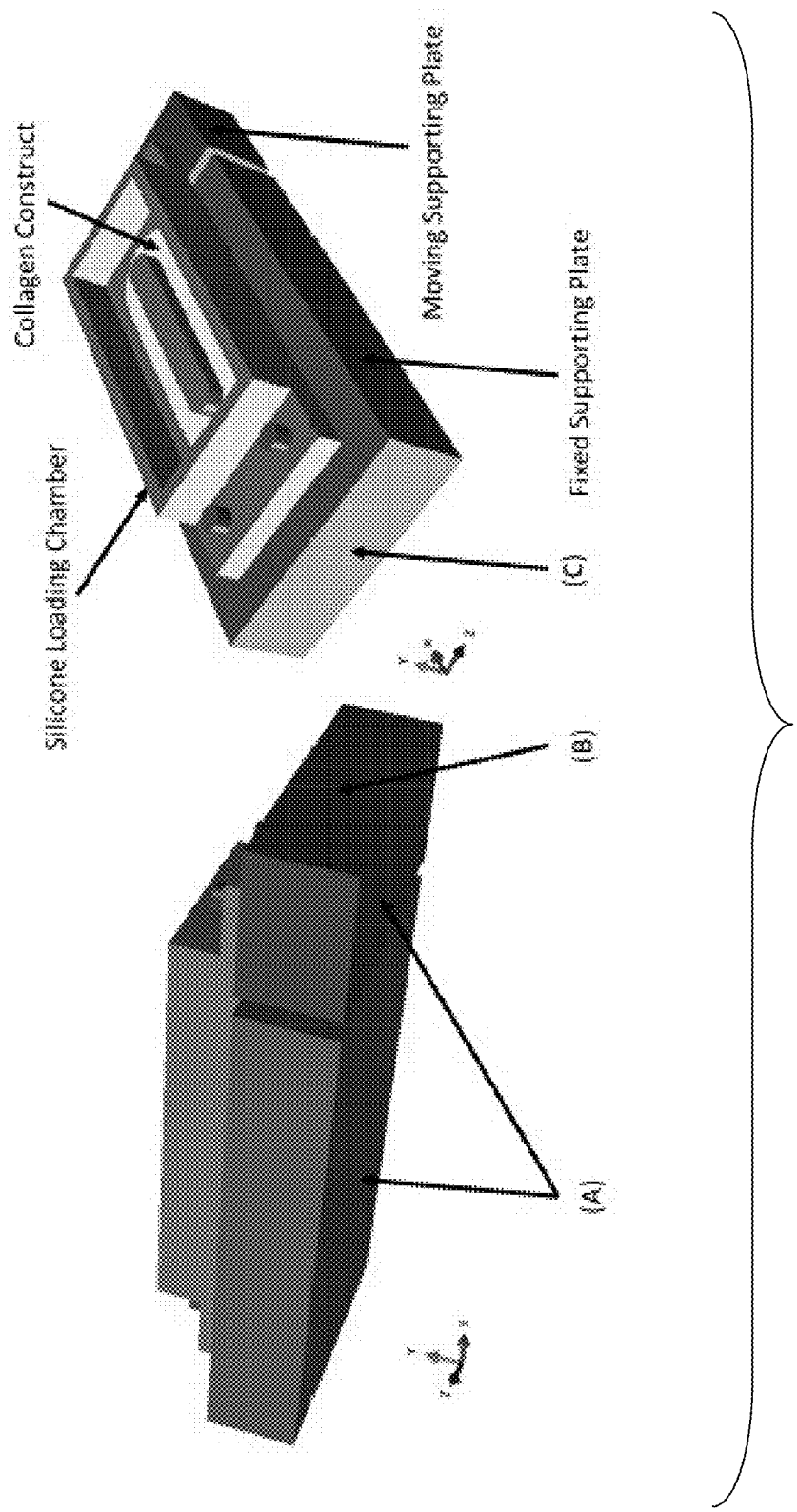
FIG. 11: Perspective views of loading and boundary conditions—bottom perspective (left) and top perspective (right).

Two representative views of the loading assembly with the surfaces used to apply the loading and boundary conditions are shown in FIG. 11. Both the fixed and moving supporting plates bottom surfaces (A) were constrained in both X and Z axes. Surface (C) was constrained in the X axis. The load was applied on surface (B) via kinematic coupling with a reference point that is constrained in all degrees of freedom except the X direction. The load was applied as displacement controlled boundary condition on the reference point. Surface to surface interaction was applied to the interface of silicone loading chamber and the polycarbonate supporting plates and also between silicone and the collagen construct. For the silicone-polycarbonate interactions, normal penalty hard contact, and tangential static-kinetic exponential decay frictional contact were used. The static coefficient of friction was set to 1.0, the kinetic coefficient of friction was 0.5, and the exponential decay coefficient was 0.2. For the silicone-collagen interactions, normal hard contact and tangential frictional exponential decay with the static and kinetic coefficients were set to 2.0 and 1.0, respectively. The exponential decay coefficient was 1.0.

Deformation Contours of Collagen Constructs within Silicone Loading Chambers

Figure 12:
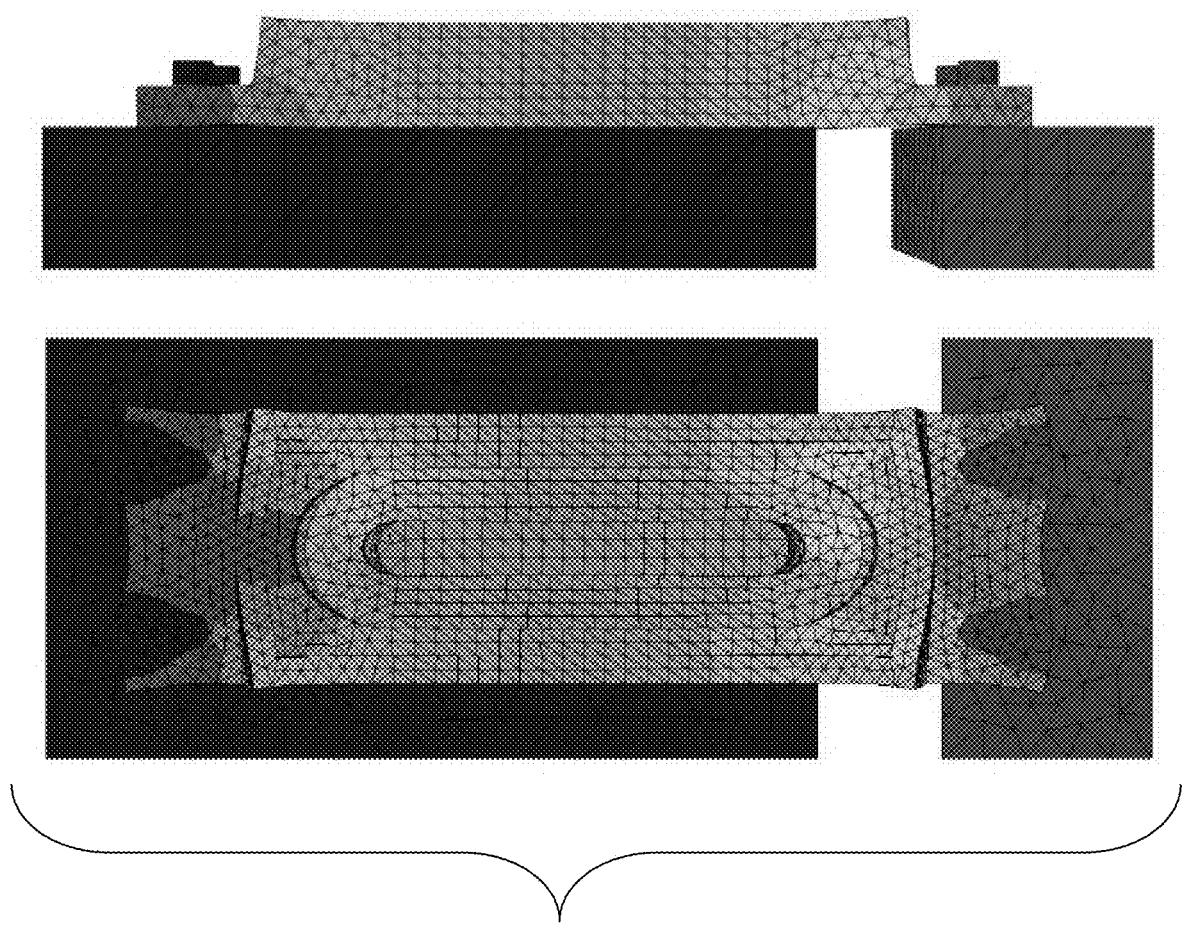
FIG. 12: Deformation contour of the collagen construct within the stretchable loading chamber—side elevation view (top) and top view (bottom).

Deformation contours were obtained after the completion of FE runs. FIG. 12 demonstrates the deformation contours of the front and top view of the tensile loading assembly. The contours proved to reflect the experimental deformations that were noticed while conducting uniaxial stretch of the collagen constructs inside the silicone loading chambers.

Figure 13:
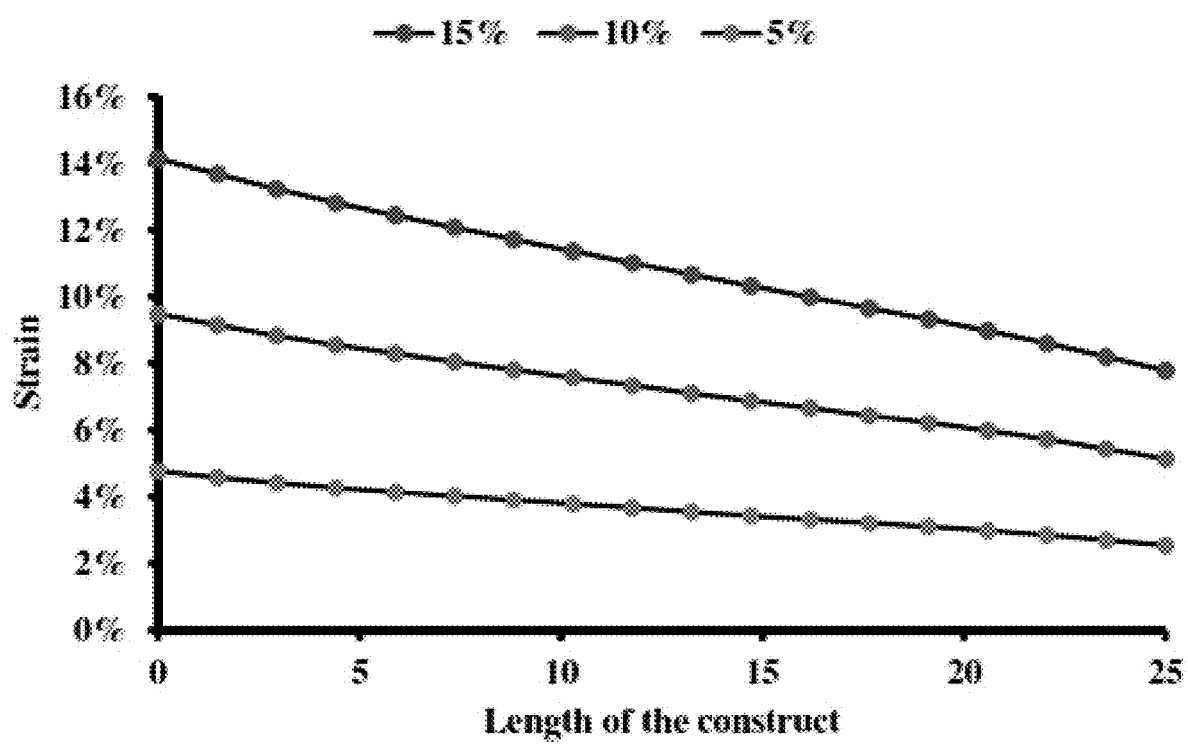
FIG. 13: Strain gradients across the length of the collagen constructs for various strain values.

The strain gradients over the linear part of the collagen constructs are given in FIG. 13. The strain is maximum at the points closer to the point of load application. The strain gradient is steeper at the higher applied loads.

Strain Calculations

Figure 14:
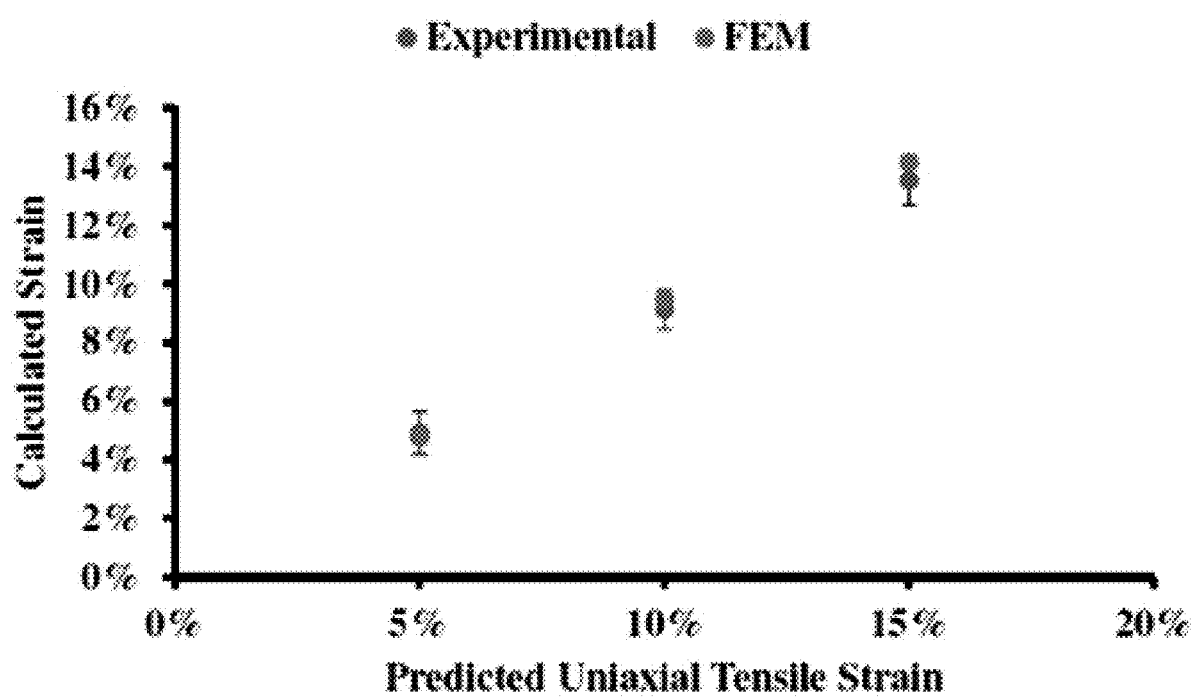
FIG. 14: Comparison between the strains experienced by the collagen constructs both experimentally and numerically.

Experimental strain calculations were conducted by placing glitter into specific regions of the scaffold, taking images at different strained values, and conducting image analysis. The unloaded (zero strain) and strained positions of the glitter dots were captured and measured using an image processing software (ImageJ, NIH, USA). The strain is then calculated using the original length of the linear part of the collagen construct and the deformed length. The original and deformed coordinates of the nodes at the same positions were obtained from the FE model and used also to calculate the tensile strain. The strains obtained experimentally and via the FE model are shown in FIG. 14. The FE model was successful to predict the strain experienced by the collagen construct as seen in FIG. 1.

Figure 15:
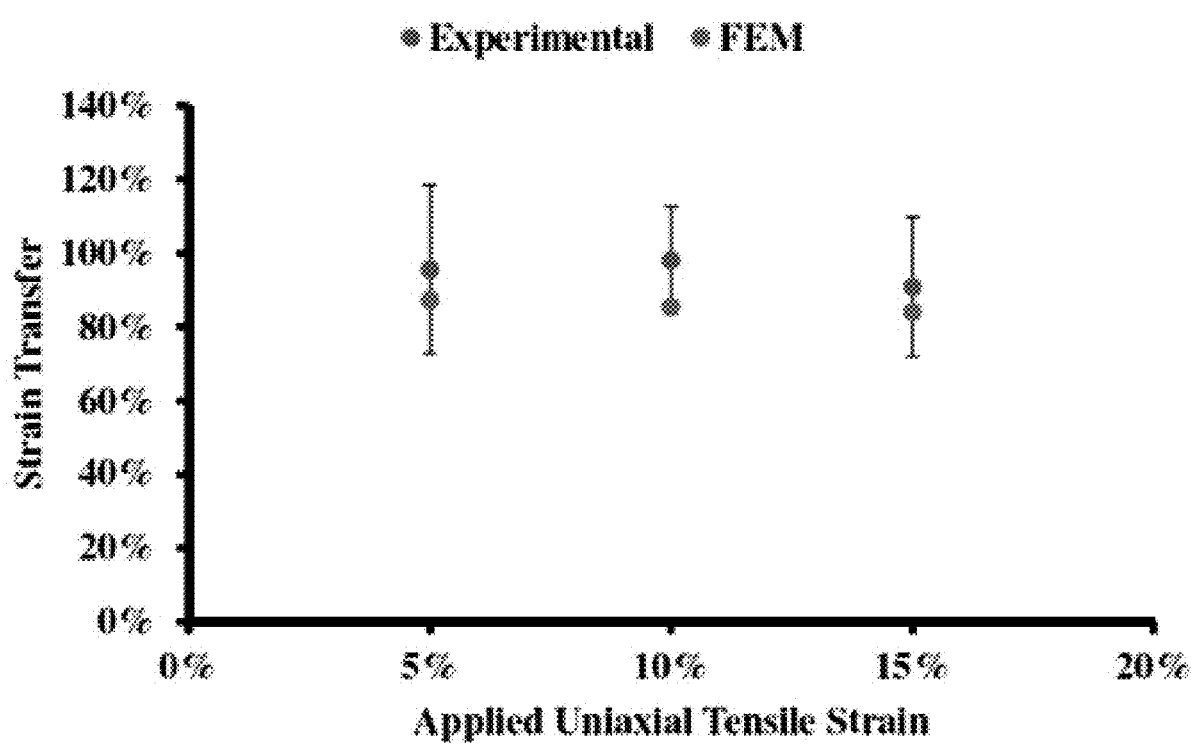
FIG. 15: Comparison between the strain transfer between silicone loading chamber and the collagen constructs obtained both experimentally and numerically.

Additionally, the strain transfer from silicone loading chamber to the collagen constructs were calculated from the experimental observations as well as the FE model. The strain transfer percentage was obtained by dividing the collagen construct strain by the silicone strain. The strain transfer obtained experimentally varied between 91% and 96% (±15%) depending on the applied load while the percentage strain transfer obtained using the FE models varied from 84% to 87% as seen in FIG. 15. Thus, the strain transfer calculations obtained numerically agreed well with the experimental estimated results.

Example 2: Homogenous Strain Distribution within 3D Cell-Encapsulated Constructs Using a Simple and Cost-Effective Uniaxial Tensile Bioreactor Mechanical loading bioreactors capable of applying uniaxial tensile strains are a valuable tool to investigate physiologically-relevant cellular signaling pathways and biochemical expression. In this Example, a simple and cost-effective uniaxial tensile strain bioreactor was used for the application of precise and homogenous uniaxial strains to 3D cell-encapsulated collagen constructs at physiological loading strains (0-12%) and frequencies (0.01-1 Hz). The bioreactor employed silicone-based loading chambers specifically designed to stretch the collagen constructs without direct gripping to minimize stress concentration at the ends of the construct and preserve the construct integrity. The loading chambers were driven by a versatile stepper motor ball-screw actuation system to stretch the 3D collagen constructs. Mechanical characterization of the bioreactor performed through Finite Element Analysis demonstrated that the constructs experienced predominantly uniaxial tensile strain in the longitudinal direction. The strain produced was found to be homogenous over a 15×4×2 mm region of the construct equivalent to around 60% of the effective region of characterization. The strain values were also shown to be consistent and reproducible during cyclic loading regimes. Biological characterization confirmed the ability of the bioreactor to promote cell viability, proliferation, and matrix organization of cell-encapsulated collagen constructs. This easy-to-use uniaxial tensile strain bioreactor can be employed for studying morphological, structural, and functional responses of cell-embedded matrix systems in response to physiological loading of musculoskeletal tissues. It can also be used for tissue-engineered strategies that involve delivery of mechanically-stimulated cells at the site of injury through a biological carrier to develop a clinically useful therapy for tissue healing.

Musculoskeletal tissues exist in a dynamic in vivo environment where they experience various kinds of mechanical strains including tensile, compressive, and shear on a daily basis. Uniaxial tensile forces, particularly relevant to bone, tendon, ligament, and skeletal muscles are hence known to induce specific biological responses in resident mesenchymal cells. It has been observed that the strained cells respond by altering their size, morphology, proliferation rate, and extracellular matrix gene expression that direct changes in tissue structure, composition, and mechanical properties. Thus, uniaxial tensile bioreactors that can simulate the mechanical microenvironment of musculoskeletal cells have emerged as a valuable tool to investigate the biochemical expression and signaling pathways underlying the cellular behavior to mechanical stimulation.

Bioreactors capable of stretching three-dimensional (3D) cellular constructs are considered to be good biomimetic models due to their ability to mimic the complexities of the cellular microenvironment along with mechanical cues. Current uniaxial tensile strain bioreactors for loading 3D cellular constructs include the commercially available Flexcell® Tissue Train® Culture system, STREX 3D Cell Stretching system, and CellScale MechanoCulture system, along with a few custom-built tissue bioreactors. Flexcell® in particular has been widely used for applying uniaxial strains due to its well-characterized strain profile and varied modes of loading. These bioreactors that stretch soft biomaterials (predominantly collagen) require innovative techniques to grip the construct without compromising its structural integrity. Most of such bioreactors employ nylon mesh or foam anchors as grips onto which the collagen solution is poured and allowed to polymerize to minimize risk of construct disintegration during mechanical loading. Also, they are often coupled with a pneumatic non-contact actuation system to deform the membrane onto which the cell-seeded collagen constructs are anchored at the ends. However, this actuation and gripping system can typically lead to non-homogenous strain distribution within the collagen construct where the strain experienced by the cells inside the construct vary significantly based on their spatial location. It is observed that only a narrow uniform strain region near the center of the construct is obtained, while wide variation in strain magnitudes are seen near the ends of the construct. Thus, there is a persistent demand for uniaxial tensile strain bioreactors that can produce enlarged area of homogenous strain distribution within 3D cellular constructs along with minimal risk of construct disintegration.

In this Example, a simple and cost-effective uniaxial tensile strain bioreactor was used to apply homogenous cyclic strains to 3D cell-encapsulated collagen constructs over major part of its length without compromising its structural integrity. In addition, it is also easy to setup, operate, and maintain, and compact enough to fit into a standard cell culture incubator. The bioreactor uses silicone-based loading chambers specifically designed to effectively stretch the 3D collagen constructs without direct gripping of the constructs. It is driven by a precise and versatile stepper-motor ball-screw actuation system to apply consistent and reproducible uniform uniaxial strains in the range of physiological loading frequencies of musculoskeletal tissues. The bioreactor performance was first evaluated by characterizing the spatial strain profiles experienced by the 3D constructs under static and cyclic loading conditions through Finite Element Analysis. Next, the uniaxial tensile strain bioreactor was biologically characterized to investigate its effect on cell viability, proliferation, and matrix organization within 3D cell-encapsulated collagen constructs.

Materials and Methods

Uniaxial Tensile Strain Bioreactor

Figure 17:
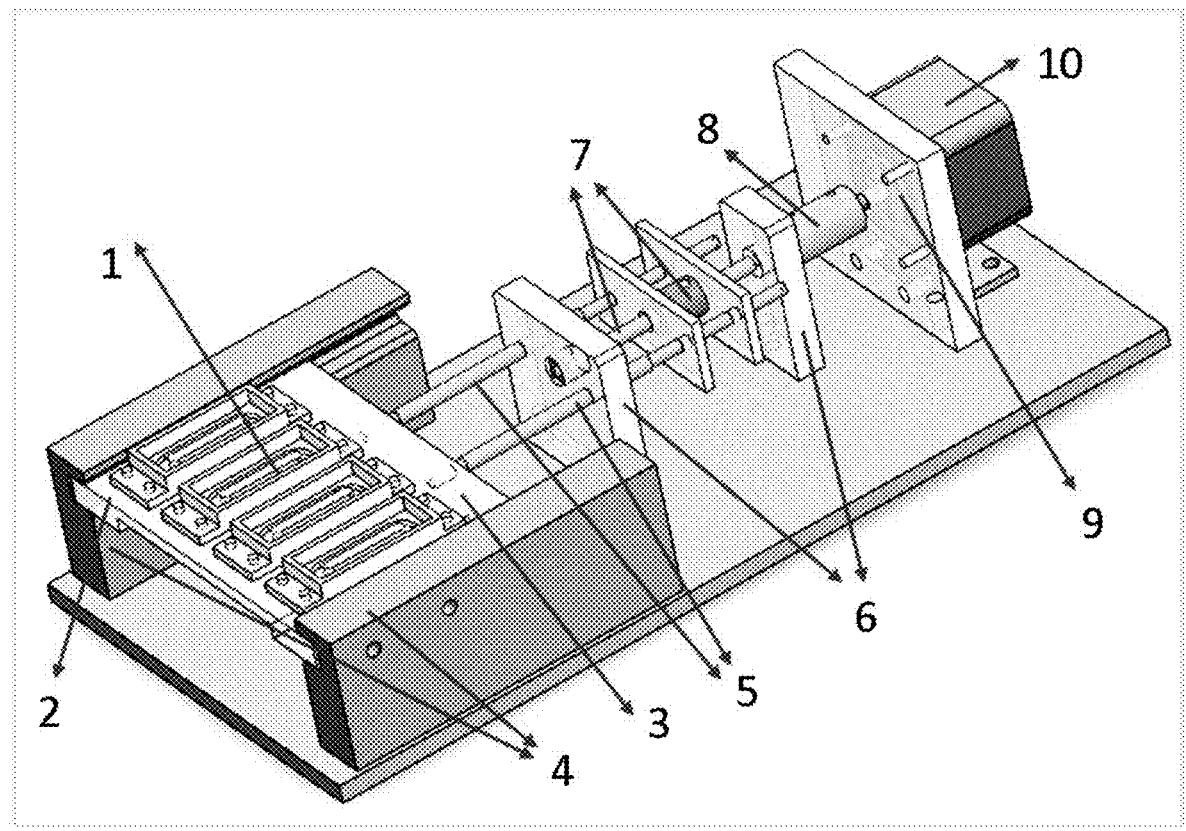
FIG. 17: Schematic of the uniaxial tensile strain bioreactor described in Example 2 herein. (1) Silicone loading chambers containing the 3D collagen constructs. (2) Fixed plate. (3) Moving plate. (4) Guiding sleeves for supporting plates. (5) Connecting rods to transmit motion to the moving plate. (6) Bearing supports to hold the ball-screw mechanism. (7) Ball screw mechanism to produce precise linear motion. (8) Coupling connecting the screw and the motor shaft. (9) Motor support. (10) 2-phase high torque stepper motor connected to a programmable controller to produce controlled stretch.

FIG. 17 shows a schematic of the uniaxial tensile strain bioreactor used for mechanical stimulation of 3D collagen constructs, having silicon loading chambers containing the 3D collagen constructs, a fixed plate, a moving plate, guiding sleeves for the supporting plates, connecting rods to transmit motion to the moving plate, bearing supports to hold the ball-screw mechanism, a ball-screw mechanism to produce precise linear motion, a coupling connecting the screw and the motor shaft, a motor support, and a 2-phase high torque stepper motor connected to a programmable controller to produce controlled stretch. All mechanical components were designed using SolidWorks 3D CAD design software (SolidWorks, MA). The individual components were manufactured and assembled at a high-precision local machine shop (OBARS Machine and Tools Company, OH). The parts of the strain bioreactor were made of polycarbonate, aluminum or stainless steel (McMaster-Carr, IL), suitable for operation in the cell culture environment. The loading chambers made of silicone were supported by a polycarbonate base consisting of fixed and moving plates that have aluminum pins fitted on one of their ends to secure the loading chambers. The plates were supported by polycarbonate guiding sleeves on either side to allow translation motion of the moving plate, while the fixed plate was screwed into the guiding sleeves to render it stationary. Two connecting rods screwed into the free end of the moving plate were responsible for transferring the motion from the driving mechanism to the silicone loading chambers. A precision ball screw assembly (Thomson Linear Motion Systems, VA) coupled with a two-phase high torque stepper motor with driver-controller (Lin Engineering, CA) constituted the actuation system of this bioreactor. This system ensures high efficiency in transfer of rotational motion of the ball screw to translational motion of the ball nut linked to the connection rods that displace the moving plate, which in turn produces stretching of the silicone loading chambers containing the collagen constructs. The entire assembly was placed on a polycarbonate base, into which the fixed components of the bioreactor were secured, and a polycarbonate lid was used to cover the loading chambers during mechanical stimulation.

Silicone Loading Chamber

Figure 18:
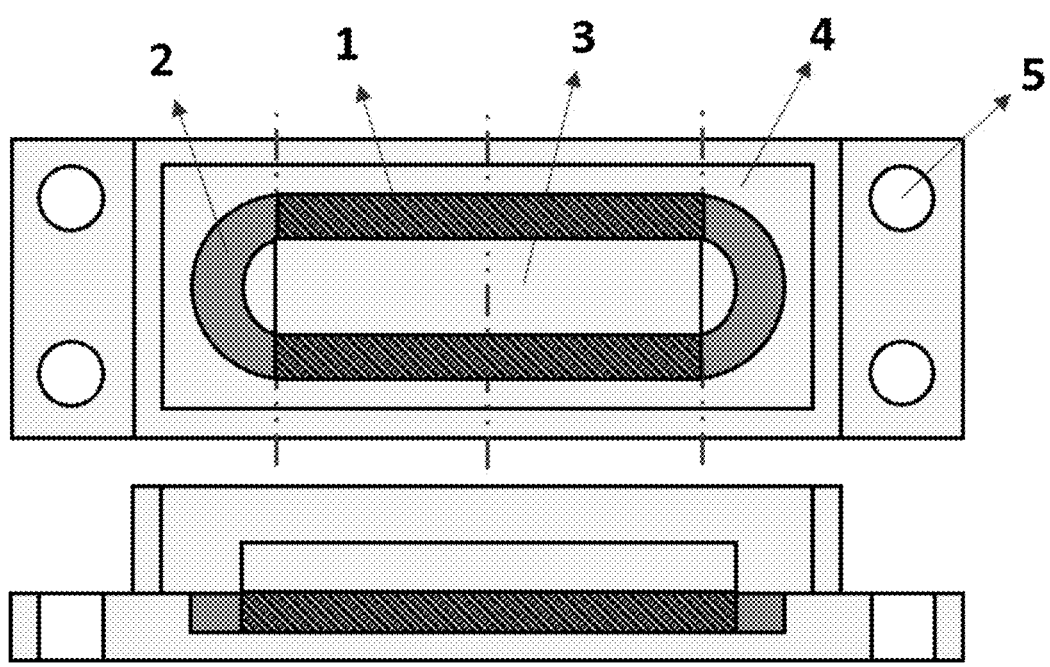
FIG. 18: Schematic of the silicone loading chamber used in Example 2 herein. (1) Groove into which cellular collagen constructs are polymerized, comprising linear strips (shaded) with dimensions of 25×4×2 mm (L×W×T), indicating the effective region for characterization, and (2) semicircular strips at either ends linking the two linear strips of the construct. (3) Island at the center provides support to the constructs during loading. (4) Well to hold sufficient media for cell survival, proliferation, and differentiation. (5) Pin holes through which the supporting base plates are inserted in order to apply loading.

The silicone-based loading chambers were specifically designed to maximize the mechanical load transferred to the 3D collagen constructs through minimizing the relative movement (sliding) of collagen construct during mechanical loading without the use of direct grips. The main features of the loading chamber are shown in FIG. 18. The cellular collagen construct was added within the groove of the loading chamber that comprises two linear strips connected by circular sections on either side.

The dimension of one linear strip was 25×4×2 mm (L×W×T), which is considered as the region of characterization of the construct. Collagen was supported by an island at the center to eliminate direct gripping at the ends and increase homogeneity in strain distribution across the linear part of the construct. The groove and island were enclosed within a well to hold cell culture media for the cell-encapsulated constructs. The well was flanked by flaps having pinholes through which aluminum pins from the supporting base of the bioreactor system is inserted in order to producing stretching of the loading chambers. A mold corresponding to the geometry of the chamber was used to fabricate the silicone loading chambers. Silicone rubber components (Dragon Skin® 10, Smooth On) was mixed in a 1:1 ratio, poured into the mold, and allowed to polymerize to obtain the chambers.

Figure 19A:
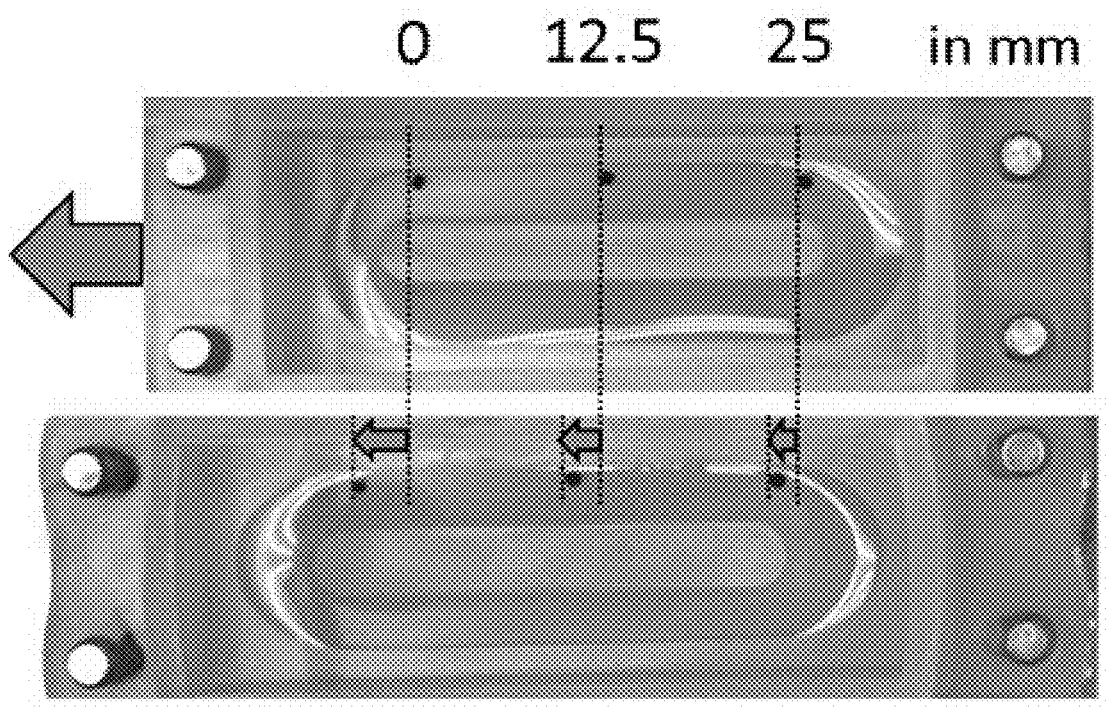
FIGS. 19A-19B: Experimental validation of the uniaxial tensile strain bioreactor and FEM generation.

Experimental Validation of Uniaxial Tensile Bioreactor with 3D Collagen Constructs The uniaxial tensile strain bioreactor was experimentally validated to evaluate the efficiency of the device in transmitting the applied load to the loading chamber and the 3D collagen construct within the chamber. The validation experiment was conducted by measuring the initial and final displacement undergone by the linear region of the loading chamber and the collagen construct following loading. 3D collagen constructs were prepared with 2.5 mg/ml collagen type-1 solution (Corning Life Sciences) neutralized to pH 7-8 with chilled 1N NaOH solution along with phosphate buffer, saline, and sterile water according to manufacturer's protocol. The sample solution was added into the grooves of each loading chamber and polymerized at 37° C. for 1 hour. For displacement measurements, embedded markers were placed at the ends and the center of the linear region of the loading chamber and collagen construct, corresponding to 0, 12.5, and 25 mm in length from the end nearest to the load application (FIG. 19A). Images of the samples were taken, run at initial and final positions in triplicates for each applied load of 1N, 2N, and 3N. The images were analyzed using an image processing software (ImageJ, NIH, US), and the initial and final displacements of the embedded marker for each sample at each applied strain was measured.

Finite Element Modeling of Strain and Stress Distribution

Figure 19B:
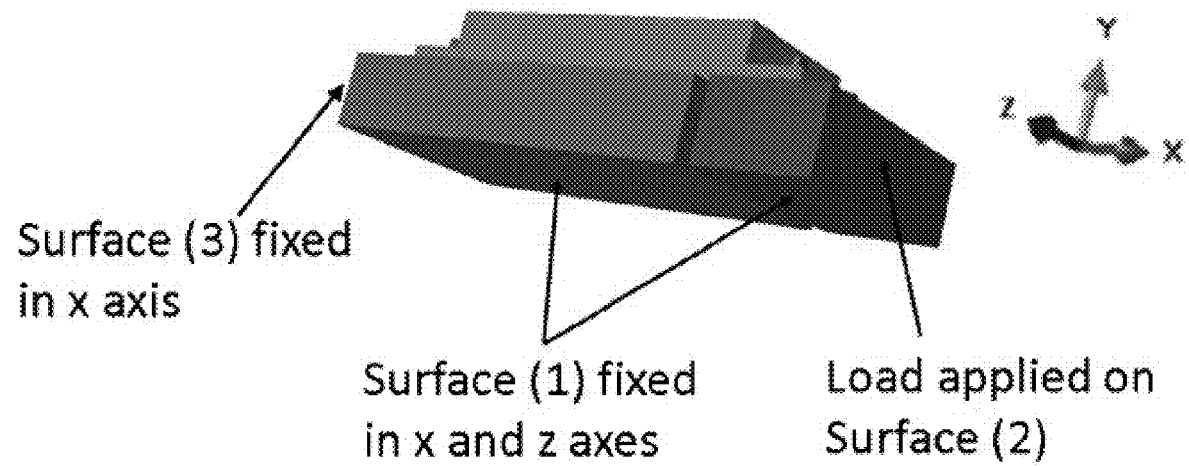

A Finite Element Model (FEM) was generated to investigate the strain and stress profiles experienced by the collagen constructs during mechanical stimulation using the uniaxial tensile strain bioreactor. The model assembly was meshed with C3D10I, a 10-node general purpose tetrahedron with improved surface stress formulation elements using ABAQUS (6.12, Dassault Systémes, France). Mesh sensitivity studies were conducted to obtain the most computationally efficient mesh without affecting the obtained results. The silicone loading chamber was modeled as a hyperelastic material while collagen constructs were modeled as a viscoelastic time-dependent material according to Prony series model. The material parameters in each case were obtained via nonlinear curve fitting of the experimental uniaxial tensile testing data. The polycarbonate moving and fixed plates were modeled as an elastic material. Young's modulus and Poisson's ratio were obtained from the supplier (McMaster-Carr, USA) and were 2.4 GPa and 0.35, respectively. Two representative views of the loading assembly with the surfaces used to apply the loading and boundary conditions are shown in FIG. 19B. Both the fixed and moving supporting plates bottom surfaces (1) were constrained in both X and Z axes. Surface (3) was constrained in the X axis. The load was applied on surface (2) via kinematic coupling with a reference point constrained in all degrees of freedom except the X direction. The load was applied as displacement-controlled boundary condition on the reference point. Surface-to-surface interaction was applied to the interface of silicone loading chamber and the polycarbonate plates and also between silicone and the collagen construct. For silicone-polycarbonate and silicone-collagen interactions, normal penalty hard contact and tangential static-kinetic exponential decay frictional contact was used.

Cell Culture, Construct Synthesis, and Bioreactor Loading Parameters

Human cardiomyocytes AC10, murine myoblasts C2C12, and murine osteoblasts OB6 were used to characterize the effect of the uniaxial tensile strain bioreactor on cell viability and proliferation. AC10s, C2C12s, and OB6 were maintained in DME/F-12 1:1 media (HyClone, US), DMEM/low glucose (HyClone, US), and αMEM (Life Technologies, US), respectively, with each media supplemented with 10% Fetal Bovine Serum (FBS, Gibco, US) and 1% Penicillin-Streptomycin solution (Life Technologies, US). 3D cellular constructs were prepared by encapsulating each cell line within neutralized collagen type-I solution at $1 \times 10^6$ cells/ml seeding density. The collagen solutions were added into the groove of the silicone loading chambers, polymerized at 37° C. for 1 hour, and incubated in their respective media for 48 hours. The samples were then subjected to cyclic loading using the uniaxial tensile strain bioreactor at an applied load equivalent to 2% strain with 0.1 Hz loading frequency for 1 hour/day for a period of 3 days. Constructs subjected to no loading (unloaded) were used as control samples. Samples were harvested at the day 3 and the linear region of the construct was excised to conduct the biological studies.

Cell Viability and Proliferation

The cell viability within the constructs subjected to mechanical loading was assessed at the end of three days using Live-Dead Assay kit (Life Technologies, US). Calcein and Ethidium Homodimer-1 dyes at 1:2 ratio were incubated with the samples for 30 minutes at 37° C., and fixed with 4% paraformaldehyde (Sigma, US). The constructs were subjected to confocal microscopy at 490/525 nm and 557/576 nm excitation/emission wavelengths for visualizing live and dead cells, respectively. DNA quantification was performed using PicoGreen dsDNA kit (Life Technologies, US) to indirectly determine the total number of cells within the loaded and unloaded (control) samples. Cells were liberated from the collagen constructs by mechanical disruption, resuspended in lysis buffer (50 mM Tris HCl, 1 mM $CaCl_2$, 400 μg/ml, pH=8) and incubated at 55° C. overnight. The lysate was diluted 1:10 in TE buffer and mixed with 1:200 dilution of PicoGreen dye in 1:1 ratio and incubated at room temperature for 5 minutes. The fluorescence intensities of the samples were measured at 480/520 nm excitation/emission wavelengths using a microplate fluorometer (Wallac 1420). The total amount of DNA was determined using a standard curve generated with varying amount of DNA (in ng) and their corresponding fluorescence values.

Matrix Organization of 3D Collagen Constructs

The structural changes in the construct matrix due to mechanical stimulation were examined using the Scanning Electron Microscope (SEM). The cellular collagen constructs were fixed overnight with 4% paraformaldehyde, then the samples were sequentially dehydrated by incubating them for 15 minutes each in a series of ethanol/water gradients followed by hexamethyldisilazane/ethanol gradients ranging from 30% to 100%. The constructs were air dried overnight, sputter coated, and visualized under SEM to observe the morphology and structure of the matrix.

Statistical Analysis

Four samples (n=4) were used for experimental characterization of the uniaxial tensile strain bioreactor. Student t-test with a confidence interval of $p<0.05$ was used to determine statistically significant difference between two groups. The data is reported as ±standard deviation.

Results and Discussion

Uniaxial tensile strain bioreactors for mechanical loading of musculoskeletal cells are an important tool for tissue engineering to study cellular biochemical responses and signaling pathways triggered by the synergistic effect of mechanical and micro-environmental cues. However, most of the current custom-built and commercial bioreactors for loading 3D cellular constructs are limited by the generation of non-linear strain profiles over the length of construct. The bioreactors also tend to be complex in operation and maintenance, and require handling of constructs which may risk the structural integrity of the construct. In this Example, a mechanical loading bioreactor that is straightforward in design and construction was utilized for the application of precise and homogenous uniaxial tensile strains to 3D cell-encapsulated collagen constructs. The bioreactor was programmed to operate at physiological loading strains (0-12%) and cycling frequencies (0.01-1 Hz) that mimic the in vivo environment of musculoskeletal tissues such as bone, tendon, ligament, and skeletal muscles that experience uniaxial stretch on a daily basis. The advantages of this uniaxial tensile strain bioreactor include that it is simple in set up, easy to operate and maintain, compact, and cost-effective when compared to existing bioreactors for mechanical stimulation of 3D collagen constructs.

Operation and Performance of the Uniaxial Tensile Strain Bioreactor

Figure 20A:
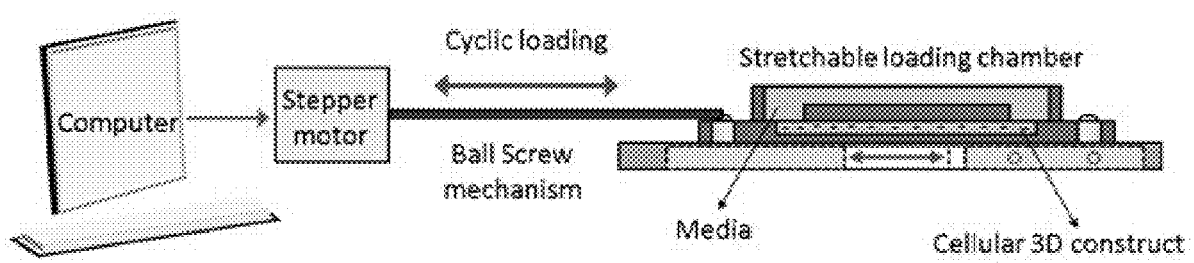
FIGS. 20A-20B: Operation and performance of the uniaxial tensile strain bioreactor as described in Example 2 herein.

The uniaxial tensile strain bioreactor comprises specifically-designed silicone loading chambers supported by a versatile actuation system comprising of a high torque stepper motor coupled with miniature ball screw assembly (FIG. 20A). The loading chamber design eliminates the necessity for clamps or anchors for direct gripping of samples and minimizes the risk of construct disintegration. This was achieved by the groove-and-island configuration of the loading chamber (FIG. 18), with the collagen constructs secured in the groove and supported by the island to ensure that they get stretched along with the loading chamber in the direction of load. LabVIEW-based GUI software was used to give input commands to the motor controller and can be programmed for different waveforms of loading to produce precise and reproducible movement of the moving plate through the stepper motor-ball screw actuation system. The cell-seeded constructs within the silicone loading chambers that were securely held by pins from the fixed and moving plate were stretched along with the reciprocal movement of the moving plate.

Figure 20B:
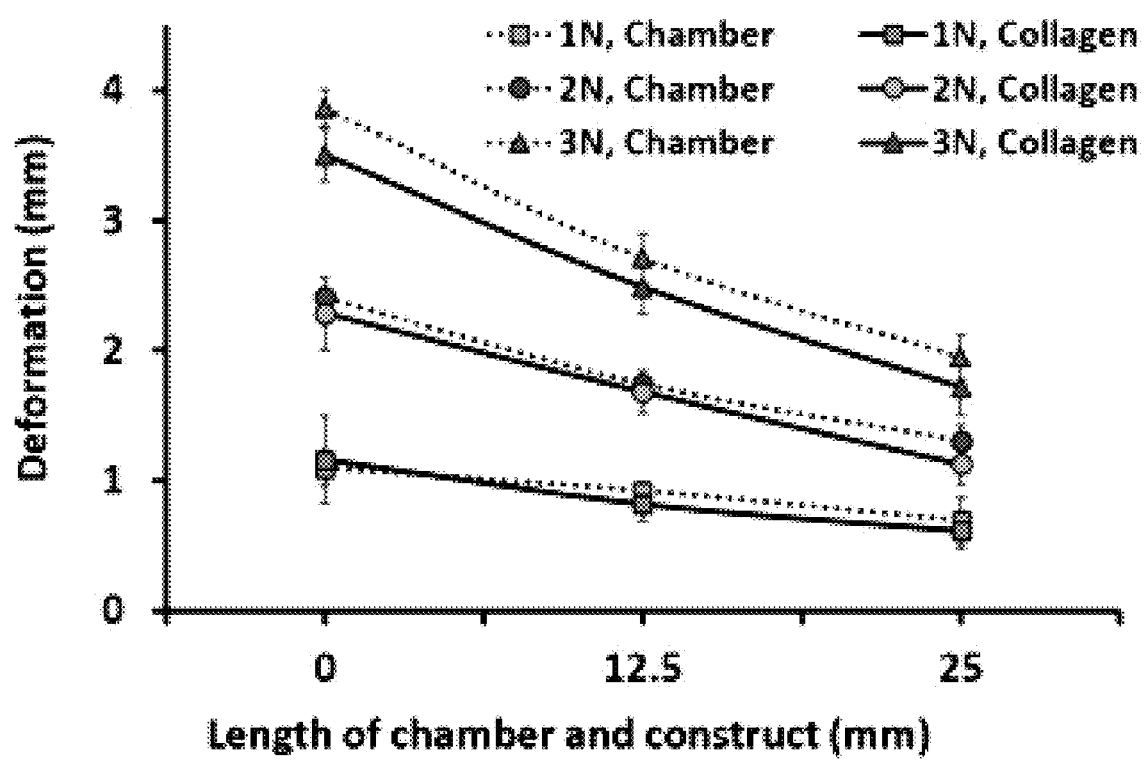

The uniaxial tensile strain bioreactor was experimentally validated to determine whether the design of the loading chamber is able to effectively transfer the applied loads to the collagen constructs with no substantial strain attenuation. The deformation experienced at the defined points of 0 mm, 12.5 mm, and 25 mm on the linear region of the loading chamber (dotted line) and collagen construct (solid line) was captured and measured through image-based analysis and depicted in FIG. 20B. No statistically significant difference was observed in the deformation experienced by the loading chamber versus the collagen constructs at any location along the linear length. This indicates that even without the use of anchor tabs or clamps the applied load is effectively being transferred from the loading chamber to the 3D collagen constructs. The groove-and-island configuration of the loading chamber is thus able to act as an indirect support for the construct to remain in place during mechanical loading and help preserve the structural integrity of the construct. Further, since the loading chamber is also the culture chamber for the samples, there are no procedures required to transfer the samples from culture conditions to loading fixtures, thus minimizing the handling labor, possible construct damage and risk of contamination.

The bioreactor was capable of stretching four silicone loading chambers simultaneously in one loading regime, with two cellular constructs in each chamber. The loading chambers were mounted onto the bioreactor assembly within a laminar flow biosafety cabinet, thus ensuring aseptic culture techniques throughout the process. The uniaxial tensile strain bioreactor along with its electronic components can be placed in a standard tissue culture incubator during operation, allowing long-term culture in a temperature and pH-controlled environment.

Bioreactor-Induced Longitudinal Tensile Strain Profile within 3D Constructs

Performance of a mechanical loading bioreactor is influenced by considerations such as chamber design, clamping method, actuator system, and dimensions of construct. To investigate the strain and stress profiles generated during loading with the custom-built uniaxial tensile strain bioreactor described in this Example, a FE-based model was generated. The static model was then validated using the experimental deformation data for the linear region of the loading chamber and collagen construct at loads of 1N, 2N, and 3N shown in FIG. 20B. The dynamic model was validated using the experimental deformation data for the linear region of the collagen construct at an applied load of 2N and cycling frequencies of 0.1 Hz, 0.5 Hz, and 1 Hz. The FEM-predicted values were found to be within ±10% accuracy when compared to the experimentally measured data. Model generation and validation data are shown in FIGS. 10, 16A-16B, 26-29.

Figure 21A:
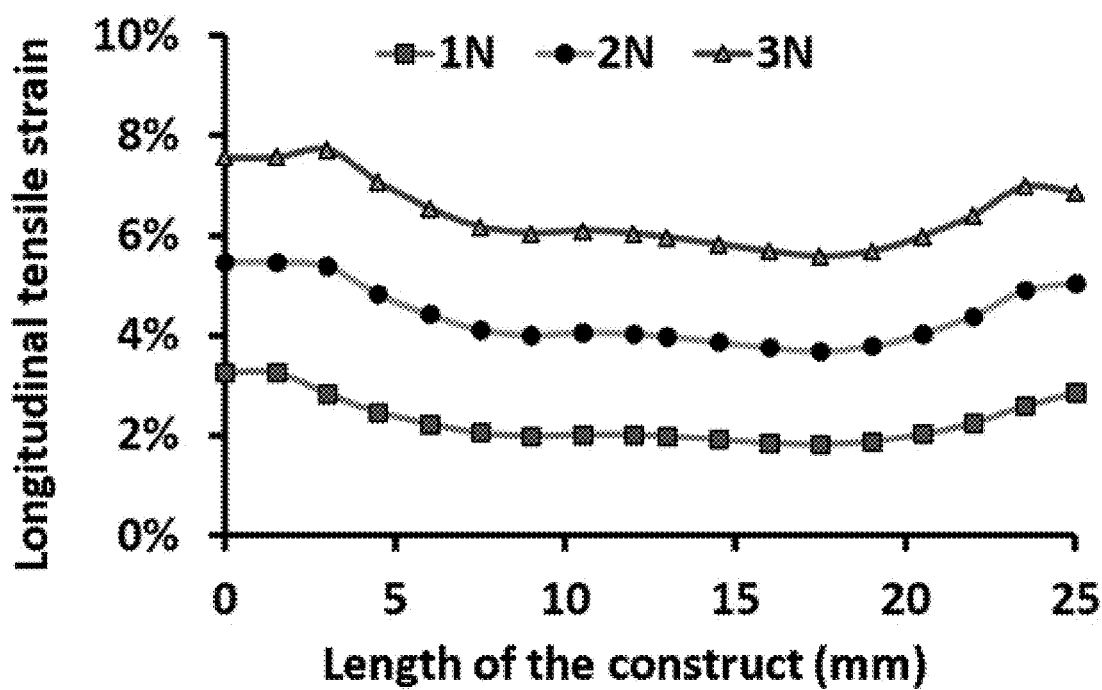
FIGS. 21A-21D: Bioreactor-induced longitudinal tensile strain profile within 3D constructs predicted using FEM.
Figure 21B:
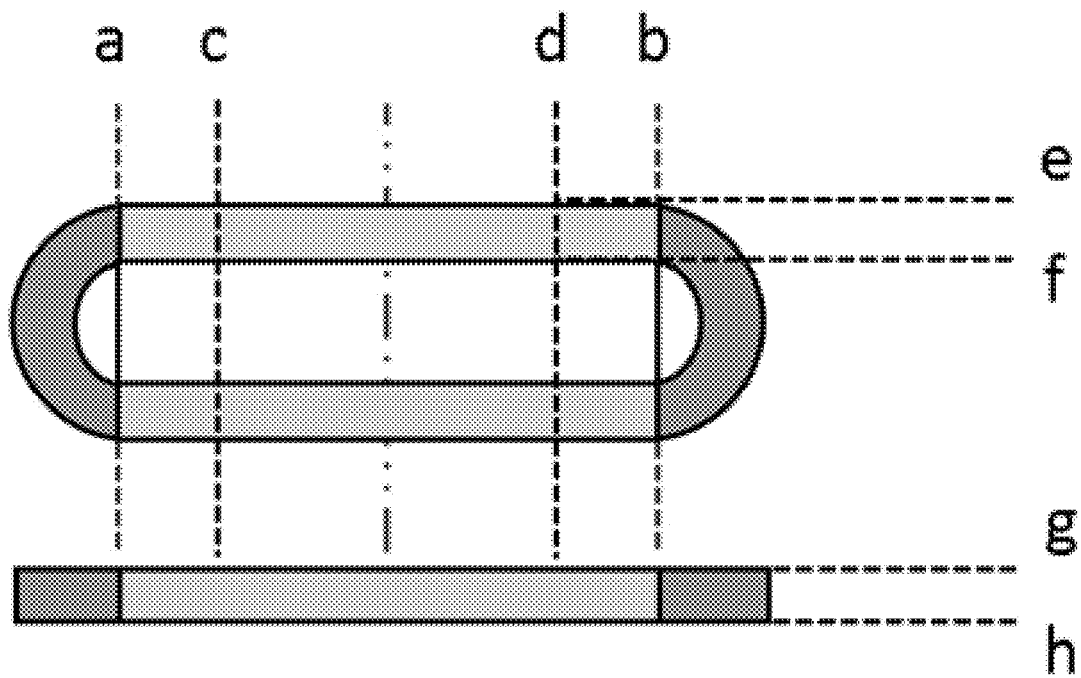

The validated FEM was subsequently used to investigate the strain contours experienced within the collagen construct in order to characterize the strain experienced by the linear region of the collagen construct. The longitudinal tensile strain acting parallel to the load of application was determined along the length (a) to (b), width (c) to (d), and thickness (g) to (h) of the linear part of the construct as shown in the schematic in FIG. 21B. It is observed from FIG. 21A that the predicted longitudinal tensile strain across the length of the construct is very uniform over a 15 mm length, ranging from 5 mm (c) to 20 mm (d) of the length of construct.

Figure 21C:
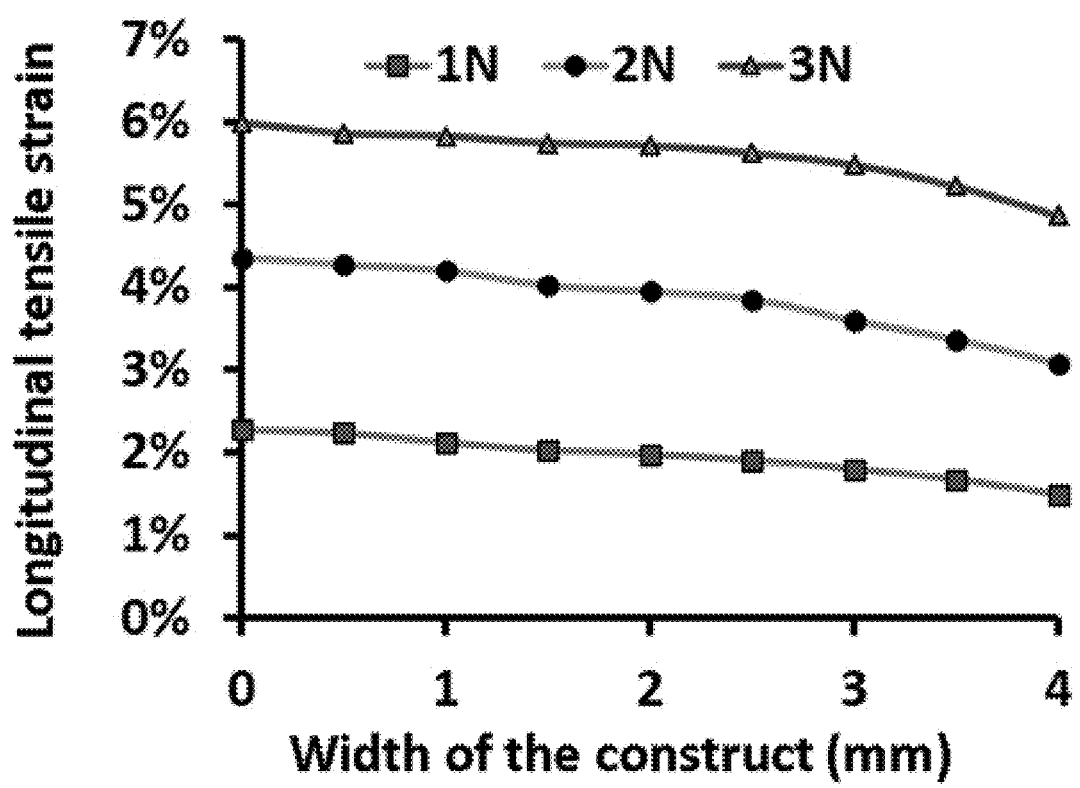
Figure 21D:
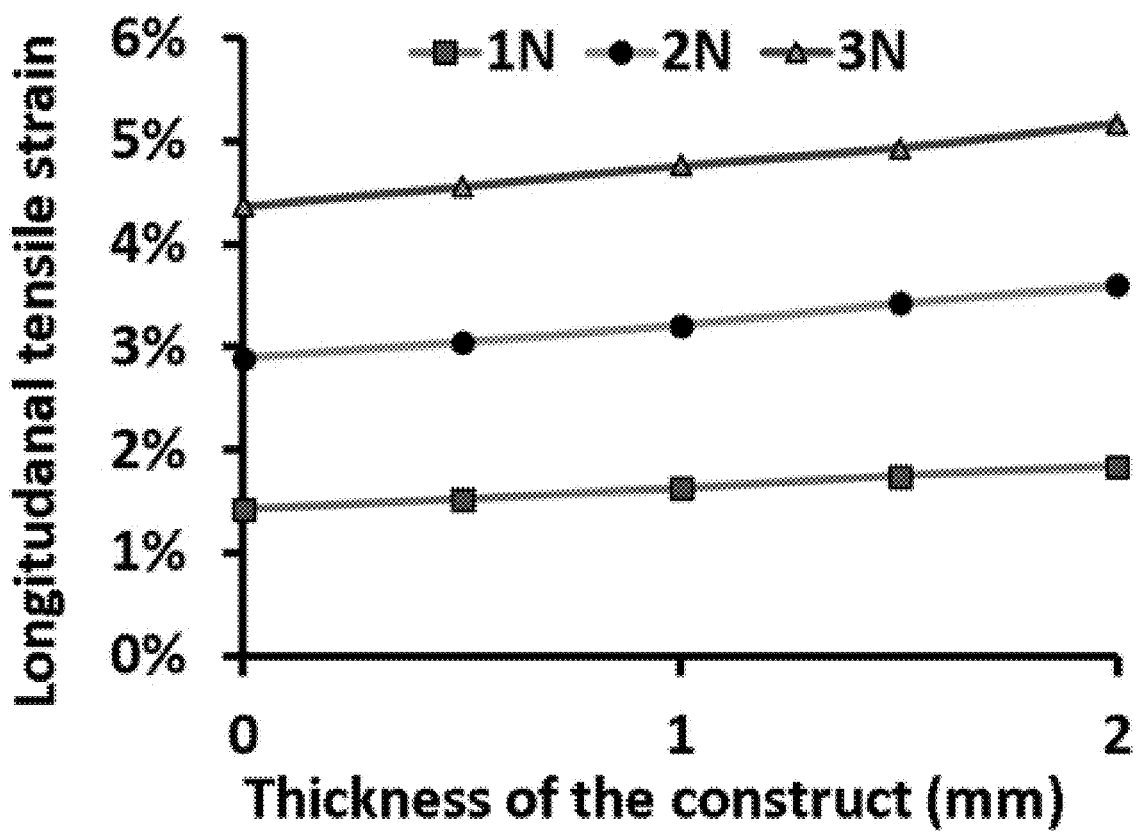

At applied loads of 1N, 2N, and 3N, the longitudinal tensile strain within the collagen construct was relative uniform at 2±0.11%, 4±0.19%, and 6±0.24% over the length of 15 mm, respectively. The magnitude of strains from (c) to (a) and (d) to (b) was seen to increase from the uniform strain value by 1.2%, 1.5%, and 1.8%, respectively. This increase in strain at the ends, though not as amplified as direct gripping of samples, can be attributed to the change in geometry of the loading chamber and the presence of the island that acts as an indirect anchor for the 3D collagen constructs. FIGS. 21C-21D demonstrate that the longitudinal strain profile across the width and thickness of the construct is fairly homogenous for each applied load. The strain contours across both width and thickness of the construct are within ±0.2-0.3% of the uniform strain values 2%, 4%, and 6% for applied loads of 1N, 2N, and 3N, respectively. The decrease of 0.5% observed near line (f) for the strain magnitudes estimated across the width can be attributed to the presence of the island that resists the load. Based on these contours, it can be concluded that the region of 15×4×2 mm ranging from line (c) to line (d) achieves uniform longitudinal tensile strain profile. This region with a volume of 120 µl is around 60% of the linear part of the 3D collagen construct.

Lack of focus on detailed characterization of strain profiles in the literature employing such devices makes it difficult to evaluate the performance the custom-built bioreactor with respect to existing alternatives. Nevertheless, other bioreactors use hooks or punch holes to grip collagen sponge-based constructs, and exhibit uneven distribution of strain profile with high risk of construct disintegration. For example, one known system has its estimated homogenous strain region on the membrane to be 140 mm$^2$ rectangular region at the center, which is only 47% of the effective area of characterization.

Bioreactor-Induced Compressive Strain within 3D Constructs

Figure 22:
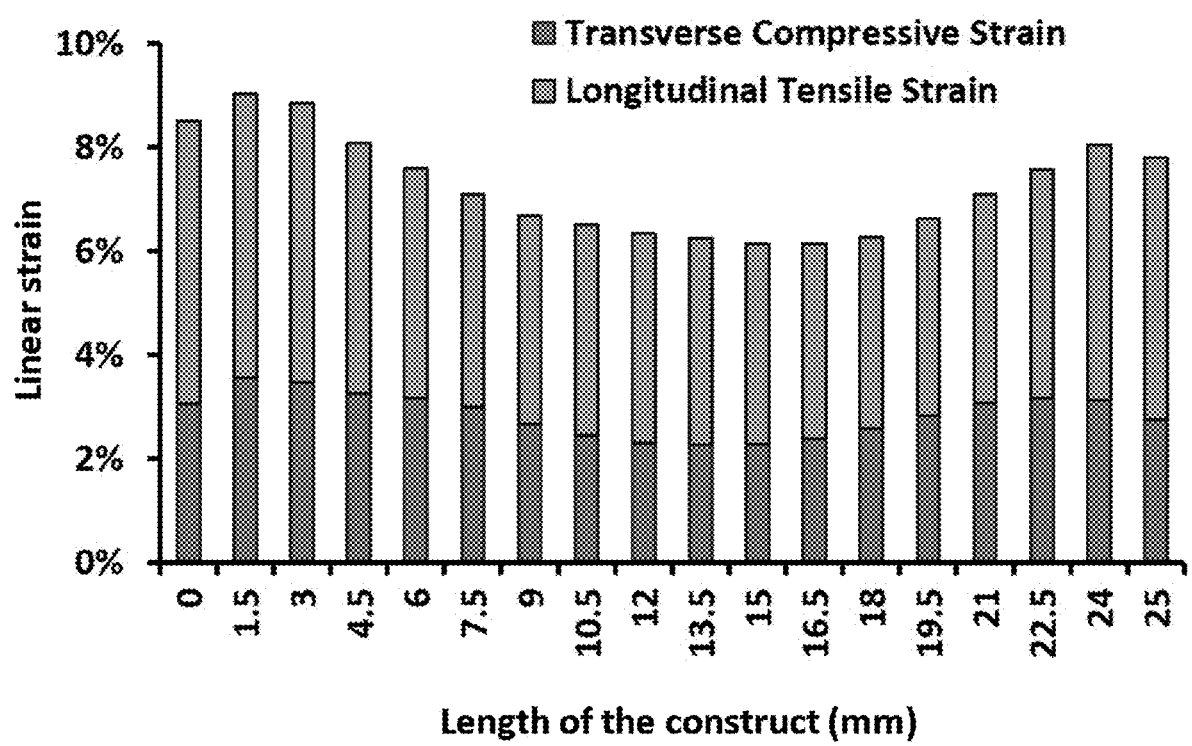
FIG. 22: Bioreactor-induced tensile and compressive linear strains within 3D constructs predicted using FEM. Comparison of the longitudinal tensile strain and transverse compressive strain experienced by the collagen construct across its length on subject to a uniaxial tensile load of 2N. Transverse compressive strains account for only 33% of the total strain experienced by the construct. The homogenous tensile strain across the 15×4×2 mm region is predominantly 'uniaxial' in nature.

In addition to longitudinal tensile strains, uniaxial loading also produces transverse compressive strain that acts perpendicular to the direction of load application due to the Poisson effect. Hence, the magnitudes of longitudinal and transverse linear strains produced by the bioreactor were identified to determine the dominant strain experienced by the 3D collagen constructs. FIG. 22 shows the ratio of transverse compressive strain in comparison to the longitudinal tensile strain experienced by the length of the collagen construct at an applied load of 2N. It is evident that the transverse compressive strain is approximately 33±0.4% of the total strain experienced by the construct in the region of homogenous longitudinal tensile strain. At the center of the construct with a uniform tensile strain of 4%, the predicted transverse compressive strain is 2.23%. This indicates that though the strain experienced by the construct is not purely uniaxial, the transverse strains are significantly and consistently lower than the longitudinal strains along the length of the region of interest of the construct. These results indicate that the volume of 15×4×2 mm$^3$ of the 3D construct experiences homogenous tensile strains majorly acting in the longitudinal direction and hence can be considered 'uniaxial' in nature. Therefore, the bioreactor can be used to study the effect of uniform and predominantly uniaxial longitudinal tensile strains on viability, proliferation, differentiation, and morphological response of cells. The presence of transverse compressive strain may complicate studying the effect of tensile strains on cellular mechanobiology. However, there are evidences that fibroblasts respond similarly to pure uniaxial strain versus predominantly uniaxial strain, which indicate that low transverse compressive strains have a negligible effect on cells responsive to longitudinal stretch.

Figure 23A:
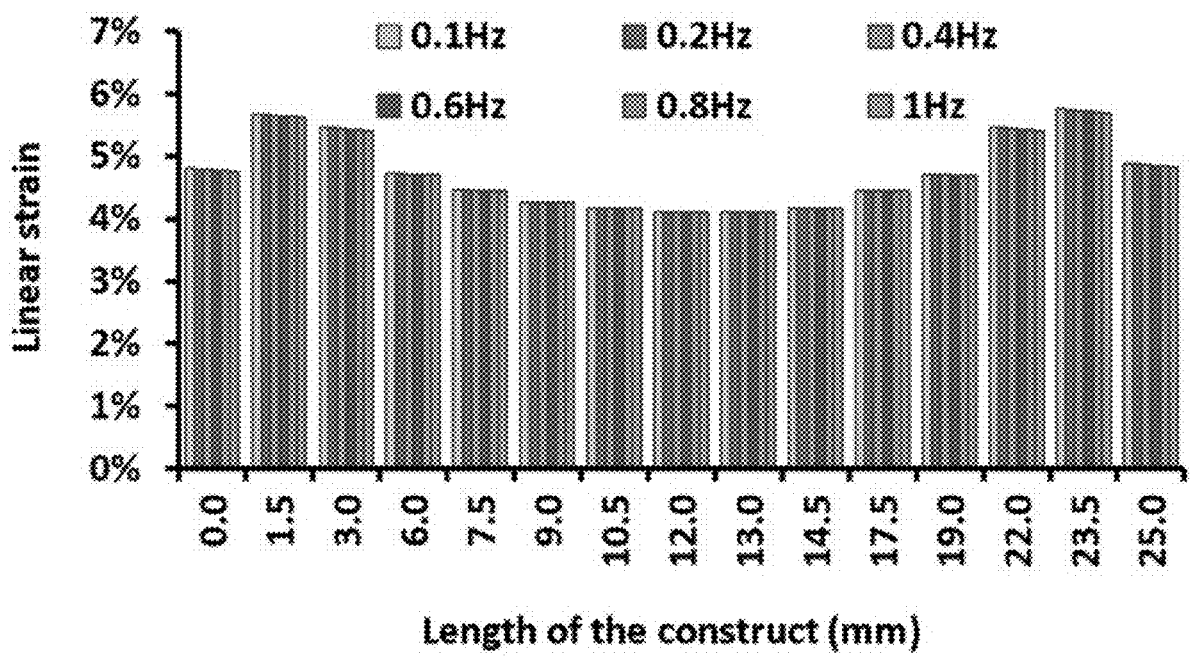
FIGS. 23A-23C: Bioreactor-induced strain and stress profiles within 3D constructs during cyclic loading predicted using FEM.
Figure 23B:
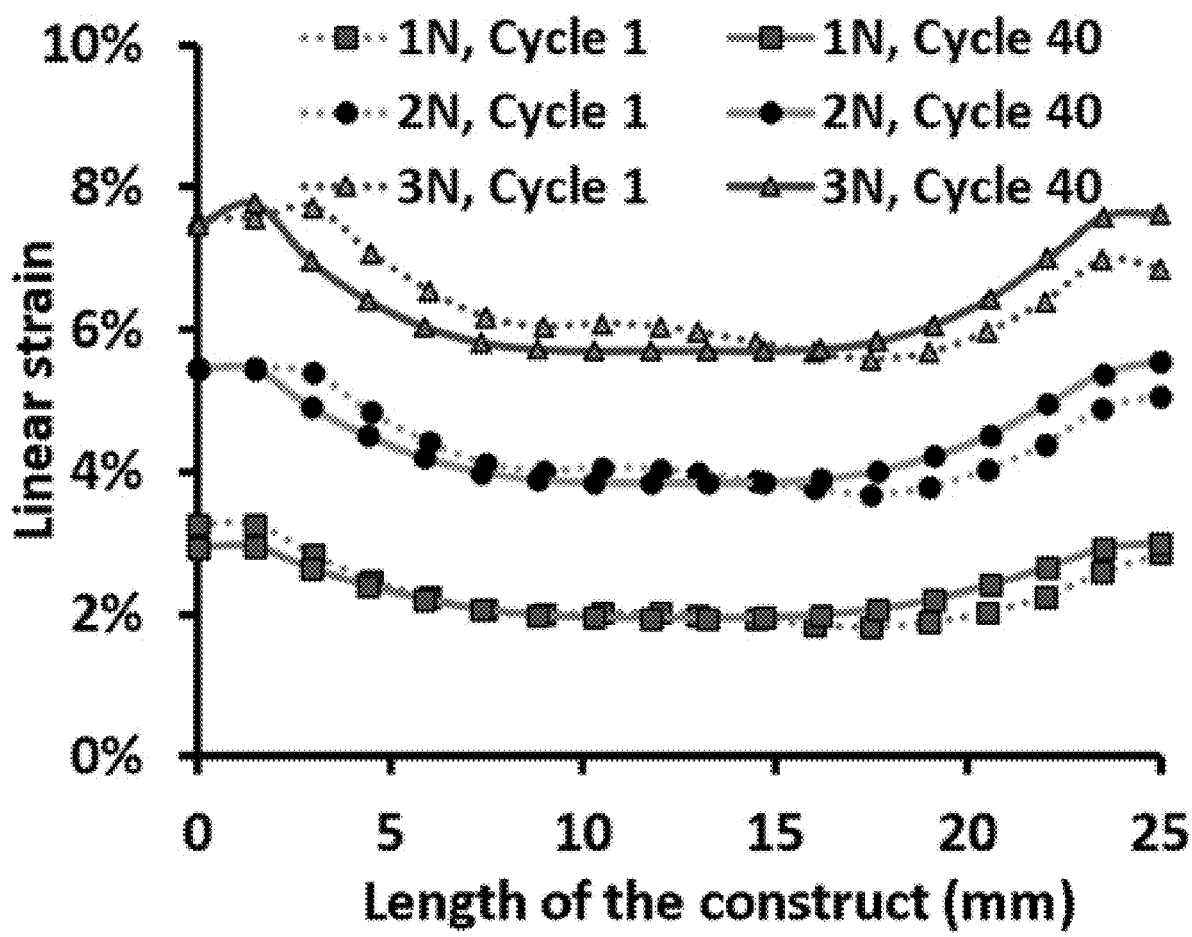
Figure 23C:
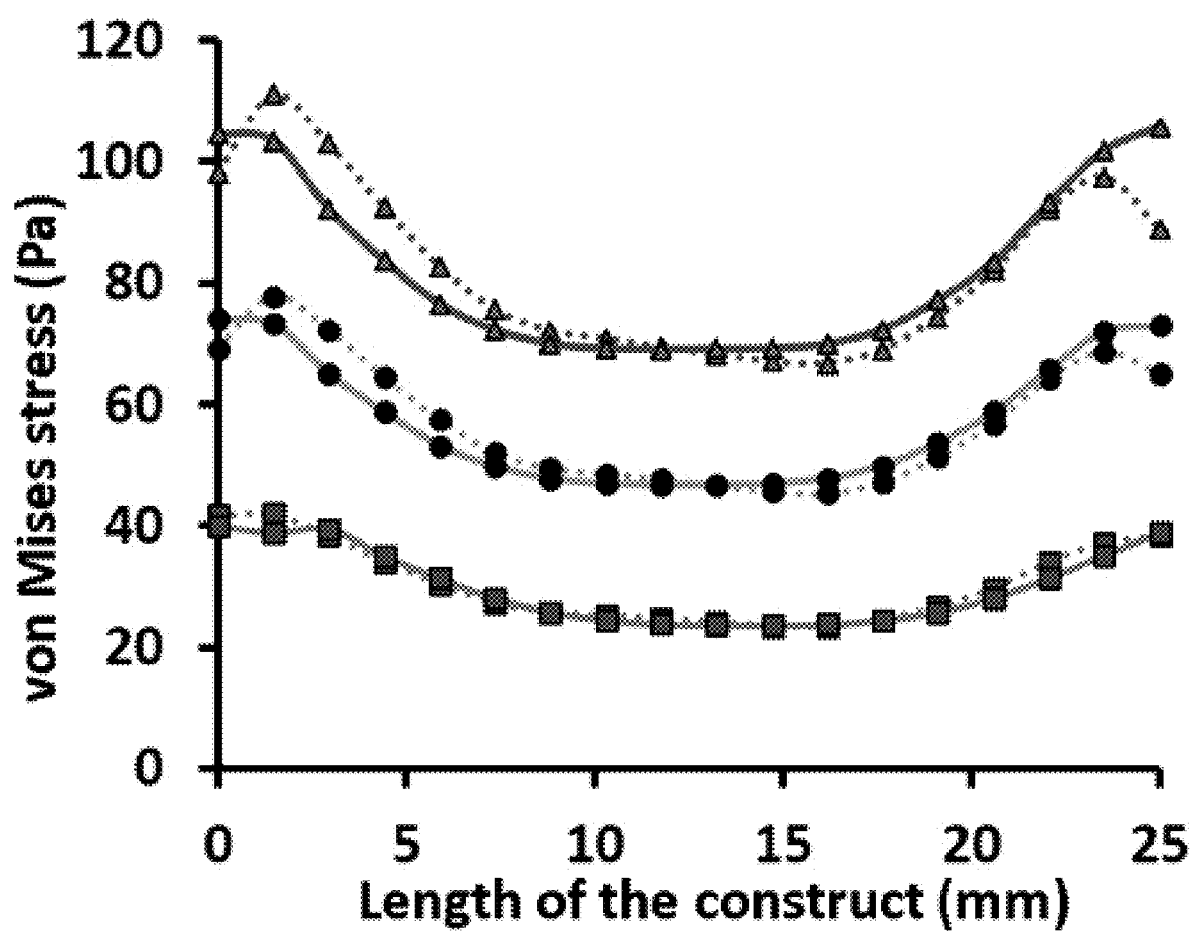

Bioreactor-Induced Strain and Stress Profiles within 3D Constructs During Cyclic Loading Since tissues under in vivo mechanical loading exist in dynamic conditions, the performance of the uniaxial tensile strain bioreactor was evaluated by subjecting the 3D collagen constructs to cyclic loading using FEM. Cyclic loading at different frequencies was simulated using triangular waveform and the longitudinal strain profile was recorded for an applied load of 2N (FIG. 23A). The strain contours clearly demonstrate that there is negligible difference in the strain values along the length of construct with varying frequencies, indicating that the bioreactor is stable over different cyclic loading regimes. The effect of cycle numbers on the stress and strain profiles was studied by simulating cyclic loading at 0.5 Hz for a total of 40 cycles. FIGS. 23B-23C represent the longitudinal tensile strain and von Mises stress profiles obtained during cycle loading, at cycle number 1 versus cycle number 40 at the applied loads of 1N, 2N, and 3N. No significant differences are observed in the homogeneity of the strain profiles between cycle 1 and cycle 40 (FIG. 23B). The strain and stress profiles at cycle 40 in fact look more homogenous when compared to cycle 1, along with lowered stress concentration at the ends of the linear region of the construct at higher cycle number (FIG. 23C). Therefore, the uniaxial tensile strain bioreactor is not only capable of applying homogenous strain to the linear region of the collagen construct, but is also able to consistently reproduce the uniformity in strain and stress profiles during each cycle of loading.

Figure 24A:
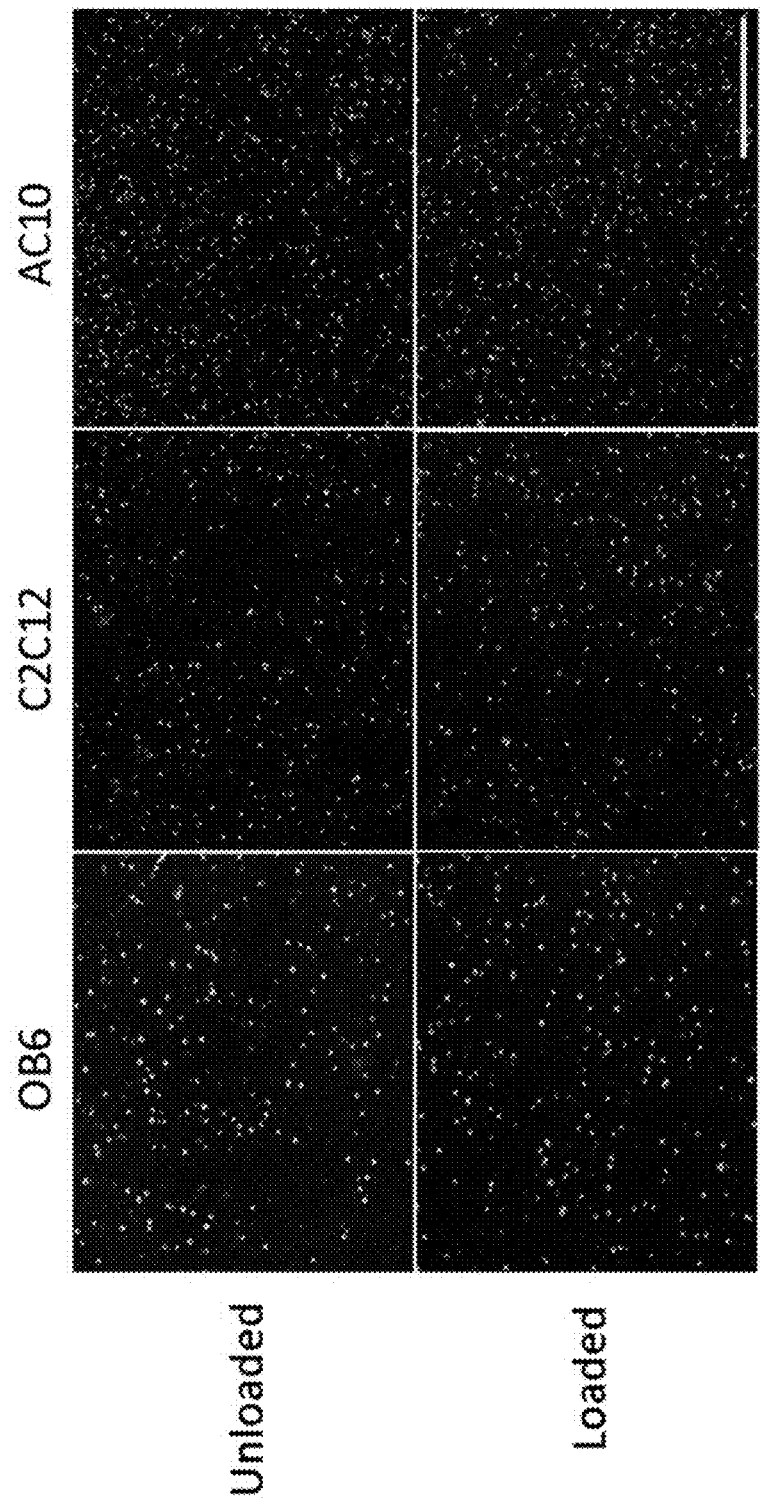
FIGS. 24A-24B: Effect of bioreactor on cell viability and proliferation within 3D constructs through experimental determination.
Figure 24B:
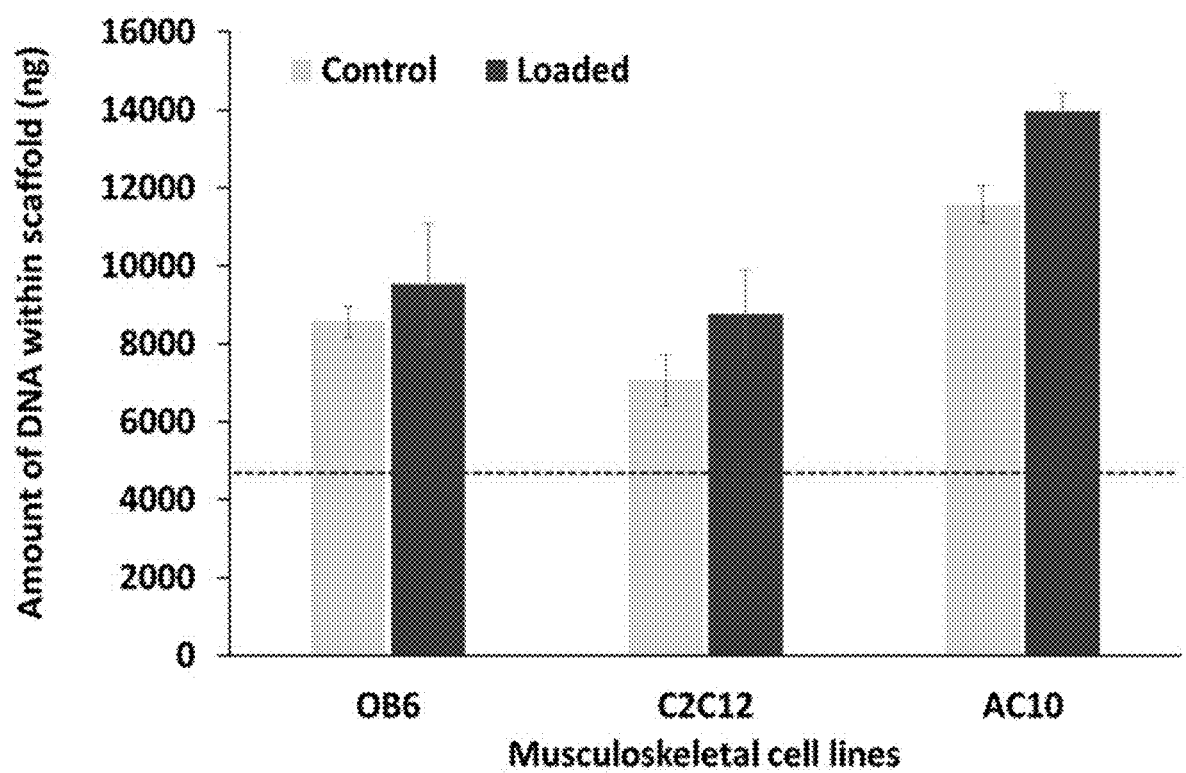

Effect of Bioreactor on Cell Viability and Matrix Organization within 3D Constructs After characterizing the performance and reproducibility of the uniaxial tensile strain bioreactor through Finite Element Analysis, biological assays were performed to determine the effect of uniaxial tensile strains on cell viability, proliferation, and matrix structure using cell lines belonging to different musculoskeletal lineages. FIG. 24A shows representative images of a live-dead assay performed for loaded and unloaded constructs seeded with OB6, C2C12, and AC10 cells using confocal microscopy. The results indicate that there is no significant difference in cell viability between the control and loaded constructs in all three sample sets, confirming that the uniaxial tensile strain bioreactor is not causing cytotoxicity to cell seeded within the constructs. Furthermore, the PicoGreen DNA quantification data (FIG. 24B) shows a 2.5-fold increase in the amount of DNA for OB6, 2-fold increase in C2C12, and almost a 4-fold rise in AC10 for both control and loaded samples compared to the initial DNA amount of 4500 ng, establishing that not only are the loaded cells viable, but they are metabolically active and proliferating within the construct. The increased number of dead cells seen in the case of AC10 cells within both control and loaded samples can be attributed to overcrowding due to the 4-fold increase in cell density that would have led to subsequent cell death.

Figure 25:
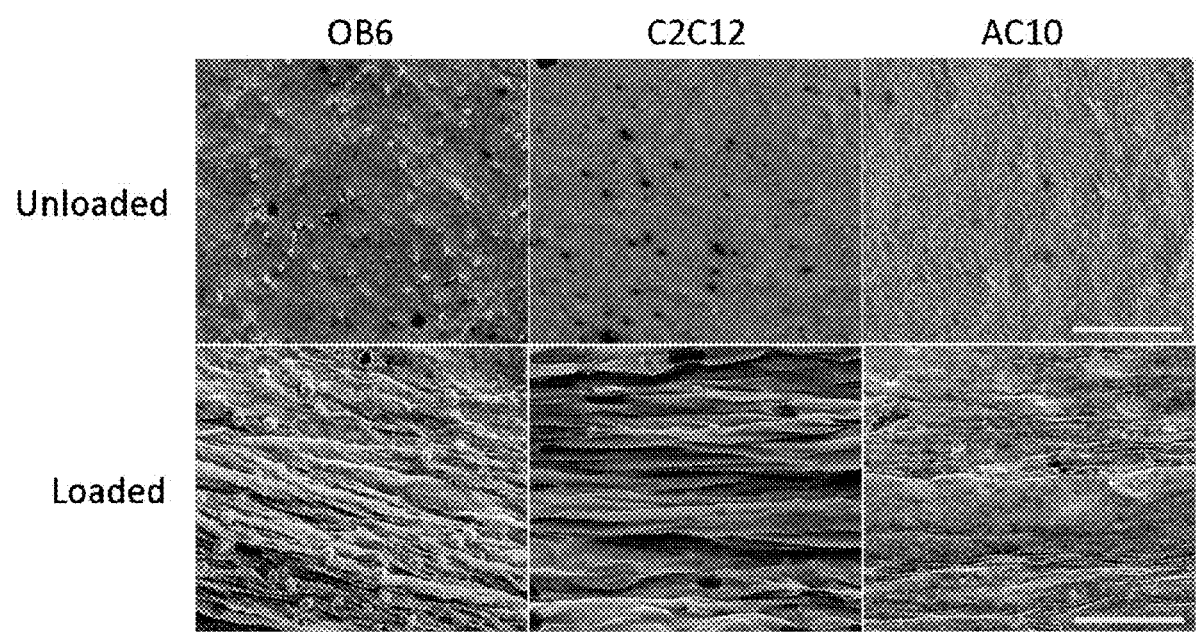
FIG. 25: Effect of bioreactor on collagen matrix organization within 3D constructs through experimental determination. Scanning Electron Micrographs of the loaded (2% strain, 0.1 Hz, 1 hour/day) and unloaded cell-encapsulated 3D collagen constructs at day 3. Scale bar is 100 µm. Matrix organization is visible in all loaded samples, with the orientation of the fibers being parallel to the axis of load application.
Figure 26:
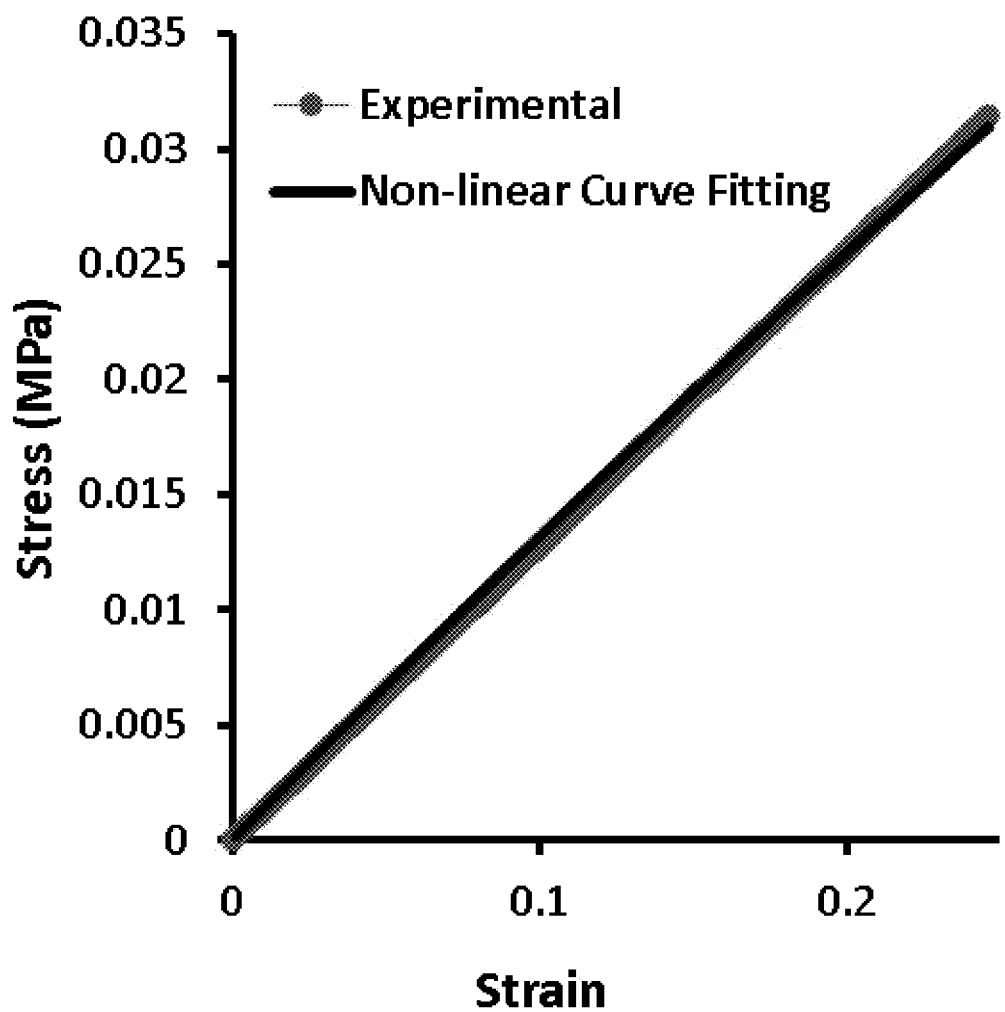
FIG. 26: Material properties of silicone loading chambers. Stress strain curves obtained from both tensile mechanical testing of the silicone loading chambers (n=6) and FEM model.
Figure 27:
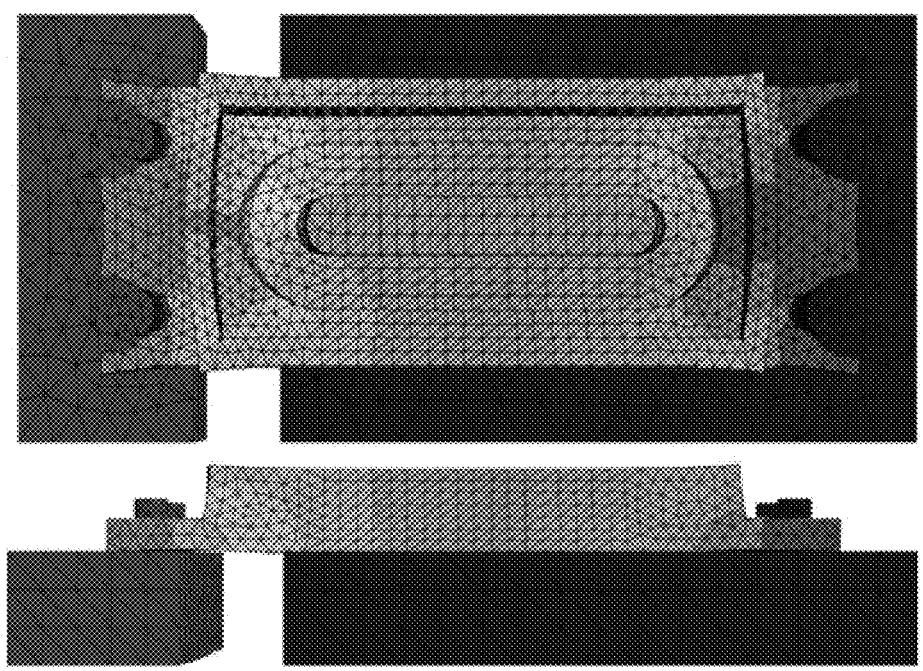
FIG. 27: Finite Element Model Generation. Representative deformation contour of the 3D collagen construct within the silicone loading chamber at an applied load of 3N.
Figure 28:
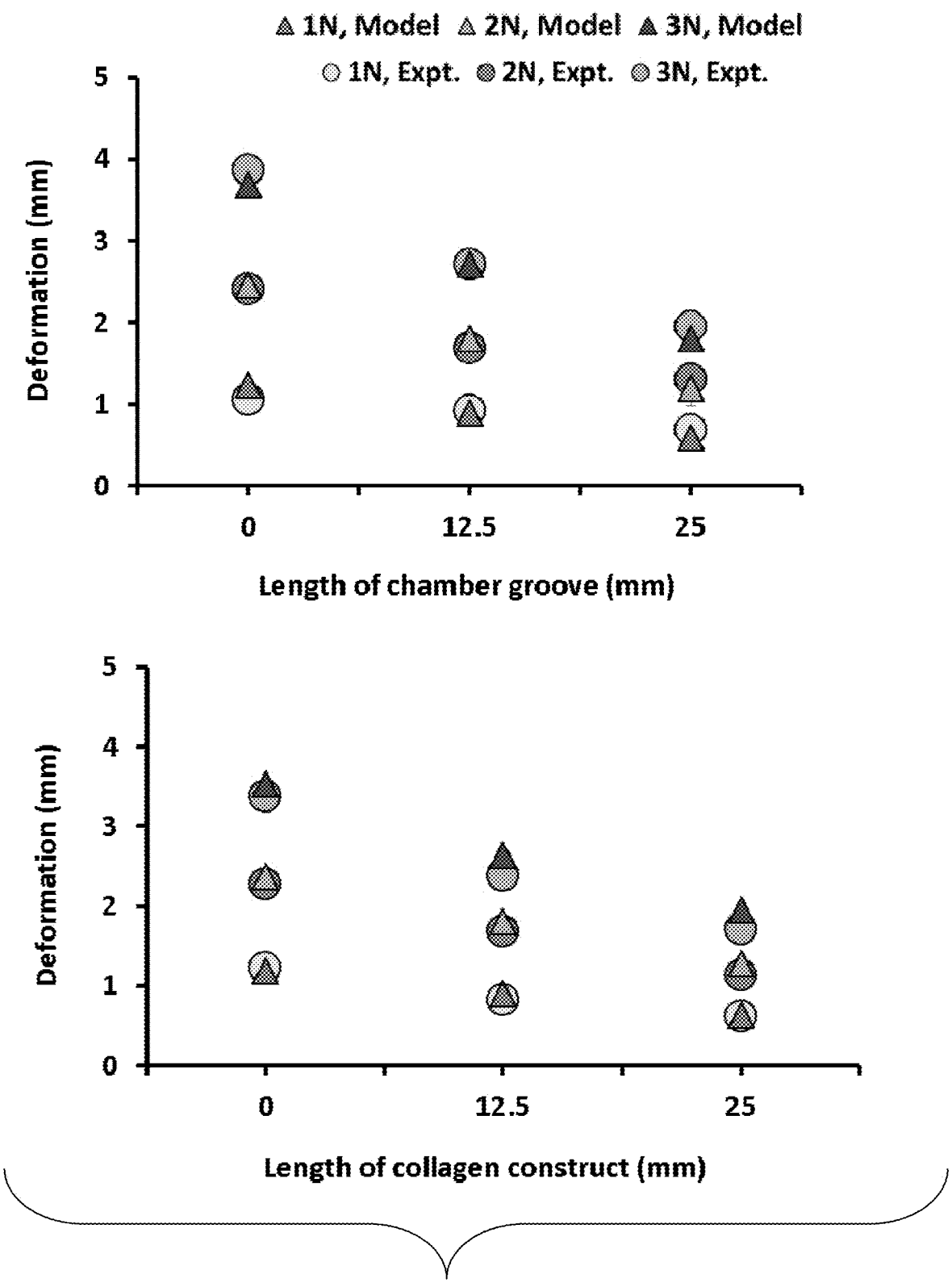
FIG. 28: Finite Element Model Validation: Static loading. Comparison between the deformations experienced by the collagen constructs experimentally and numerically at various applied loads of 1N, 2N, and 3N. The data obtained from the FEM was found to be within ±10% of the experimentally measured data.
Figure 29A:
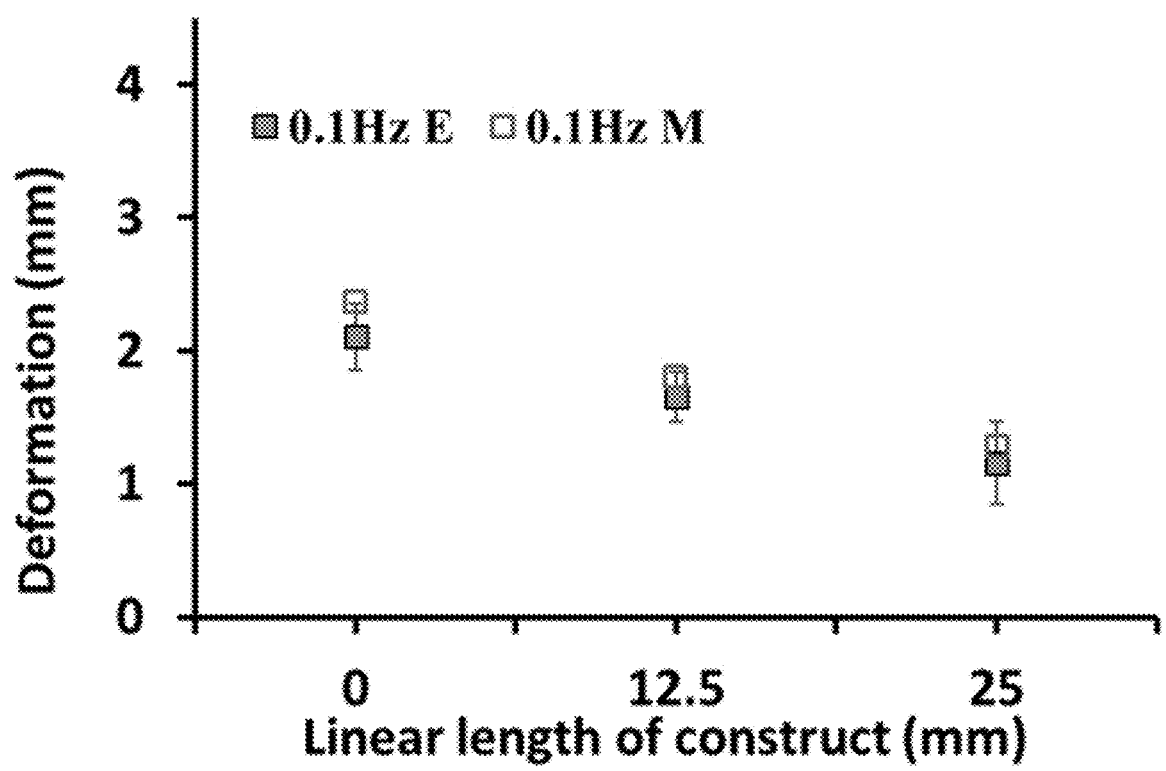
FIGS. 29A-29C: Finite Element Model Validation: Dynamic (Cyclic) Loading. Comparison between the deformations experienced by the collagen constructs determined experimentally (E) and numerically through FEM (M) for the applied load of 2N at various applied frequencies of 0.1 Hz (FIG. 29A), 0.5 Hz (FIG. 29B), and 1 Hz (FIG. 29C). The data obtained from the FEM was found to be within ±10% of the experimentally measured data.
Figure 29B:
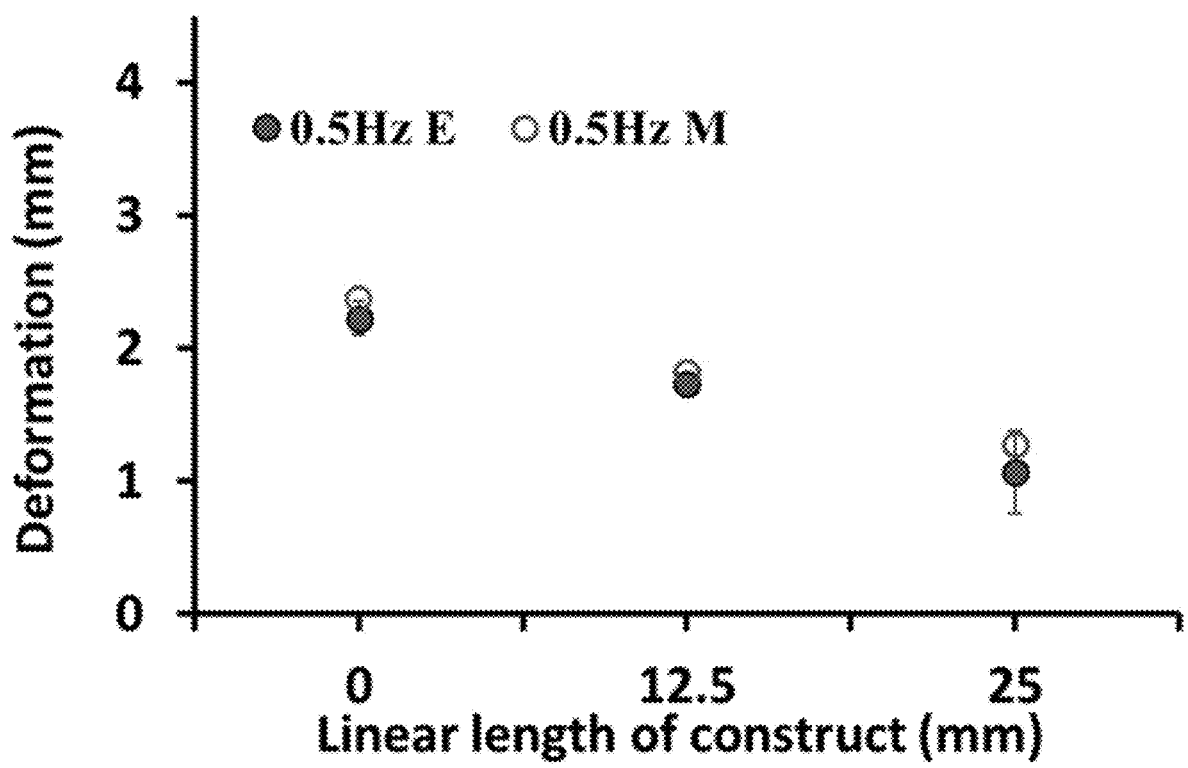
Figure 29C:
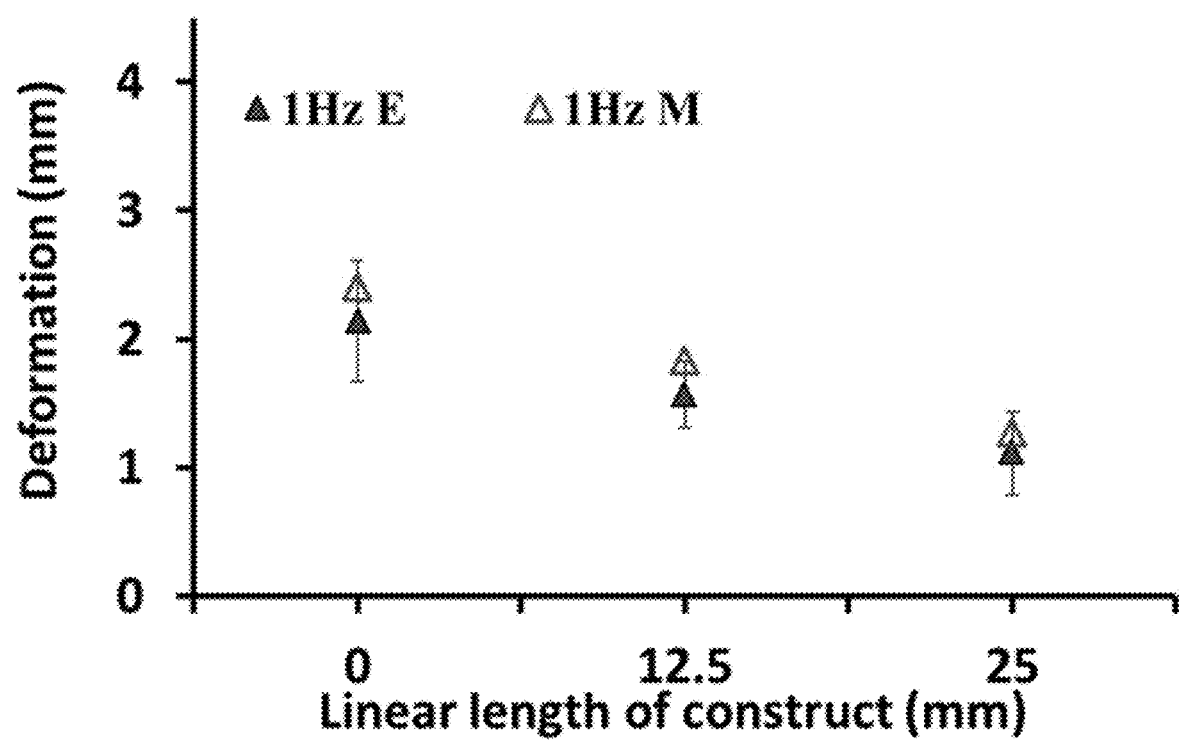

The 3D cell-encapsulated collagen constructs visualized through SEM displays an increased level of matrix organization and structure within the construct (FIG. 25). Compared to the unloaded samples, the loaded samples show a definitive orientation, with matrix organization observed to be predominantly parallel to the axis of load application in all the three groups. Mechanical conditioning of cells and their extracellular matrix increases cell proliferation and exhibits enhanced structural organization. Thus, the biological characterization data obtained demonstrates the ability of the bioreactor to elicit appropriate responses from various musculoskeletal cell lines encapsulated within 3D collagen constructs.

The simple and cost-effective bioreactor described in this Example can be operated at various physiological loading strains (0-12%) and frequencies (0.01-1 Hz) to apply precise and homogenous tensile strains over 60% of the effective region of the 3D collagen construct, with the strain being predominantly uniaxial in the longitudinal direction. The strain profiles obtained are consistent and stable during cyclic loading conditions, and the bioreactor is able to promote cell viability, proliferation, and matrix organization of the cell-encapsulated constructs.

All publications, including patents and non-patent literature, referred to in this specification are expressly incorporated by reference herein. Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

What is claimed is:

1. A scaffold-stretching system comprising:
   at least one stretchable loading chamber;
   at least one scaffold material supported by the stretchable loading chamber;
   the stretchable loading chamber including at least one groove on a top surface of the stretchable loading chamber, the groove having opposing linear portions that are connected by opposing semi-circular portions;
   wherein the semicircular portions of the groove link opposing linear portions of the scaffold material, and provide mechanical support and stability during stretching;
   wherein the scaffold material is capable of receiving supply of cells, and allowing for cultivation of a cellular three-dimensional scaffold in the scaffold material; and
   at least one mechanical loading system configured for application of for applying cyclic and static uniaxial tensile mechanical loading on the cultivating cellular three-dimensional scaffold, and mimicking the in vivo environment of musculoskeletal, cardiovascular, and other tissues that experience uniaxial strains.

2. The scaffold-stretching system of claim 1, wherein the opposing linear portions and opposing semi-circular portions define a mound at a center of the stretchable loading chamber configured to hold the scaffold in place during stretching, and configured to prevent the opposing linear and semi-circular portions from touching during loading.

3. The scaffold-stretching system of claim 1, wherein the stretchable loading chamber includes at least one well that is configured to hold a sufficient amount of a culture medium for cell survival, proliferation, and differentiation.

4. The scaffold-stretching system of claim 1, wherein the stretchable loading chamber includes one or more pin holes positioned at opposing ends of the stretchable loading chamber that are configured to accept holding pins of supporting base plates in order to apply loading.

5. The scaffold-stretching system of claim 1, wherein the stretchable loading chamber comprises silicone.

6. The scaffold-stretching system of claim 1, wherein the mechanical loading system comprises:
- at least one fixed plate and at least one movable plate, each of the fixed and movable plates having upper surfaces that are positioned in the same plane; each of the fixed and movable plates having a plurality of pins extending from the upper surface that are configured for holding at least a portion of the stretchable loading chamber; and,
- at least one driving mechanism operatively connected to a first end of the movable plate, the driving mechanism being configured for moving the movable plate in a uniaxial direction toward and away from the fixed plate.

7. The scaffold-stretching system of claim 6, wherein the fixed plate is configured to provide a base for slidably supporting the stretchable loading chamber, and to support the weight of the stretchable loading chamber when loaded with scaffold and media during mechanical loading.

8. The scaffold-stretching system of claim 6, wherein the movable plate is configured to transmit uniaxial motion to the stretchable loading chamber.

9. The scaffold-stretching system of claim 6, wherein a gap exists between the fixed plate and a second end of the movable plate, wherein the length of the gap is sufficient for preventing the fixed and movable plates from coming into contact during a cyclic motion.

10. The scaffold-stretching system of claim 6, wherein the fixed plate and the movable plate are slidingly supported by opposing guiding sleeves, the opposing guiding sleeves being configured to allow translational motion of the movable plate, while the fixed plate is held in place by the guiding sleeves.

11. The scaffold-stretching system of claim 10, wherein the length of the guiding sleeve is such that the movable plate can be pulled up to strain values that would cover the entire range of physiological loading regimes, determined in terms of the uniaxial elongation of the linear part of the groove of the silicone loading chamber.

12. The scaffold-stretching system of claim 6, wherein the driving mechanism includes:
- a ball screw drive assembly having a ball nut and a ball screw, the ball screw drive assembly being configured to convert rotational motion to uniaxial translational motion of the drive assembly; and,
- one or more connecting rods having first ends attached to the first end of the movable plate, and having second ends attached to the ball screw drive assembly.

13. The scaffold-stretching system of claim 12, wherein the connecting rods are configured to transfer linear motion of the ball nut due to rotation of the ball screw to the movable plate, thereby producing stretching of the stretchable loading chambers.

14. The scaffold-stretching system of claim 12, wherein a two-phase high torque stepper motor is operatively connected to the ball screw assembly, wherein the two-phase high torque stepper motor is capable of producing controlled and precise strains at specified frequencies.

15. The scaffold-stretching system of claim 12, wherein the scaffold material comprises a cellular gel-based scaffold.

16. The scaffold-stretching system of claim 1, comprising human skin substitute (HSS) in the stretchable loading chamber.

17. The scaffold-stretching system of claim 16, wherein the HSS comprises collagen and human keratinocytes.

* * * * *

UNITED STATES PATENT AND TRADEMARK OFFICE
CERTIFICATE OF CORRECTION

PATENT NO. : 11,142,739 B2
APPLICATION NO. : 16/081977
DATED : October 12, 2021
INVENTOR(S) : Gayathri Subramanian, Mostafa Elsaadany and Eda Yildirim-Ayan It is certified that error appears in the above-identified patent and that said Letters Patent is hereby corrected as shown below:

In the Claims

Column 28, Claim 1, Line 47 - 48 please correct:
"at least one mechanical loading system configured for application of for applying cyclic and static uniaxial"

To:
--at least one mechanical loading system for applying cyclic and static uniaxial--

Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*